US008741970B2

(12) United States Patent
Brown

(10) Patent No.: US 8,741,970 B2
(45) Date of Patent: *Jun. 3, 2014

(54) COMPOSITION AND METHOD FOR THE ENHANCEMENT OF THE EFFICACY OF DRUGS

(75) Inventor: Tracey J. Brown, Flemington (AU)

(73) Assignee: Alchemia Oncology Pty Limited, Eight Mile Plains (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/325,842

(22) Filed: Dec. 14, 2011

(65) Prior Publication Data
US 2013/0197103 A1 Aug. 1, 2013

Related U.S. Application Data

(63) Continuation of application No. 09/889,203, filed as application No. PCT/AU00/00004 on Jan. 6, 2000, now abandoned.

(30) Foreign Application Priority Data

Jan. 13, 1999 (AU) .......................... PP8131
Nov. 9, 1999 (AU) ........................... PQ3938

(51) Int. Cl.
*A61K 47/00* (2006.01)
*A61K 9/00* (2006.01)

(52) U.S. Cl.
USPC .......................... 514/777; 514/773

(58) Field of Classification Search
CPC . A61K 2300/00; A61K 31/728; A61K 45/06; A61K 47/36; A61K 47/4823; A61K 8/64; A61K 47/42; A61K 9/0019; A61K 2800/5922; A61K 2800/91; A61K 38/1767; A61L 27/26; A61L 27/20; A61L 27/52; A61L 2430/34; A61L 27/227; C08L 5/08
USPC ........ 514/777, 773, 54, 772.1; 424/93.7, 400; 536/53

See application file for complete search history.

(56) References Cited

U.S. PATENT DOCUMENTS 4,141,973 A 2/1979 Balazs
4,160,452 A 7/1979 Theeuwes
(Continued)

FOREIGN PATENT DOCUMENTS

CA 612307 A 1/1961
CA 1227427 A1 9/1987
(Continued)

OTHER PUBLICATIONS

Anonymous. (1957). "British Standard Methods for the Determination of the Viscosity of Liquids in C.G.S. Units," *British Standards Institution*, British Standards House, London, 4 pages.

(Continued)

*Primary Examiner* — Blessing M Fubara
(74) *Attorney, Agent, or Firm* — Morrison & Foerster LLP

(57) ABSTRACT

The present invention relates to the enhancement of the efficacy of drugs, and more particularly, with overcoming the resistance of cells or organisms to drugs. In particular, the present invention provides a method for enhancing the effectiveness of a cytotoxic or anti-neoplastic agent, comprising the step of co-administering said agent with hyaluronan, wherein co-administration with hyaluronan enhances the agent's cancer cell-killing potential.

6 Claims, 25 Drawing Sheets

(56) References Cited

U.S. PATENT DOCUMENTS

| | | | |
|---|---|---|---|
| 4,256,108 A | 3/1981 | Theeuwes | |
| 4,265,874 A | 5/1981 | Bonsen et al. | |
| 4,522,811 A | 6/1985 | Eppstein et al. | |
| 4,665,107 A | 5/1987 | Micale | |
| 4,736,024 A | 4/1988 | Della Valle et al. | |
| 4,851,521 A | 7/1989 | della Valle et al. | |
| 4,965,353 A | 10/1990 | della Valle et al. | |
| 5,095,037 A | 3/1992 | Iwamitsu et al. | |
| 5,128,450 A | 7/1992 | Urdal et al. | |
| 5,202,431 A | 4/1993 | della Valle et al. | |
| 5,208,020 A | 5/1993 | Chari et al. | |
| 5,284,656 A | 2/1994 | Platz et al. | |
| 5,416,071 A | 5/1995 | Igari et al. | |
| 5,442,053 A | 8/1995 | della Valle et al. | |
| 5,475,092 A | 12/1995 | Chari et al. | |
| 5,585,499 A | 12/1996 | Chari et al. | |
| 5,662,895 A | 9/1997 | Welte et al. | |
| 5,676,964 A | 10/1997 | Della Valle et al. | |
| 5,733,891 A | 3/1998 | Akima et al. | |
| 5,744,155 A | 4/1998 | Friedman et al. | |
| 5,756,475 A | 5/1998 | Inomata et al. | |
| 5,756,537 A | 5/1998 | Gill | |
| 5,776,925 A | 7/1998 | Young et al. | |
| 5,827,834 A | 10/1998 | Falk et al. | |
| 5,830,882 A | 11/1998 | Falk et al. | |
| 5,840,673 A | 11/1998 | Buckbinder et al. | |
| 5,846,545 A | 12/1998 | Chari et al. | |
| 5,847,002 A | 12/1998 | Willoughby et al. | |
| 5,852,002 A | 12/1998 | Falk et al. | |
| 5,968,972 A | 10/1999 | Broder et al. | |
| 5,977,088 A | 11/1999 | Harper et al. | |
| 5,985,850 A * | 11/1999 | Falk et al. | 514/54 |
| 5,985,851 A | 11/1999 | Falk et al. | |
| 6,027,741 A | 2/2000 | Cialdi et al. | |
| 6,069,135 A | 5/2000 | Falk et al. | |
| 6,087,350 A | 7/2000 | Johnson et al. | |
| 6,214,860 B1 | 4/2001 | Sola et al. | |
| 6,232,301 B1 | 5/2001 | Takahashi et al. | |
| 6,242,457 B1 | 6/2001 | Penco et al. | |
| 6,299,900 B1 | 10/2001 | Reed et al. | |
| 6,475,795 B1 | 11/2002 | Turley et al. | |
| 6,552,184 B1 | 4/2003 | Pallado et al. | |
| 6,579,978 B1 | 6/2003 | Renier et al. | |
| 6,620,927 B2 | 9/2003 | Bulpitt et al. | |
| 6,831,172 B1 | 12/2004 | Barbucci et al. | |
| 7,420,033 B2 | 9/2008 | Varadhachary et al. | |
| 8,287,894 B2 | 10/2012 | Brown et al. | |
| 8,388,993 B2 | 3/2013 | Brown | |
| 8,623,354 B2 | 1/2014 | Brown et al. | |
| 2002/0015724 A1 | 2/2002 | Yang et al. | |
| 2003/0087877 A1 | 5/2003 | Calias et al. | |
| 2003/0180382 A1 | 9/2003 | Brown et al. | |
| 2005/0042303 A1 | 2/2005 | Brown et al. | |
| 2005/0267069 A1 | 12/2005 | Brown et al. | |
| 2006/0178342 A1 | 8/2006 | Brown et al. | |
| 2006/0263395 A1 | 11/2006 | Brown et al. | |
| 2007/0148734 A1 | 6/2007 | Chaudhuri et al. | |
| 2008/0063727 A1 | 3/2008 | Kim et al. | |
| 2009/0054537 A1 | 2/2009 | Brown | |
| 2009/0220497 A1 | 9/2009 | Brown et al. | |
| 2009/0306012 A1 | 12/2009 | Brown et al. | |

FOREIGN PATENT DOCUMENTS

| | | |
|---|---|---|
| CA | 2087621 A1 | 8/1994 |
| CA | 2122519 A1 | 10/1995 |
| CA | 2208924 A | 1/1999 |
| CA | 2370003 A1 | 7/2000 |
| CA | 2 387 058 A1 | 4/2001 |
| CA | 2 387 058 C | 4/2001 |
| EP | 0 138 572 A2 | 4/1985 |
| EP | 0 138 572 A3 | 4/1985 |
| EP | 0 138 572 B1 | 4/1985 |
| EP | 0 216 453 A2 | 4/1987 |
| EP | 0 216 453 A3 | 4/1987 |
| EP | 0 216 453 B1 | 4/1987 |
| EP | 0 265 116 B1 | 4/1988 |
| EP | 0 341 745 A1 | 11/1989 |
| EP | 0 341 745 B1 | 11/1989 |
| EP | 0 433 817 B1 | 6/1991 |
| EP | 0 626 863 B1 | 12/1994 |
| EP | 1 598 371 A1 | 11/2005 |
| JP | 61-000017 A | 1/1986 |
| JP | 4-504579 A | 8/1992 |
| JP | 2002-534484 A | 10/2002 |
| JP | 2003-518510 A | 6/2003 |
| WO | WO-91/04058 A2 | 4/1991 |
| WO | WO-93/16733 A1 | 9/1993 |
| WO | WO-94/15640 A1 | 7/1994 |
| WO | WO-94/23725 A1 | 10/1994 |
| WO | WO-95/30423 A2 | 11/1995 |
| WO | WO-95/30423 A3 | 11/1995 |
| WO | WO-95/30439 A2 | 11/1995 |
| WO | WO-95/30439 A3 | 11/1995 |
| WO | WO-96/06622 A1 | 3/1996 |
| WO | WO-97/20564 A1 | 6/1997 |
| WO | WO-97/40841 A1 | 11/1997 |
| WO | WO-98/17320 A1 | 4/1998 |
| WO | WO-98/23648 A1 | 6/1998 |
| WO | WO-99/02151 A1 | 1/1999 |
| WO | WO-00/20642 A1 | 4/2000 |
| WO | WO-00/41730 A1 | 7/2000 |
| WO | WO-01/36656 A2 | 5/2001 |
| WO | WO-01/47561 A1 | 7/2001 |
| WO | WO-02/05852 A1 | 1/2002 |
| WO | WO-02/090390 A1 | 11/2002 |
| WO | WO-03/018062 A1 | 3/2003 |
| WO | WO-2004/076491 A2 | 9/2004 |
| WO | WO-2006/107124 A1 | 10/2006 |
| WO | WO-2007/012133 A1 | 2/2007 |
| WO | WO-2007/028196 A1 | 3/2007 |

OTHER PUBLICATIONS

Anonymous. (Jul. 2008). "Sodium Hyaluronate," *European Pharmacopoeia* 62:3835-3837.

Avis, K.E. (1975). "Parenteral Preparations," Chapter 84 In *Remington's Pharmaceutical Sciences*, 15th Edition, Easton: Mack Publishing Company, pp. 1461-1487.

Barrow, G.M. (1979). *Physical Chemistry*, Fourth Edition, Jackson, D.C. eds., McGraw-Hill Kogakusha, Ltd., Tokyo, Japan, pp. 764-765.

Bernatchez, S.F. et al. (1994). "Sodium Hyaluronate as a Vehicle for an Improved Tolerance of 5-Fluorouracil Administered Subconjunctivally to Rabbits," *International Journal of Pharmaceutics* 106:161-166.

Bucci, L.R. et al. (2004). "Will the Real Hyaluronan Please Stand Up?" *Journal of Applied Nutrition* 54(1):10-33.

Canadian Office Action mailed Apr. 15, 2009, for CA Application No. 2,458,856, two pages.

Cunningham, D. et al. (Jul. 22, 2004). "Cetuximab Monotherapy and Cetuximab Plus Irinotecan in Irinotecan-Refractory Metastatic Colorectal Cancer," *New England Journal of Medicine* 351(4):337-345.

Deardorff, D.L. (1975). "Isotonic Solutions," Chapter 79 In *Remington's Pharmaceutical Sciences*, 15th Edition, Easton: Mack Publishing Company, pp. 1405-1412.

European Search Report mailed Sep. 26, 2005, for EP Application No. 01951219.3, four pages.

Final Office Action mailed Oct. 30, 2008, for U.S. Appl. No. 09/889,203, filed Mar. 13, 2002, 13 pages.

Final Office Action mailed May 11, 2009, for U.S. Appl. No. 11/191,407, filed Jul. 27, 2005, 12 pages.

Final Office Action mailed Mar. 12, 2010, for U.S. Appl. No. 11/198,663, filed Aug. 5, 2005, 14 pages.

Final Office Action mailed Apr. 30, 2010, for U.S. Appl. No. 11/415,612, filed May 1, 2006, 13 pages.

Final Office Action mailed Jun. 30, 2010, for U.S. Appl. No. 11/198,663, filed Aug. 5, 2005, 10 pages.

(56) References Cited

OTHER PUBLICATIONS

Final Office Action mailed Nov. 29, 2010, for U.S. Appl. No. 09/889,203, filed Mar. 13, 2002, 9 pages.
Final Office Action mailed May 2, 2011, for U.S. Appl. No. 11/191,407, filed Jul. 27, 2005, 13 pages.
Final Office Action mailed May 10, 2011, for U.S. Appl. No. 12/065,945, filed Sep. 29, 2008, 10 pages.
Final Office Action mailed on Dec. 13, 2011, for U.S. Appl. No. 11/996,733, filed on Jun. 19, 2008, thirty-four pages.
Gustafson, S. et al. (1995). "Studies on Receptors for Hyaluronan and the Turnover of Radioactively-Labelled Hyaluronan in Mice and Rats," *Second International Workshop on Hyaluronan in Drug Delivery, Round Table Series*, Willoughby, D.A. ed., Ontario, Canada, May 1-3, 1994, 36:5-7.
Hokputsa, S. et al. (2003). "Hydrodynamic Characterisation of Chemically Degraded Hyaluronic Acid," *Carbohydrate Polymers* 52:111-117.
International Search Report dated Jul. 22, 1994, for PCT Application No. PCT/CA94/00207, filed Apr. 15, 1994, three pages.
International Search Report mailed Apr. 14, 2000, for PCT Application No. PCT/AU00/00004, filed Jan. 6, 2000, six pages.
International Search Report mailed Aug. 22, 2001, for PCT Application No. PCT/AU01/00849, filed Jul. 13, 2001, three pages.
International Search Report mailed Oct. 14, 2002, for PCT Application No. PCT/AU02/01160, filed Aug. 27, 2002, three pages.
International Search Report mailed Sep. 22, 2006, for PCT Application No. PCT/AU2006/001059, filed Jul. 27, 2006, eight pages.
International Search Report mailed Oct. 17, 2006, for PCT Application No. PCT/AU2006/001293, filed Sep. 4, 2006, three pages.
Izawa, O.N. et al. (May 11, 1992). "Hyaluronic Acid Derivative Synthesis and Properties (II)—Synthesis of Hyaluronic Acid Derivative with Thymine 5FU," $41^{st}$ *Society of Polymer Science Japan Conference Proceedings, Polymer Preprints*, Japan, May 26-29, 1992, 42(3):479. (with English translation, eight pages).
Japanese Office Action mailed Jul. 7, 2009, for JP Application No. 2003-522577, with English translation, five pages.
Klein, E.S. et al. (1994). "Effects of Hyaluronic Acid on Experimental Tumor Uptake of 5-Flurouracil," *Reg. Cancer Treat*. 7:163-164.
Langer, R. (Sep. 28, 1990). "New Methods of Drug Delivery," *Science* 249:1527-1533.
Luo, Y. et al. (1999, e-pub. Jul. 27, 1999). "Synthesis and Selective Cytotoxicity of Hyaluronic Acid-Antitumor Bioconjugate," *Bioconjugate Chemistry* 10:755-763.
Maucher, A. et al. (1994). "Antitumor Activity of Coumarin and 7-Hydroxycoumarin Against 7,12-dimethylbenz[*a*]anthracene-Induced Rat Mammary Carcinomas," *J. Cancer Res. Clin. Oncol*. 120:502-504.
Mürdter, T.E. et al. (Jun. 15, 1997, e-published Jun. 1, 1997). "Enhanced Uptake of Doxorubicin into Bronchial Carcinoma: β-Glucuronidase Mediates Release of Doxorubicin froma Glucuronide Prodrug (HMR 1826) at the Tumor Site," *Cancer Research* 57:2440-2445.
Non-Final Office Action mailed May 14, 2009, for U.S. Appl. No. 11/415,612, filed May 1, 2006, four pages.
Non-Final Office Action mailed Jun. 11, 2009, for U.S. Appl. No. 11/198,663, filed Aug. 5, 2005, 14 pages.
Non-Final Office Action mailed Mar. 25, 2010, for U.S. Appl. No. 09/889,203, filed Mar. 13, 2002, 11 pages.
Non-Final Office Action mailed Oct. 8, 2010, for U.S. Appl. No. 12/065,945, filed Sep. 29, 2008, 13 pages.
Non-Final Office Action mailed, Nov. 15, 2010, for U.S. Appl. No. 11/191,407, filed Jul. 27, 2005, 11 pages.
Non-Final Office Action mailed Apr. 15, 2011, for U.S. Appl. No. 11/996,733, filed Jun. 19, 2008, 31 pages.
Non-Final Office Action mailed on Jun. 30, 2011, for U.S. Appl. No. 12/482,870, filed Jun. 11, 2009, eleven pages.
Ouchi, T. et al. (1991). "Design of Polysaccharide-5-Fluorouracil Conjugates Exhibiting Antitumour Activities," Chapter 8 In *American Chemical Society Symposium Series*, 469(Polymeric Drugs and Drug Delivery Systems):71-83.

Reynolds, J.E.F. ed. (1993). *Martindale: The Extra Pharmacopoeia*, $30^{th}$ Edition, The Pharmaceutical Press: London, England, pp. 480-482.
Rivory, L.P. et al. (1996). "Conversion of Irinotecan (CPT-11) to Its Active Metabolite, 7-Ethyl-10-hydroxycamptothecin (SN-38), by Human Liver Carboxylesterase,"*Biochemical Pharmacology* 52:1103-1111.
Rosenthal, M.A. et al. (2005, e-pub. May 9, 2005). "Phase I and Pharmacokinetic Evaluation of Intravenous Hyaluronic Acid in Combination with Doxorubicin or 5-Fluorouracil," *Chemotherapy* 51:132-141.
Rugo, H. (2004). "Bevacizumab in the Treatment of Breast Cancer: Rationale and Current Data," *The Oncologist* 9, suppl. 1, pp. 43-49.
Sakurai, K. et al. (1986). "Mucopolysaccharide-type Cancer-Metastasis Inhibitor," Japanese Kokai Patent Application No. Sho 61[1986]-17, with English translation, 36 pages.
Stern, R. et al. (2006). "Hyaluronan Fragments: An Information-Rich System," *European Journal of Cell Biology* 85:699-715.
Taguchi, T. et al. (Jan. 1994). "An Early Phase II Study of CPT-11 (irinotecan hydrochloride) in Patients with Advanced Breast Cancer," *Gan To Kagaku Ryoho* 21(1):83-90. (Abstract Only) one page.
Takasuna, K. et al. (Aug. 15, 1996). "Involvement of β-Glucuronidase in Intestinal Microflora in the Intestinal Toxicity of the Antitumor Camptothecin Derivative Irinotecan Hydrocholoride (CPT-11) in Rats," *Cancer Research* 56:3752-3757.
Tsatas, D. et al. (2002). "EGF Receptor Modifies Cellular Responses to Hyaluronan in Glioblastoma Cells Lines," *Journal of Clinical Neuroscience* 9(3):282-288.
Turley, E.A. (Mar. 1992). "Hyaluronan and Cell Locomotion," *Cancer and Metastasis Reviews* 11:21-30.
U.S. Appl. No. 09/889,203, filed Mar. 13, 2002, by Brown.
U.S. Appl. No. 12/482,870, filed Jun. 11, 2009, by Brown et al.
Wikipedia. (download on Sep. 13, 2010). "Intrinsic Viscosity," located at <http://en.wikipedia.org/wiki/Intrinsic_viscosity>, 3 pages.
Wikipedia. (download on Sep. 13, 2010). "Mark-Houwink Equation," located at <http://en.wikipedia.org/wiki/Mark%E2%80%93Houwink_equation>, 2 pages.
Wikipedia. (downloaded on Sep. 13, 2010). "Viscosity," located at <http://en.wikipedia.org/wiki/Viscosity>, 18 pages.
Yamamoto, O.H. et al. (May 11, 1992). "Synthesis of the Conjugate of Adriamycin with Oxidized Hyaluronic Acid," $42^{nd}$ *Society of Polymer Science Japan Annual Conference Proceedings, Polymer Preprints*, Japan, May 31-Jun. 2, 1993, 42(3):898. (with English translation, eight pages).
Yomota, C. (Jul. 3, 1997). "Research for Property Evaluation and Application of Hyaluronic Acid as a Biomedical Polymer," *1996 Human Science Fundamental Research Enterprise, Human Science Enterprise*, 16 pages (with English translation, 32 pages).
Zhen, Y. et al. (eds). (Nov. 2002). *Modern Biotechnological Pharmaceutics Series*, Antibody Engineering Pharmaceutics, Chemical Industry Press et al., Beijing, China, pp. 303-302, with Certified English Translation, for a total of 10 pages.
Brownlee, G.R. et al. (Apr. 2006). "Novel Formulations of Therapeutic Antibodies with Hyaluronic Acid (HA) in the Treatment of Colorectal Cancer: A Pre-clinical Evaluation," *Proceedings of the American Association for Cancer Research*, $97^{th}$ *Annual Meeting*, Washington, DC, Apr. 1-5, 2006, 47:162, Abstract No. 682.
Declaration of Samuel Simon Asculai Under § 1.132 (1996) filed on Sep. 19, 1996 for U.S. Patent No. 6,069,135 (Issued on May 30, 2000), which Matured Out of U.S. Appl. No. 07/675,908, 239 Total Pages.
Declaration of Ian Constable Under § 1.132 (1996) filed on Sep. 20, 1996 for U.S. Patent No. 6,069,135 (Issued on May 30, 2000), which Matured Out of U.S. Appl. No. 07/675,908, 45 Total Pages.
Declaration of George A. Deveber Under § 1.132 (1996) filed on Mar. 4, 1997 for U.S. Patent No. 6,069,135 (Issued on May 30, 2000), which Matured Out of U.S. Appl. No. 07/675,908, 16 Total Pages.
Declaration of Joseph Robert Emmott Fraser Under § 1.132 (1996) filed on Mar. 4, 1997 for U.S. Patent No. 6,069,135 (Issued on May 30, 2000), which Matured Out of U.S. Appl. No. 07/675,908, 62 Total Pages.

(56) References Cited

OTHER PUBLICATIONS

Declaration of Joseph Robert Emmott Fraser Under § 1.132 (1997) filed on Aug. 7, 1997 for U.S. Patent No. 6,069,135 (Issued on May 30, 2000), which Matured Out of U.S. Appl. No. 07/675,908, 71 Total Pages.

Declaration of Joseph Robert Emmott Fraser Under § 1.132 (1997) for U.S. Patent No. 5,985,850 (Issued on Nov. 16, 1999), which Matured Out of U.S. Appl. No. 08/462,154, 67 Total Pages.

Declaration of Stefan Gustafson Under § 1.132 (1996) filed on Mar. 4, 1997 for U.S. Patent No. 6,069,135 (Issued on May 30, 2000), which Matured Out of U.S. Appl. No. 07/675,908, 126 Total Pages.

Declaration of Torvard C. Laurent Under § 1.132 (1996) filed on Dec. 18, 1996 for U.S. Patent No. 6,069,135 (Issued on May 30, 2000), which Matured Out of U.S. Appl. No. 07/675,908, 46 Total Pages.

Declaration of Dr. Adrian Richard Moore Under § 1.132 (1996) filed on Mar. 4, 1997 for U.S. Patent No. 6,069,135 (Issued on May 30, 2000), which Matured Out of U.S. Appl. No. 07/675,908, 27 Total Pages.

Declaration of Sanford H. Roth Under § 1.132 (1996) filed on Mar. 4, 1997 for U.S. Patent No. 6,069,135 (Issued on May 30, 2000), which Matured Out of U.S. Appl. No. 07/675,908, 53 Total Pages.

Declaration of Eva Turley Under § 1.132 (1996) filed on Mar. 4, 1997 for U.S. Patent No. 6,069,135 (Issued on May 30, 2000), which Matured Out of U.S. Appl. No. 07/675,908, 30 Total Pages.

Declaration of Eva Turley Under § 1.132 (1997) filed on Aug. 7, 1997 for U.S. Patent No. 6,069,135 (Issued on May 30, 2000), which Matured Out of U.S. Appl. No. 07/675,908, 60 Total Pages.

Declaration of Eva Turley Under § 1.132 (1997) filed on Apr. 14, 1999 for U.S. Patent No. 5,985,850 (Issued on Nov. 16, 1999), which Matured Out of U.S. Appl. No. 08/462,154, 68 Total Pages.

Non-Final Office Action mailed, Jul. 6, 1994 for U.S. Patent No. 6,069,135 (Issued on May 30, 2000), which Matured Out of U.S. Appl. No. 07/675,908, 9 pages.

Non-Final Office Action mailed, Jun. 25, 1996 for U.S. Patent No. 5,985,850 (Issued on Nov. 16, 1999), which Matured Out of U.S. Appl. No. 08/462,154, 6 pages.

Non-Final Office Action mailed, Aug. 8, 2008, for U.S. Appl. No. 11/191,407, filed Jul. 27, 2005, 11 pages.

Non-Final Office Action mailed, Dec. 7, 2007, for U.S. Appl. No. 11/191,407, filed Jul. 27, 2005, 7 pages.

Non-Final Office Action mailed on Aug. 30, 2013, for U.S. Appl. No. 13/325,842, filed on Dec. 14, 2011, 10 pages.

Non-Final Office Action mailed Dec. 30, 2013, for U.S. Appl. No. 11/198,663, filed Aug. 5, 2005, 10 pages.

Pályi-Krekk, Z. et al. (Nov. 1, 2007). "Hyaluronan-Induced Masking of ErbB2 and CD44-Enhanced Trastuzumab Internalisation in Trastuzumab Resistant Breast Cancer," *European Journal of Cancer* 43(16):2423-2433.

Response to Non-Final Office Action submitted to the USPTO Dec. 19, 1996 for U.S. Patent No. 5,985,850 (Issued on Nov. 16, 1999), which Matured Out of U.S. Appl. No. 08/462,154, 30 pages.

Response to Non-Final Office Action submitted to the USPTO Dec. 22, 1997 for U.S. Patent No. 5,985,850 (Issued on Nov. 16, 1999), which Matured Out of U.S. Appl. No. 08/462,154, 32 pages.

Response to Non-Final Office Action submitted to the USPTO Jan. 9, 1995 for U.S. Patent No. 6,069,135 (Issued on May 30, 2000), which Matured Out of U.S. Appl. No. 07/675,908, 52 pages.

Stedman (2005). *Stedman's Medical Dictionary for the Health Professions and Nursing*, Fifth Edition, Lippincott Williams & Wilkins: Baltimore, MD, pp. 766-767.

Váradi, T. et al. (Aug. 2012; e-pub. May 4, 2012). "Binding of Trastuzumab to ErbB2 is Inhibited by a High Pericellular density of Hyaluronan," *J. Histochem. Cytochem*. 60(8):567-575.

Wikipedia (Feb. 25, 2014). "Dispersity (redirected from Polydispersity Index)," located at <http://en.wikipedia.org/wiki/Polydispersity_index>, last visited on Feb. 25, 2014, three pages.

U.S. Appl. No. 14/097,029, filed Dec. 4, 2013, by Brown et al., 95 Total Pages.

Declaration of Ian Constable Under § 1.132 (1997) filed on Mar. 4, 1997 for U.S. Patent No. 6,069,135 (Issued on May 30, 2000), which Matured Out of U.S. Appl. No. 07/675,908, 37 Total Pages.

\* cited by examiner

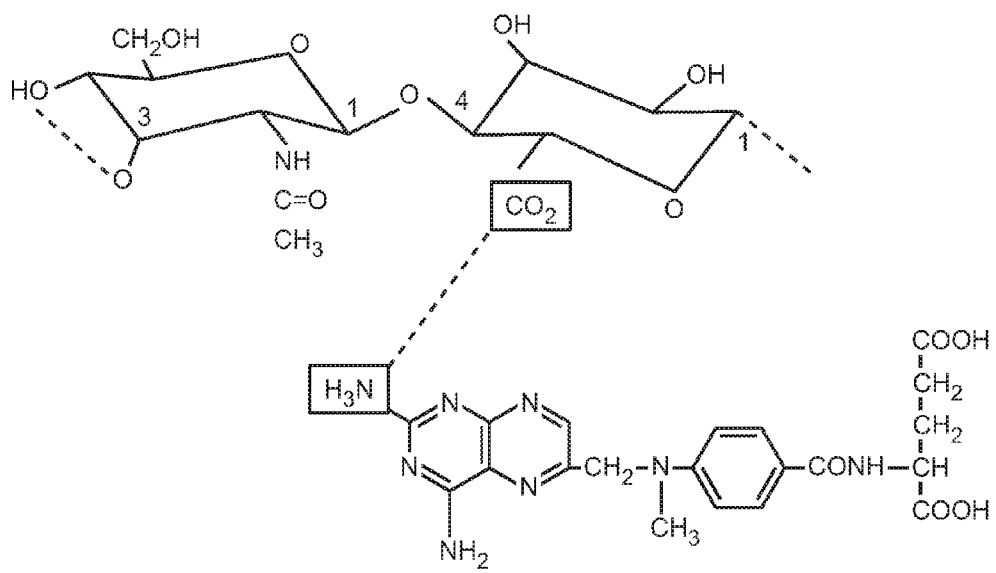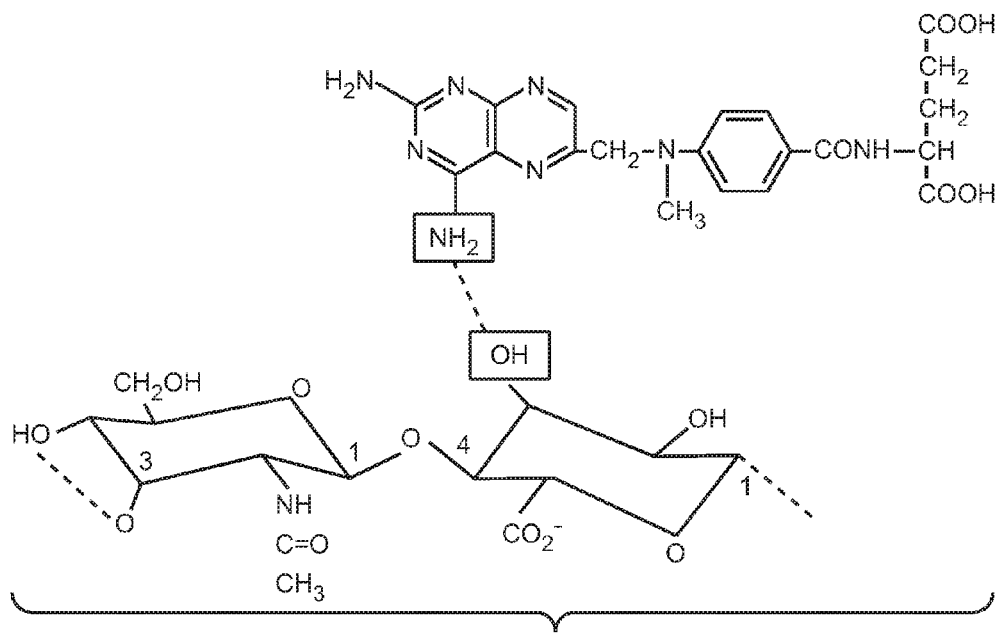
FIG. 2A iii: Hydrophobic Bonding
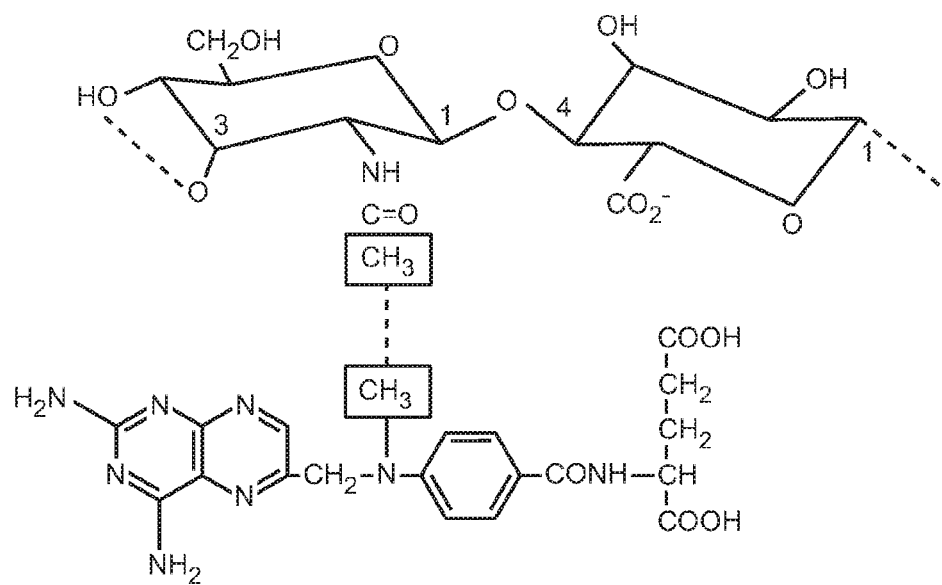
B: Entanglement of Methotrexate and Hyaluronan Molecule
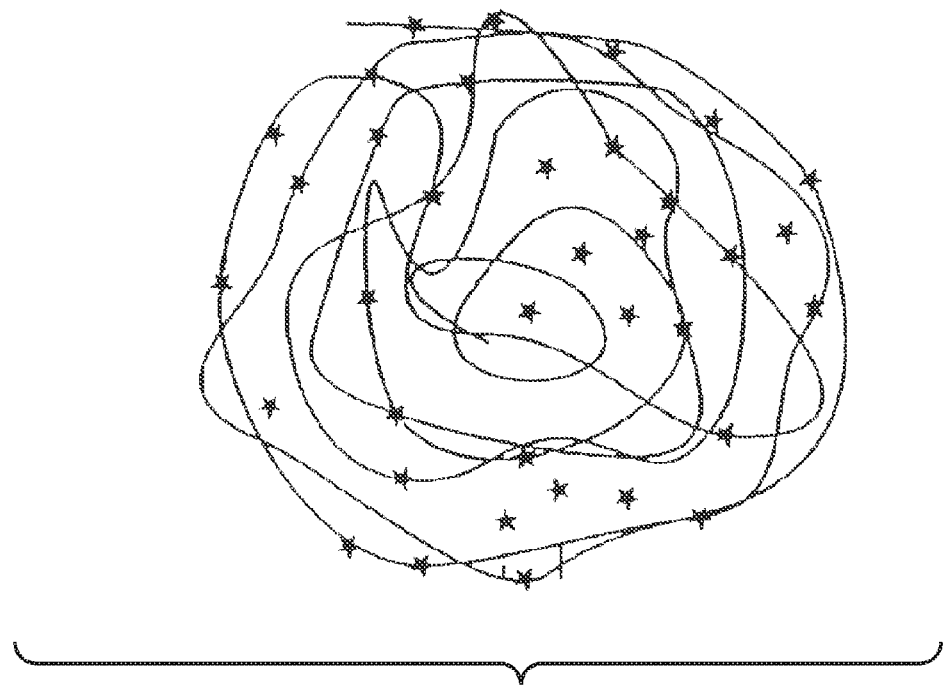
FIG. 2B

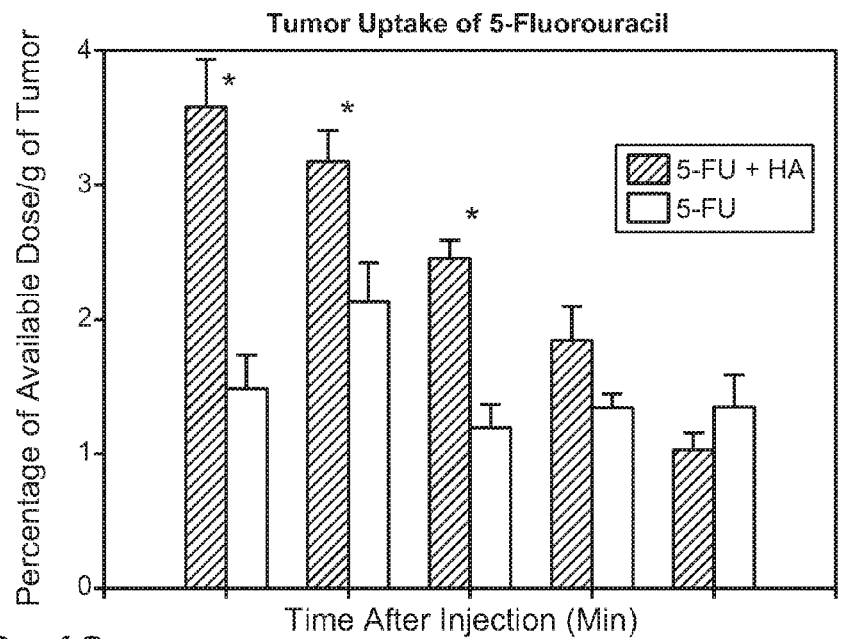
FIG. 12  * P = or < 0.001, Students t-test
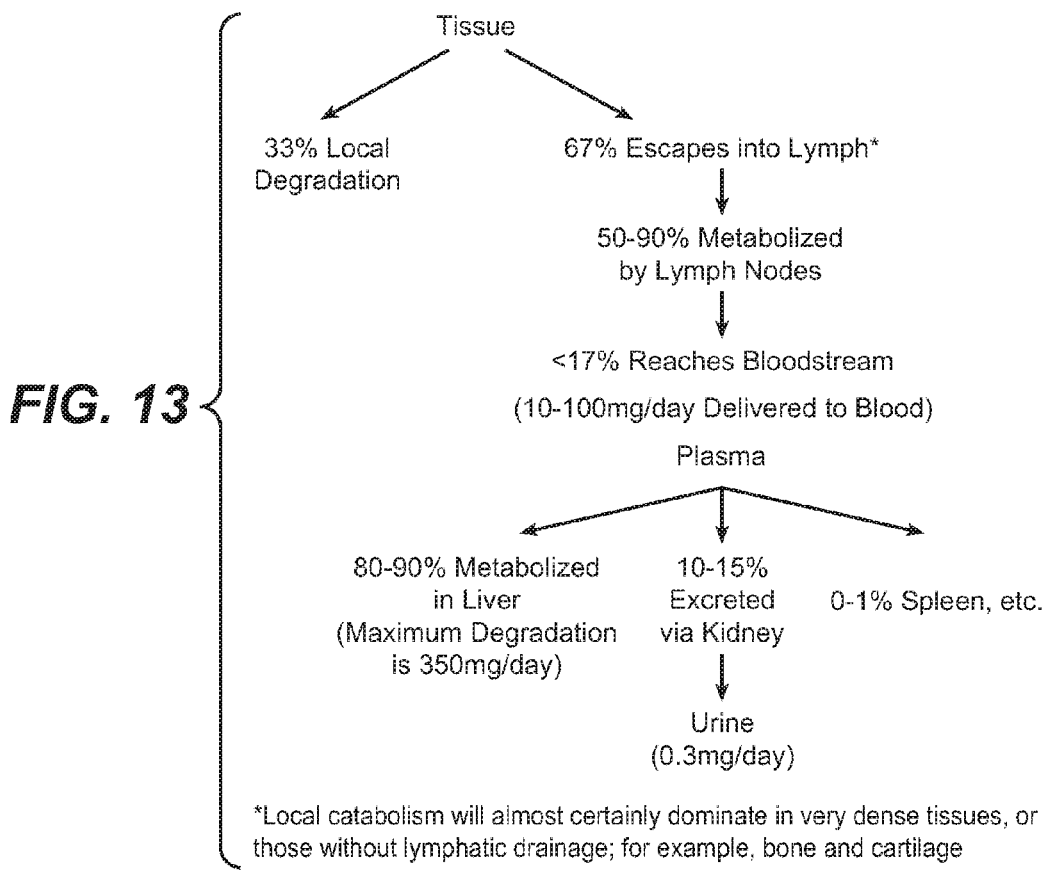
FIG. 13

COMPOSITION AND METHOD FOR THE ENHANCEMENT OF THE EFFICACY OF DRUGS

CROSS-REFERENCE TO RELATED APPLICATIONS

This application is a continuation of U.S. patent application Ser. No. 09/889,203 (abandoned), having an international filing date of Jan. 6, 2000, which is a National Phase application under 35 U.S.C. §371 of International Application No. PCT/AU00/00004, filed Jan. 6, 2000, which claims priority benefit of Australian Patent Application Nos. PP 8131 filed Jan. 13, 1999 and PQ 3938, filed Nov. 9, 1999. The content of these applications are hereby incorporated by reference in their entirety.

FIELD OF THE INVENTION

The present invention relates to the enhancement of the efficacy of drugs, and more particularly, with overcoming the resistance of cells or organisms to drugs.

BACKGROUND TO THE INVENTION

The clinical usefulness of any chemotherapeutic agent or drug can be severely affected by the emergence of cellular resistance to that drug. Accordingly, a significant amount of research has been conducted in an attempt to elucidate the cellular mechanisms involved with resistance to drugs, as well as methods for overcoming such resistance. To date a number of putative cellular mechanisms involved in drug resistance have been proposed. These include:

(i) altered metabolism of the drugs, which could include decreased activation or increased deactivation;

(ii) impermeability of the target cell or organism to the active compound;

(iii) altered specificity of an inhibited enzyme;

(iv) increased production of a target molecule;

(v) increased repair of cytotoxic lesions; and (vi) bypassing of an inhibited reaction by alternative biochemical pathways.

The cellular mechanisms involved in drug resistance are complex, and consequently there has been little progress in the development of generally applicable methods for overcoming drug resistance problems. A further complicating factor is that while drug resistance is a problem associated with nearly all chemotherapeutic applications, it is more often associated with diseases which require on-going and prolonged treatment with a number of concurrent drugs.

In cancer treatment, for example, impermeability of the cancer cells to the active compound is often observed. Moreover, it is often found that resistance to one drug may confer resistance to other biochemically distinct drugs. This has been termed multidrug resistance. Drugs that are typically affected by the multidrug resistance problem include doxorubicin, vincristine, vinblastine, colchicine and actinomycin D. In at least some cases, multidrug resistance is a complex phenotype that has been linked to a high level of expression of a cell membrane drug efflux transporter called MdrI protein, also known as P-glycoprotein. This membrane "pump" has broad specificity, and acts to remove from the cell a wide variety of chemically unrelated toxins (see Endicott et al., 1989).

Recently, a similar mechanism of broad-spectrum drug resistance has been reported for certain microorganisms. These results indicate the existence of bacterial efflux systems of extremely broad substrate specificity that are similar to the multidrug resistance pump of mammalian cells (see Nikaido, 1993).

Substances which reverse multidrug resistance are known as resistance modification agents (RMAs), and are of importance in potentiating the cytotoxicity of chemotherapeutic agents to which a human cancer has become resistant. Although many agents have been identified as RMAs in vitro, a large proportion of these have little or no therapeutic potential because of high toxicity in vivo at the doses required to reverse multidrug resistance. For example, metabolic poisons, such as azide, are able to reverse multidrug resistance in vitro, but have no usefulness in vivo. Most other highly effective RMAs, such as PSC833, appear to work as competitive antagonists of a drug-binding site on the MdrI protein. Many of these agents also have toxicity that limits their usefulness in vivo. Consequently, there is a need to develop alternate pharmacological strategies for reversing multidrug resistance.

In an attempt to overcome poor tumour uptake of anti-neoplastic drugs and reduce systemic toxicity (Singh et al., 1991), investigators have attempted to target anti-neoplastic drugs such as methotrexate (MTX) to the location of malignant tissue. Several studies have already attempted to target chemotherapeutic agents to tumours by linking drugs to polymers selected for their affinity to tumours (Hudecz et al., 1993; Klein et al., 1994; Akima et al., 1996). However, while these polymers may help to deliver active agents to their target tissues, they do not necessarily overcome the drug resistance problem.

One polymer which has been proposed as a tumour targeting agent is hyaluronan (HA). HA, also known as hyaluronic acid, is a naturally occurring polysaccharide comprising linear-chain polymers, which is found ubiquitously throughout the animal kingdom. HA is highly water-soluble, making it an ideal drug delivery vehicle for biological systems.

The applicants have now surprisingly found that HA exhibits unique structural and physicochemical properties which not only enhance its usefulness as a drug carrier, but also aid in overcoming drug resistance. In high concentrations of ~1 g/L, HA adopts a stiffened random coil configuration that occupies an exceptional volume relative to molecule mass (Laurent, 1970), and at this level or below, it forms loose links to macromolecular networks (FIG. 1). While not wishing to be bound by any particular theory, we consider that, based on the physical characteristics of HA, the mechanism of interaction between polysaccharide and agents such as methotrexate, may take one or both of two forms:

(i) Chemical Interaction (FIG. 2A).

Ionic bonding could occur between the MTX amine groups and the HA carboxyl groups, but such an interaction could cause precipitation. Another possible interaction is via hydrogen bonding between available amine groups on the drug and hydroxyl groups of the HA, but this is unlikely because methotrexate is relatively insoluble in water; therefore if this were to occur it would be a very weak interaction. The most likely bonding between MTX and HA would be via hydrophobic interactions between MTX's numerous hydrophobic groups and the hydrophobic patches in the secondary structure of HA (Scott et al., 1989).

(ii) Molecular Association.

Where MTX is merely "mixed" in HA gel (FIG. 2B) with no specific chemical bond formation, MTX could become entrapped within the 3-dimensional meshwork formed by higher concentrations of HA (Mikelsaar and Scott, 1994), so that the drug simply diffuses from the HA after administration. If HA is rapidly taken up and bound by specific cell receptors, the drug will be released in higher concentration at these points eg. lymph nodes, liver, bone marrow, tumour cells with HA receptors.

While again not wishing to be bound by any particular theory, one mechanism by which HA helps to target active agents may be via the characteristic over-expression of HA receptors in several tumour types (Stamenkovic et al., 1991; Wang et al., 1998). The HA receptors CD44, Receptor for Hyaluronan Mediated Motility (RHAMM) and ICAM-1, have been linked to tumour genesis (Bartolazzi et al., 1994) and progression (Günthert 1993; Arch et al., 1992). RHAMM is a major factor in mediating tumour cell motility and invasion (Hardwick et al., 1992). It has been demonstrated that RHAMM is required for H-ras transformation of fibroblasts (Hall et al., 1995), which would make this receptor a potential participant in tumour formation and growth. ICAM-1, a receptor tentatively linked to HA metabolism (McCourt et al., 1994), is highly expressed in transformed tissues such as mouse mastocytomas (Gustafson et al., 1995a) and in the stroma and clusters of tumour cells of human breast carcinomas (Ogawa et al., 1998).

Increased expression of HA receptors on tumour cells provides a rationale for attempting the incorporation of HA into chemotherapeutic treatment regimens. However, the very limited data obtained to date actually teach away from the presently claimed process. For example, limited success has been obtained by chemically complexing HA to mitomycin C and epirubicin; investigators were able to inhibit colon carcinoma growth by 0.8-25% (Akima et al., 1996). Klein and colleagues (1994) reported an increased uptake of the drug into implanted rat mammary and Fischer bladder carcinomas was achieved by merely mixing HA with 5-FU. Mouse mastocytomas were also demonstrated to have an affinity for intravenously-injected HA (Gustafson et al., 1995b).

However, while some of the HA research has shown that HA can be used as a drug carrier, none of this research has shown that HA is capable of overcoming cellular resistance to drugs.

SUMMARY OF THE INVENTION

The present invention provides a method for enhancing the effectiveness of a cytotoxic or anti-neoplastic agent, comprising the step of co-administering said agent with hyaluronan, wherein co-administration with hyaluronan enhances the agent's cancer cell-killing potential.

Typically, co-administration of a cytotoxic or anti-neoplastic agent with hyaluronan enhances its cancer cell-killing potential. That is, cancer cells that are normally resistant to the drug become susceptible to it.

Preferably, the agent is methotrexate, paclitaxel (TAXOL) or 5-fluorouracil (5-FU).

According to a second aspect of the present invention there is provided a cytotoxic or anti-neoplastic pharmaceutical composition comprising hyaluronan and a cytotoxic or anti-neoplastic agent. Optionally, conventional pharmaceutical adjuncts may be included in the pharmaceutical composition.

Typically said drug is entrained within or bound to hyaluronan.

According to a third aspect of the present invention there is provided a method of enhancing the effectiveness of a cytotoxic or anti-neoplastic agent, comprising the step of administration of a pharmaceutical composition comprising hyaluronan and said agent.

While not wishing to be bound by theory, it is believed possible mechanisms for overcoming drug resistance are:

1. Hyaluronan binds to receptors on the resistant cell or enters the cell via bulk endocytosis, resulting in the entrained or bound agent being delivered into the cell, allowing it to become therapeutically active.
2. Hyaluronan binds to the surface of the resistant cell, where the entrained or bound agent diffuses from the hyaluronan meshwork into the cell, resulting in the agent being delivered to the resistant cell.
3. Hyaluronan and other mucopolysaccharides adopt a coiled configuration that entrains the agent, and may also bind a variety of agents.

Accordingly in a fourth aspect, the present invention provides a method of reducing or overcoming drug-resistance, comprising the step of co-administering a cytotoxic or anti-neoplastic agent with a mucopolysaccharide capable of entraining and/or binding said agent and capable of binding to receptors on the resistant cell or entering the cell via bulk endocytosis, wherein said agent is delivered into the cell, thereby allowing it to become therapeutically active.

While not wishing to be bound by theory, it may also be that a combination of hyaluronan with a drug results in the drug being retained in the cell for a longer period, allowing a prolonged release and more time for the drug to exert its pharmacological effect.

Accordingly, in the fifth aspect of the present invention there is provided a method for enhancing the effectiveness of a drug, comprising the step of co-administering said drug with a mucopolysaccharide which associates with said drug in such a manner that said drug is retained in the cell for a longer period than if said drug were administered alone. For example, where the drug is a cytotoxic drug, the drug will be retained in the cell for a longer period, allowing a prolonged release and more time to exert its toxic effects.

According to a sixth aspect of the present invention there is provided a method for the treatment of a drug-resistant disease, comprising the step of co-administering hyaluronan and a drug to a patient in need of such treatment.

In one embodiment, this aspect of the invention provides a method for the treatment of a drug resistant disease, comprising the step of administering a composition comprising hyaluronan and a drug to a patient in need of such treatment.

In particular, the method for treatment of a drug resistant disease is applicable to a patient with a drug resistant cancer. Preferably, the cancer is resistant to methotrexate or 5-FU.

More preferably, said drug resistance is multidrug resistance.

According to an seventh aspect of the present invention there is provided a method for the treatment of cancer, comprising the step of co-administering a drug and a mucopolysaccharide capable of entraining or binding said drug and/or associating with said drug in such a manner that said drug is retained in a cancer cell for a longer period than if said drug were administered alone.

According to an eighth aspect of the present invention there is provided a method for the reduction of gastrointestinal toxicity of a drug, comprising the step of co-administering a drug and a mucopolysaccharide capable of entraining or binding said drug and/or associating with said drug in such a manner that said drug has reduced gastrointestinal toxicity.

Throughout the description and claims of this specification, the word "comprise" and variations of the word, such as "comprising" and "comprises", means "including but not limited to" and is not intended to exclude other additives, components, integers or steps.

BRIEF DESCRIPTION OF THE FIGURES

FIG. 2A shows the possible molecular interactions between methotrexate and HA. These include (i) ionic bonding, (ii) hydrogen bonding or (iii) hydrophobic bonding.

FIG. 2B is a diagrammatic representation of the entanglement of methotrexate in HA. At higher concentrations HA forms a 3-dimensional meshwork which is represented by the large coiled molecule. (*) represents the methotrexate which has a molecular weight of only 454D, and is easily entrained in the 400-900 kD HA molecule.

FIG. 12 shows 5-FU targeting of human breast cancer tumours using HA as a carrier.

FIG. 13 shows elimination pathways of HA in humans.

ABBREVIATIONS

Figure 1:
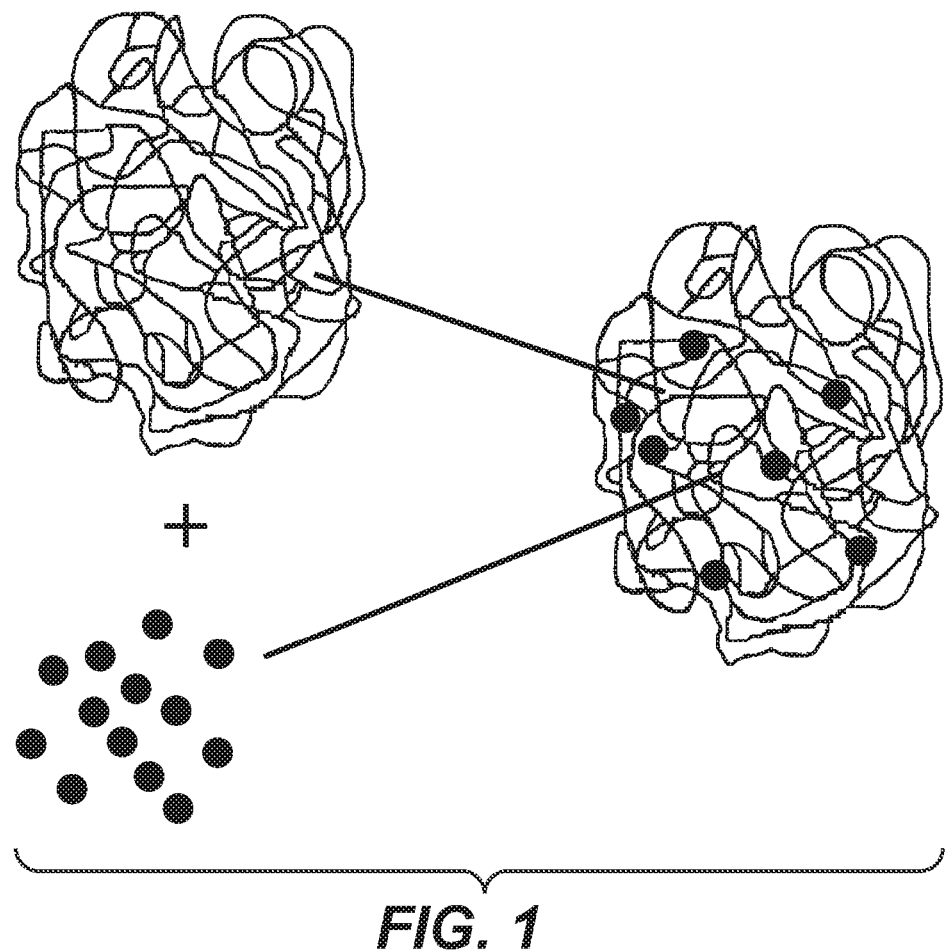
FIG. 1 shows that in higher concentrations HA forms a three-dimensional meshwork which is capable of entraining small molecules such as methotrexate. The HA/drug targeting of pathological sites is accomplished by the HA rapidly binding to specific cell receptors, followed by diffusion of the drug from the HA, and/or co-internalization of both the HA and drug via HA and/or drug receptors.

BSA Bovine serum albumin
Ci Curies
CMF Cyclophosphamide, Methotrexate and 5-Fluorouacil
Cyc Cyclophosphamide
DNA Deoxyribonucleic acid
Dpm Deteriorations per minute
DTTP Deoxythymidine triphosphate
ECM Extracellular matrix
EDTA Ethylenediaminetetraacetic acid
ELISA Enzyme linked immunosorbent assay
FCS Foetal calf serum
5-FU 5-fluorouracil
GAG Glycosaminoglycan
GlcNAc N-acetyl glucosamine
GlcUA Glucuronic acid
HA Hyaluronan/Hyaluronic acid
HABP Hyaluronan binding protein
HAase Hyaluronidase
HBSS Hanks balanced salt solution
HRP Horse radical peroxidase
h hour
$K_{av}$ available volume of distribution within the gel
l Liter
min minute
PBS Phosphate buffered saline
PM Plasma membrane
RHAMM Receptor for HA-mediated motility
RMCa Rat mammary carcinoma
RNA Ribonucleic acid
RT Room temperature
S-phase Synthesis phase
S.D. Standard deviation
SEM Standard error of the mean
$V_e$ volume of elution $V_o$ void volume
$V_t$ total volume
TGD Tumour growth delay
TDT Tumour Doubling Ti

DETAILED DESCRIPTION OF THE INVENTION

The invention will now be further described by way of reference only to the following non-limiting examples. It should be understood, however, that the examples following are illustrative only, and should not be taken in any way as a restriction on the generality of the invention described above. In particular, while the invention is described in detail in relation to cancer, it will be clearly understood that the findings herein are not limited to treatment of cancer. For example, cytotoxic agents may be used for treatment of other conditions; methotrexate is widely used for treatment of severe rheumatoid arthritis.

Example 1

Validation of Human Breast Cancer Tumours in Nude Mice and Identification of Hyaluronan Receptors on the Breast Tumours in Situ To establish an appropriate animal model for human breast cancer, it was necessary to perform pathological testing. For a tumour to be physiologically viable neovascularization is essential, because the capillary network supplies nutrients to the tumour. The presence of vascularisation, ductal invasion, necrosis, apoptosis, a high mitotic index and nuclear abnormalities are all characteristic of breast carcinoma.

The human breast carcinoma cell line MDA-MB-468 (American Tissue Culture Collection, Rockville, U.S.A) was selected on the basis of its expression of the HA receptors, CD44, RHAMM and ICAM-1. Cells were routinely grown and subcultured as a monolayer in 175 cm$^2$ culture flasks in Leibovitz L-15 Medium supplemented with 10% foetal calf serum (FCS) and 10 µg/ml gentamicin. For injection into mice cells were grown to 100% confluency, trypsinised in a 0.05% trypsin/0.01% EDTA solution, washed twice by centrifugation in a Beckman TJ-6 bench centrifuge (Beckman, Australia) at 400 $g_{av}$ for 10 min, counted using a Model-ZM Coulter counter (Coulter Electronics, England), and resuspended in serum-free Leibovitz L-15 medium at 1×10$^8$ cell/ml.

85 athymic Balb/c/WEHI nude female mice (Walter and Eliza Hall Institute of Medical Research, Melbourne, Australia), 6 to 8 weeks old, were maintained under specific pathogen-free conditions, with sterilised food and water available ad libitum. Ten million MDA-MB 468 cells were prepared as described above, and directly injected into the fat pad under the nipple of each mouse. Tumour growth was observed in 96% of mice. When the tumour growth was visually detectable, the tumour progression was monitored by weekly measurements of the tumour volume. Tumour volumes were calculated from 3 perpendicular diameters using the equation;

$$V=(1/6)p(d_1 d_2 d_3)$$

where:
V is tumour volume (in mm$^3$),
$d_1$ is the first diameter of the tumour (in mm),
$d_2$ is the second diameter of the tumour (in mm), and
$d_3$ is the third diameter of the tumour (in mm) (Lamszus et al, 1997).
Eight weeks after tumour inoculation the mean tumour size was 482.2 mm$^3$ (SEM, 39.8 mm$^3$).

Approximately 8 weeks after tumour induction two tumour-bearing mice were given a lethal dose of Nembutal. Within 3 min of killing the mice, tumours were surgically removed and immediately fixed in 10% buffered formalin for 12 hours. The fixed tumour was dehydrated overnight in a series of 70-100% ethanol washes, followed by paraffin embedding from which 2-4 µm sections were cut. The sections were placed on slides, dewaxed, and brought to water. Slides were washed 3×5 min in phosphate-buffered saline (PBS). Heterophile proteins were blocked by incubation with 10% foetal calf serum for 10 min, followed by a PBS rinse. The detection antibodies were applied for 60 min at room temperature (RT). The antisera or antibodies were directed against RHAMM (Applied Bioligands Corporation (Manitoba, Canada), ICAM-1, CD44v6, CD44v10, total CD44H, and CAE. All other detection antibodies were purchased from Zymed (California, U.S.A). The slides were washed 3×5 min in PBS and endogenous peroxidase activity blocked by immersion in 0.3% $H_2O_2$/methanol for 20 min. Following a further PBS wash, peroxidase-conjugated pig anti-rabbit secondary antiserum (Dako, Denmark) was applied for 60 min at RT, followed by 3×5 min wash in PBS. Sigma Fast DAB (3,3'-Diaminobenzidine, Sigma, St. Louis, U.S.A) tablets were prepared according to the manufacturer's instructions and the DAB solution was applied for 5-10 min at RT. The slides were washed in tap water for 10 min, counterstained with haematoxylin, dehydrated and mounted.

Figure 3A:
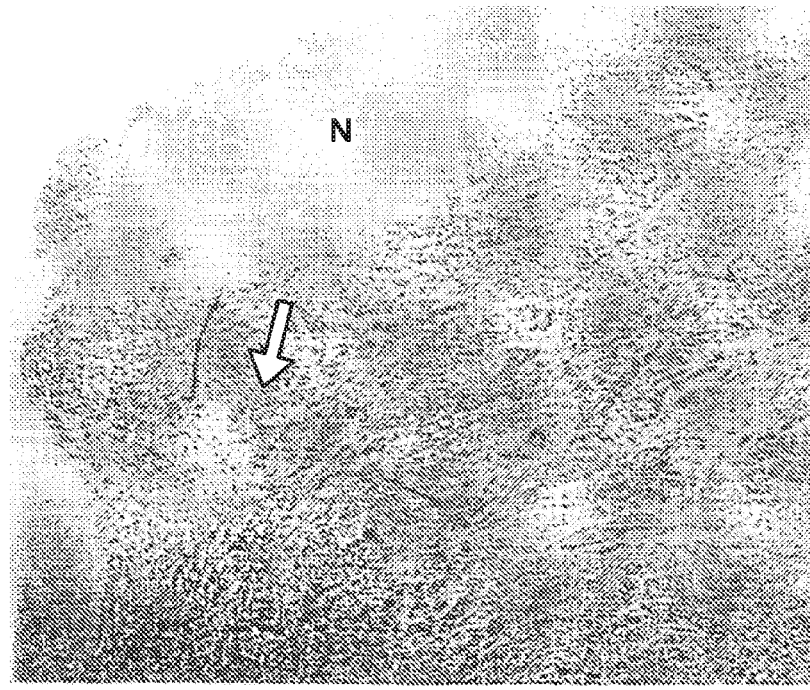
FIG. 3 shows the general pathology of human breast cancer tumours grown in nude mice. Panel A shows the general morphology of a grade II-III human tumour. Panel B shows a micrograph of another section of the tumour exhibited in FIG. 3A. This section shows the surrounding mouse muscle (M), tumour capsule (C), necrotic areas of the tumour (N), infiltrating tumour (T) and (→) indicates a common phenomenon known as "Indian files", in which carcinoma cells line up in files which are often associated with an infiltrating carcinoma (Carter, 1990).
Figure 3B:
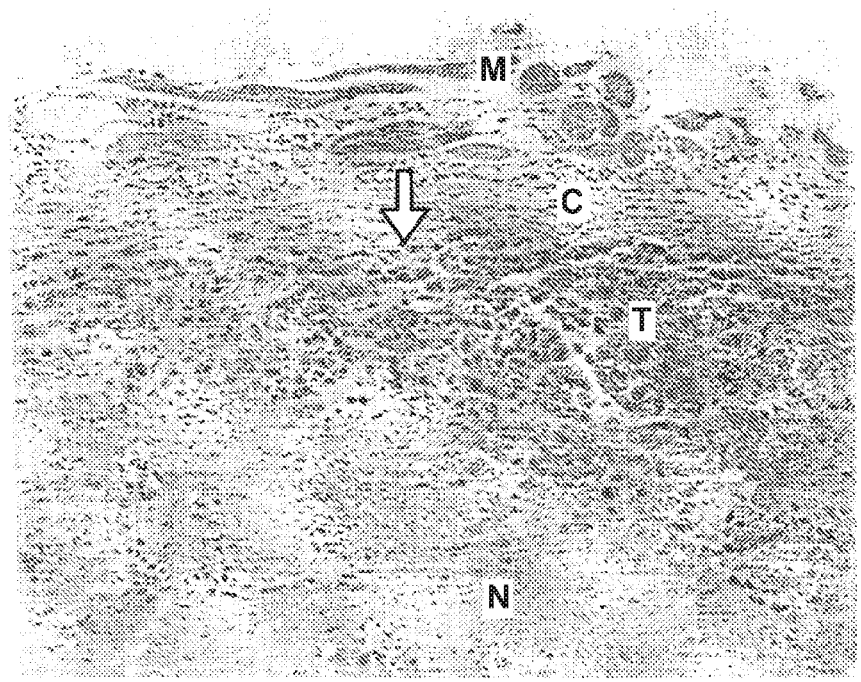
Figure 4A:
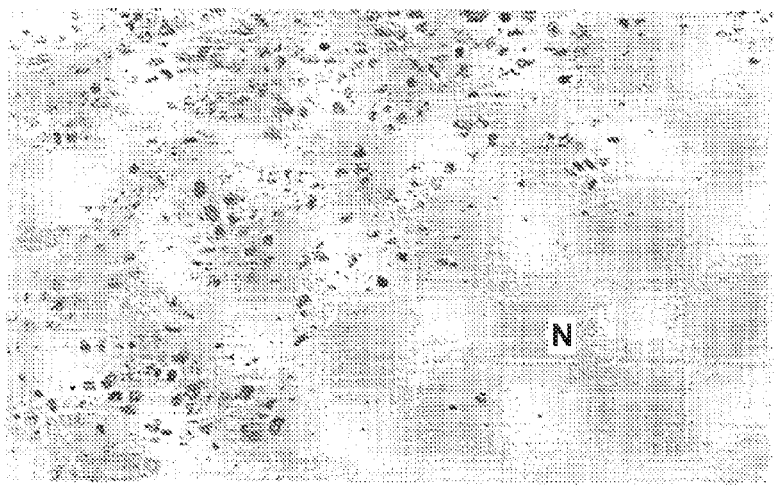
FIG. 4 shows the classical pathological features of breast malignancy. Panel A shows a section of characteristic infiltrating duct carcinoma with large areas of necrosis (N), indicating the more aggressive course of the tumour. Panel B shows the presence of blood cells (→), demonstrating that the tumour is vascularized and therefore viable. In close proximity to the blood vessel there are a few observed ducts (D). Panel C shows cells, labelled as (A), undergoing apoptosis, as indicated by the nuclear fragmentation.
Figure 4B:
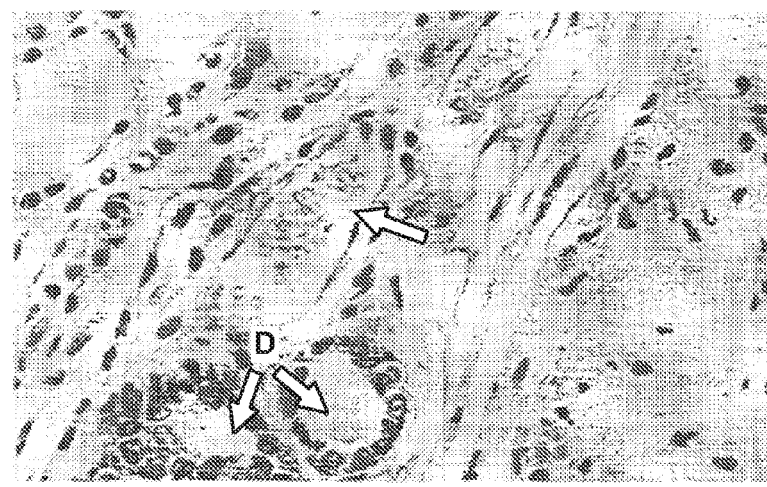
Figure 4C:
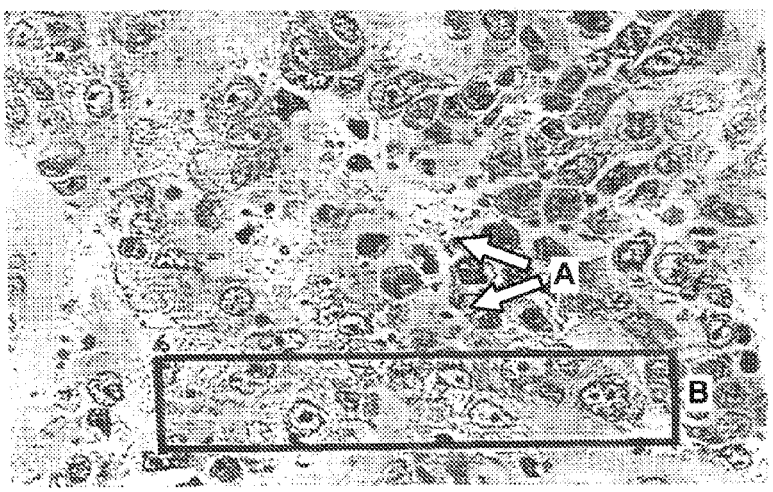

Examination of the haematoxylin and eosin-stained breast tumour sections demonstrated all of the usual features associated with viable tumours, as shown in FIGS. 3 and 4, confirming that the animal host successfully maintained a grade II human breast carcinoma. There are several features which are characteristic of malignancy. The section of the slides labelled (B) displays these features. All of the pathological features of malignancy observed are in section (B), ie
i) high nuclear/cytoplasmic ratios
ii) angular chromatin and nucleoli
iii) irregular nuclear membrane It was concluded that a grade II-III level tumour was capable of being supported in the nude mouse model. A grade II-III level tumour generally gives a prognostic survival rate of about 47% (Bloom and Richardson, 1957). A grade II-II level tumour is characterised by:
i) moderate nuclear pleomorphism, hyperchromatin, and mitotic activity, features observed throughout the displayed section of tumour; and
ii) little or no duct formation.

Large areas of necrosis (N) can be correlated with the tumour spread, which suggests a more aggressive invasive course (Carter, 1990). The infiltrating edge of the tumour is indicated by ( ).

Figure 5B:
FIG. 5 shows the immunohistochemical identification of HA receptors on the human breast cancer tumours grown in nude mice. Panel A shows carcinoembryonic antigen (CEA) localisation in tumour. Panel B shows RHAMM expression on human breast carcinoma. Panel C shows ICAM-1 expression on human breast carcinoma. The localisation of HA receptor, ICAM-1 is primarily around endothelial tissue (→). Panel D shows CD44 expression on human breast carcinoma. CD44H was detected on approximately 95% of the tumour cells. H: cells of human origin; M: cells of murine origin.
Figure 5D:
Figure 5A:
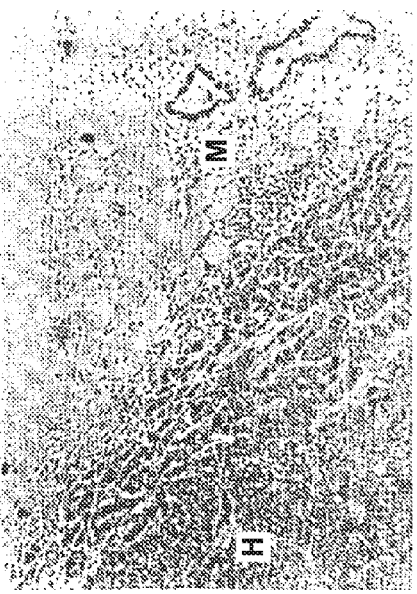
Figure 5C:
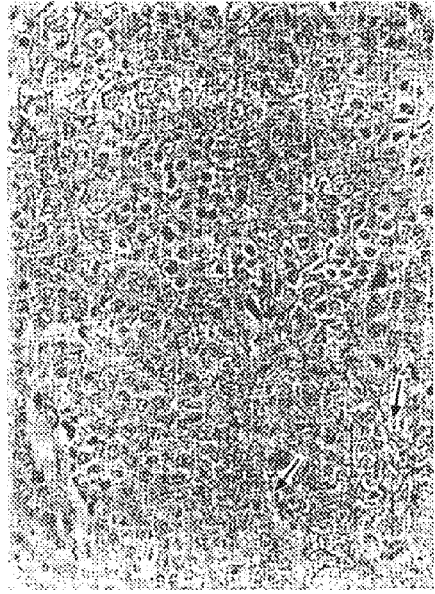

A major aim of this experiment was validation that the histological and cytological behaviour of the tumours established in these mice were comparable to those of such tumours in their natural human hosts. In achieving this aim we have also shown that the tumour cells in the mice are of human origin and that they express highly relevant HA receptors such as RHAMM, CD44 and putative ICAM-1. Since it was hypothesised that tumour targeting could occur via receptor-mediated internalisation or binding, it was necessary to confirm the expression of HA receptors, ICAM-1, CD44 and RHAMM. FIGS. 5B-D demonstrates that all these receptors were present. Table 1 lists the degree of receptor expression on the two tumours tested.

TABLE 1

Expression Of Hyaluronan Receptors
On Human Breast Tumour Xenografts

| HA receptor | Function | Distribution on tumour | % epitope expression on tumour |
|---|---|---|---|
| CD44H | Isoform which predominantly binds and internalises HA (Culty et al., 1992) | Expressed on all cells with exception of some stromal cells | ++++ |
| CD44v6 | Role in cancer unknown, but is often used as a prognostic factor. The higher the expression, the lower the survival probability (Friedrichs et al., 1995) | | + |
| CD44v3 | Often over-expressed in breast carcinoma (Friedrichs et al., 1995) | | − |
| RHAMM | Required for transformation and tumour cell invasion (Hall et al., 1995) | Groups of infiltrating tumour cells, with high expression on cells surrounding necrotic areas | +++ |
| ICAM-1 | Binds and internalises HA, putative metabolic receptor (McCourt et al., 1994) | Present on stromal cells | ++ |
| CEA | A fetal antigen expressed on malignant cells (Haskell, 1990) | Present on all tumour cells | ++++ |

The rating index for the percentage of epitope expression on the tumour was quantitated as:
0% −
1-25% +
26-50% ++
51-75% +++
76-100% ++++

The human origin of the tumour cells was confirmed by staining the tumour and surrounding tissue with a human-specific cancer marker. The presence of CEA clearly demonstrated that the tumour was human, while being maintained by the cardiovascular system of the murine host (FIG. 5A). The polyclonal CEA antisera was selected, since it reacts exclusively with human CEA. This micrograph demonstrates that the tumour was entirely of human origin (H), as shown by the brown staining. The surrounding tumour capsule and adipose tissue is definitely of mouse origin, as indicated by the lack of staining with the antisera (M). The brown staining demonstrates the high expression of RHAMM on the tumour cells. The greatest intensity of staining can be noted on the areas surrounding tissue necrosis and tumour infiltration.

Example 2

Preparation and Injection of
Methotrexate/Hyaluronan Drug Combinations

Having established the usefulness of the nude mouse model, it could now be used to test the effectiveness of a HA/MTX preparation.

A stock solution of MTX was prepared by dissolving powdered MTX in 0.5% w/v sodium carbonate (pH 9), and brought to a concentration of 24.5 mg/ml with 0.9% w/v NaCl. The stock solution was filtered through a 0.22 µm filter to ensure sterility before addition of [$^3$H]methotrexate and dilution to injection concentration with injection-grade sodium chloride. Comparative data on the pharmacokinetics of MTX have already been published for the nude mouse and humans (Inaba et al, 1988), and were utilised in the design of this study, to simulate human therapeutic doses as closely as possible. Individual injections were prepared according to individual mouse body masses, with the aim of delivering 15 mg/kg MTX in 50 µl (equivalent to a human therapeutic dose of 0.42 mg/kg for a mean body weight of 60 kg; Inaba et al, 1988).

Desiccated HA (modal Mr $8.9 \times 10^5$ Da) was added to a portion of the 24.5 mg/ml MTX stock solution and dissolved overnight with vortexing, to give a final concentration of 21 mg/ml. To ensure sterility gentamicin was added to a concentration of 50 µg/ml and incubated overnight at 4° C. Following the addition of [$^3$H]methotrexate the HA/MTX stock mixture was diluted to injection concentration with injection grade sodium chloride. Injections were individually made according to mouse body masses, to deliver 15 mg/kg MTX and 12.5 mg/kg HA in 50 µl. With this quantity of HA injected into the body, saturation kinetics would be observed for the period of the experiment (Fraser et al., 1983).

Figure 6:
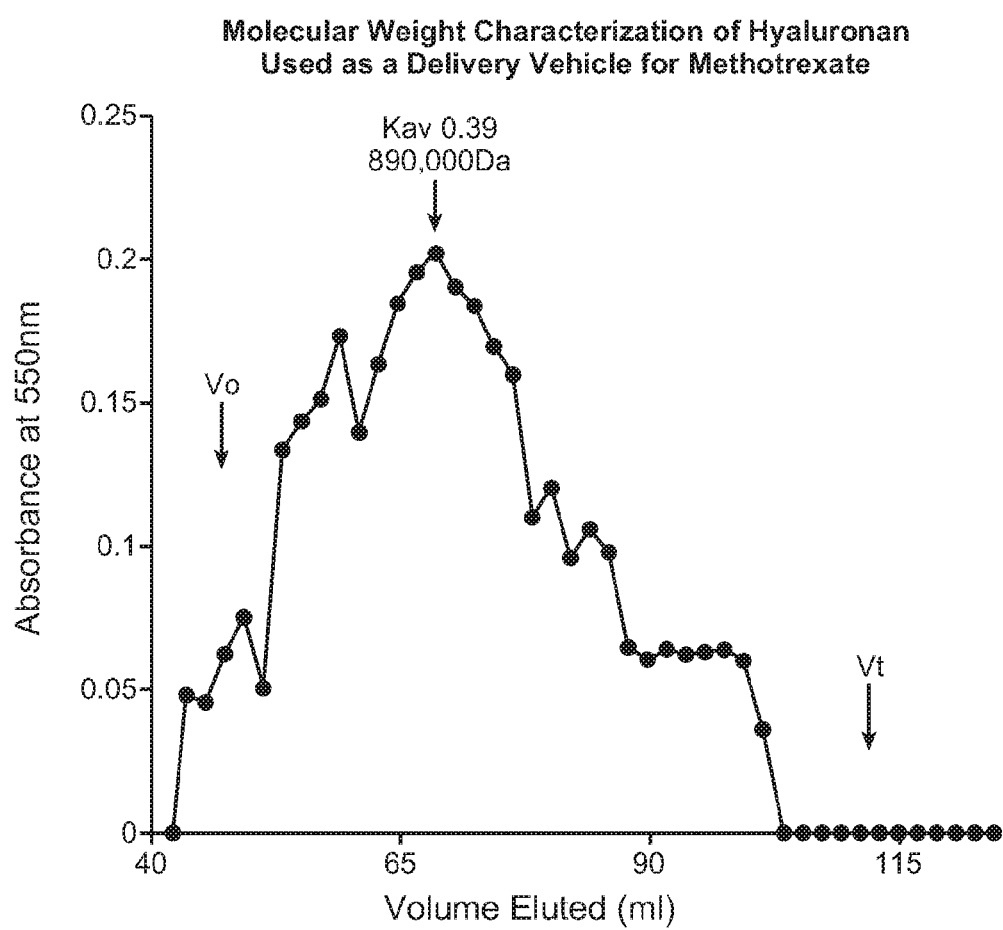
FIG. 6 shows the results of molecular weight analysis of hyaluronan used as a carrier for the methotrexate targeting of tumours.

To ensure that the HA had maintained its molecular weight during the preparation of the methotrexate/HA injection mixture, the injection solution was analysed on a Sephacryl S-1000 size exclusion gel (Pharmacia, Uppsala, Sweden) with column specifications of 1.6 cm×70 cm, sample size 2 ml, flow rate 18 ml/h and 2 ml fraction size. FIG. 6 shows that HA retained its molecular weight during the mixing procedure.

Mice were randomly divided into 2 groups of 40 animals. Group I received MTX only, and Group 2 received MTX/HA combination therapy. Animals were individually placed in an injection box, and the injections were administered via the tail vein. Tritiated methotrexate (mean injected disintegration's per minute (dpm)±standard error of the mean (SEM): 19,159, 146±1,336,819) contained within 15 mg/kg MTX±12.5 mg/kg HA was delivered in each injection. Mice were individually housed in soft, non-wettable plastic enclosures so urine could be collected. At 30 min, 1 h, 2 h, 4 h or 8 h after injection mice were anaesthetised by 0.1 ml intra-peritoneal injection of Nembutal (Glaxo, Australia Pty. Ltd., Melbourne, Australia), and blood was collected from the heart or great vessels using a needle and syringe. After blood collection the animals were killed by cervical dislocation.

Blood was delivered into EDTA-coated glass tubes and plasma was prepared by centrifugation at 14,000 $g_{av}$ for 10 min. Radioactivity was counted in 50 µl aliquot's after decolourisation with 100 µl of 30% v/v hydrogen peroxide and the addition of 3 ml HiSafeII scintillant. To overcome chemi- and photoluminescence, samples were counted for 2 min in a Wallac 1410 S-counter over a 3, 7 or 20 d period, depending on the sample source. During the periods between counting, samples were stored in the dark at ambient temperature. All calculations were performed on stabilised samples from which all chemi- and photoluminescence had been removed.

To determine the percentage of injected MTX in the plasma, it was necessary to calculate the total plasma volume of each mouse (ml), using the standard formula:

$$\text{Mouse mass (g)} \times \text{mouse blood volume}(0.07) \times \text{plasma proportion of blood}(0.59)$$

The percentage of injected MTX in the plasma was then calculated:

$$\frac{\text{Plasma volume (ml)} \times dpm/\text{ml plasma} \times 100}{\text{total } dpm \text{ injected}} = \% \text{ injected } MTX \text{ in plasma}$$

To ensure an accurate quantitation of the amount of MTX delivered to the blood stream, the injection site on the tail vein was dissected and the MTX quantitated. The mean percentage of the MTX injection remaining at the injection site was 3.78% (SEM: 0.57%). The amount of MTX delivered to the bloodstream (MTX available for distribution to the tissues and tumour) was calculated as:

$$\text{Amount of MTX delivered to bloodstream (Dpm)} = \text{Difference in mass of injection syringe (mg)} \times Dpm/\text{mg of injection material} - Dpm \text{ remaining at injection site}$$

The amount of MTX delivered to the bloodstream henceforth will be referred to as the "injected dose".

In order to make accurate comparisons between the sample population and normalise slight variations in organ and tumour masses, the concentration of MTX in the body organs and tumour and body fluid was expressed as % of injected dose/gram of tissue.

The mean percentage of the MTX injection remaining at the injection site was 3.78% (SEM: 0.57%). To normalise such variations, the percentage of dpm found in tumour and tissues was calculated as a percentage of the dpm injected minus the dpm found remaining at the injection site. This amount is henceforth referred to as the available dpm or available methotrexate. The results are summarised in Table 2.

active content was measured after the addition of 3 ml HiSafeII scintillant to samples ranging from 8-30 µl. Despite the technical difficulties in accurately quantitating the volume of urine produced by each mouse we calculated the percentage of injected MTX dose in the urine by the following formula:

$$\frac{\text{time of collection }(h) \times 42 \; \mu l \times dpm/\mu l \; \text{urine} \times 100}{\text{Total } dpm \text{ injected}} = \% \text{ of injected MTX in urine.}$$

It was not possible to collect urine from each mouse, because of variations in the micturition rate. When 3 or more urine specimens were available per time point per treatment non-parametric statistical analysis of the data at those time points was performed. At one hour after administration there was 50% (p=0.043) more MTX in the urine of mice which received MTX/HA (see Table 2).

Immediately after killing the mouse the tumour, liver, heart, spleen, bladder, left and right kidneys, uterus, lungs, stomach, intestines, brain and lymph nodes were excised and analysed for total radioactivity. The total radioactivity in each tissue was determined by solubilising 100-400 mg of tissue in 3-6 ml of OptiSolv (ACC, Melbourne, Australia) for 36 h, 22° C. On completion of solubilisation, radioactivity in the tissue was counted after adding 10 ml of HiSafeIII scintillant. Again to overcome chemi- and photoluminescence, samples were

TABLE 2

Methotrexate uptake in mouse tumours, organs and body fluids

| | MTX only (median % ± SE) | | | | | HA/MTX (median % ± SE) | | | | |
|---|---|---|---|---|---|---|---|---|---|---|
| | 30 min | 1 Hr | 2 Hr | 4 Hr | 8 Hr | 30 min | 1 Hr | 2 Hr | 4 Hr | 8 Hr |
| Tumour | 0.66 ± 0.09 | 0.50 ± 0.04* | 0.32 ± 0.03* | 0.31 ± 0.02 | 0.22 ± 0.05 | 0.88 ± 0.04 | 0.62 ± 0.03* | 0.46 ± 0.32* | 0.34 ± 0.12 | 0.17 ± 0.02 |
| Liver | 9.56 ± 1.92 | 4.63 ± 1.50 | 2.13 ± 0.55 | 2.11 ± 2.16 | 0.71 ± 1.84 | 12.83 ± 1.66 | 7.14 ± 0.92 | 2.43 ± 0.24 | 1.99 ± 0.45 | 0.49 ± 0.08 |
| Spleen | 0.39 ± 0.09 | 0.24 ± 0.18 | 0.17 ± 0.05 | 0.26 ± 0.05 | 0.12 ± 0.01 | 0.48 ± 0.06 | 0.34 ± 0.03 | 0.24 ± 0.03 | 0.26 ± 0.10 | 0.14 ± 0.00 |
| Lymph Nodes | 2.33 ± 0.39 | 0.89 ± 0.55 | 0.69 ± 0.42 | 0.94 ± 0.19 | 0.26 ± 0.08 | 1.28 ± 0.23 | 1.49 ± 0.26 | 0.58 ± 0.10 | 0.24 ± 0.08 | 0.10 ± 0.01 |
| Left Kidney | 0.41 ± 0.05 | 0.13 ± 0.02 | 0.08 ± 0.01 | 0.13 ± 0.03 | 0.04 ± 0.00 | 0.39 ± 0.04 | 0.16 ± 0.05 | 0.09 ± 0.00 | 0.10 ± 0.04 | 0.04 ± 0.02 |
| Right Kidney | 0.40 ± 0.06 | 0.14 ± 0.01 | 0.10 ± 0.02 | 0.11 ± 0.01 | 0.04 ± 0.00 | 0.46 ± 0.06 | 0.18 ± 0.02 | 0.10 ± 0.01 | 0.08 ± 0.05 | 0.05 ± 0.01 |
| Bladder | 8.44 ± 39.0 | 5.46 ± 5.30 | 1.65 ± 1.08 | 1.63 ± 1.49 | 0.50 ± 0.66 | 5.29 ± 16.07 | 16.96 ± 8.99 | 3.18 ± 3.89 | 1.89 ± 3.16 | 0.21 ± 0.04 |
| Intestines | 11.75 ± 2.26 | 16.89 ± 8.51 | 10.41 ± 2.59 | 10.83 ± 3.04 | 3.38 ± 1.68 | 5.65 ± 1.75 | 9.66 ± 5.73 | 5.84 ± 4.16 | 4.55 ± 2.64 | 1.12 ± 1.71 |
| Stomach | 3.75 ± 2.10 | 4.38 ± 1.73 | 5.86 ± 1.22 | 0.84 ± 0.31 | 0.24 ± 0.06 | 2.64 ± 0.68 | 4.44 ± 0.87 | 4.52 ± 0.59 | 1.24 ± 0.71 | 0.49 ± 0.20 |
| Brain | 0.13 ± 0.03 | 0.10 ± 0.03 | 0.08 ± 0.12 | 0.14 ± 0.03 | 0.08 ± 0.00 | 0.17 ± 0.02 | 0.16 ± 0.03 | 0.10 ± 0.02 | 0.12 ± 0.07 | 0.09 ± 0.01 |
| Heart | 0.44 ± 0.03 | 0.37 ± 0.13 | 0.20 ± 0.24 | 0.21 ± 0.03 | 0.10 ± 0.03 | 0.53 ± 0.05 | 0.26 ± 0.04 | 0.16 ± 0.04 | 0.16 ± 0.09 | 0.12 ± 0.01 |
| Lungs | 0.90 ± 0.11 | 0.40 ± 0.14 | 0.30 ± 0.16 | 0.33 ± 0.07* | 0.15 ± 0.14 | 0.12 ± 0.14 | 0.41 ± 0.10 | 0.24 ± 0.09 | 0.16 ± 0.01 | 0.14 ± 0.02 |
| Uterus | 0.67 ± 0.12 | 0.33 ± 0.23 | 0.30 ± 0.07 | 0.27 ± 0.07 | 0.11 ± 0.01 | 0.78 ± 0.70 | 0.62 ± 0.24 | 0.28 ± 0.12 | 0.19 ± 0.14 | 0.11 ± 0.01 |
| Plasma# | 1.49 ± 0.31 | 1.51 ± 0.48 | 0.45 ± 0.23 | 0.31 ± 0.12 | 0.15 ± 0.02 | 1.06 ± 0.28 | 0.53 ± 0.34 | 0.31 ± 0.15 | 0.42 ± 0.15 | 0.13 ± 0.00 |
| Urine@ | 14.28 ± 1.65 | 9.06 ± 3.47* | 20.44 ± 3.38 | 23.55 ± 4.01 | ID | 15.64 ± 4.46 | 18.03 ± 2.44 | 12.81 ± 2.41 | 35.58 ± 6.05 | ID |

Values are the median + SEM, where n = 8
* and ▨ represent statistically significant figures when data is analysed using the Mann-Whitney Rank Sum Test
represents MTX Dpm in total plasma volume of mouse. Figures represent Plasma MTX Dpm as % if the injected MTX dose
@represents MTX Dpm in total urine of mouse. Figures represent as % of the injected dose. N = 3-8
ID represents insufficient data for analysis No statistically significant difference was noted in the plasma levels of MTX when the drug was co-injected with HA. The gross pharmacokinetics of MTX remained unaltered, with maximum MTX plasma levels reached within 0.5 to 2 h following intravenous administration (MIMS, 1997).

When possible urine was collected from the non-wettable plastic enclosures with a syringe and needle. The urine was cleared by centrifugation at 14,000 $g_{av}$ for 10 min. Its radiocounted for 2 min in a Wallac 1410 β-counter over a 3, 7 or 20 d period depending on the sample source. During the periods between counting, samples were stored in the dark at ambient temperature. All calculations were performed on stabilised samples from which all chemi- and photoluminescence had been removed. Figures represent median±SEM (n=8).

It was important to establish that metabolically active organs such as the liver, spleen and kidneys did not experience a high level of drug targeting which could counter-act any positive aspects of increased tumour targeting. Table 2 lists the methotrexate uptake of each tissue at the various time points tested.

Utilising the Mann-Whitney Rank Sum Test and Students τ-test there was no statistically significant difference in MTX concentration/g tissue when MTX was co-injected with HA. Because of the small number of animals at each time point, the Mann-Whitney test became statistically invalid if one data point overlapped, but in the liver, uterus and intestine a definite trend could be observed.

Figure 7:
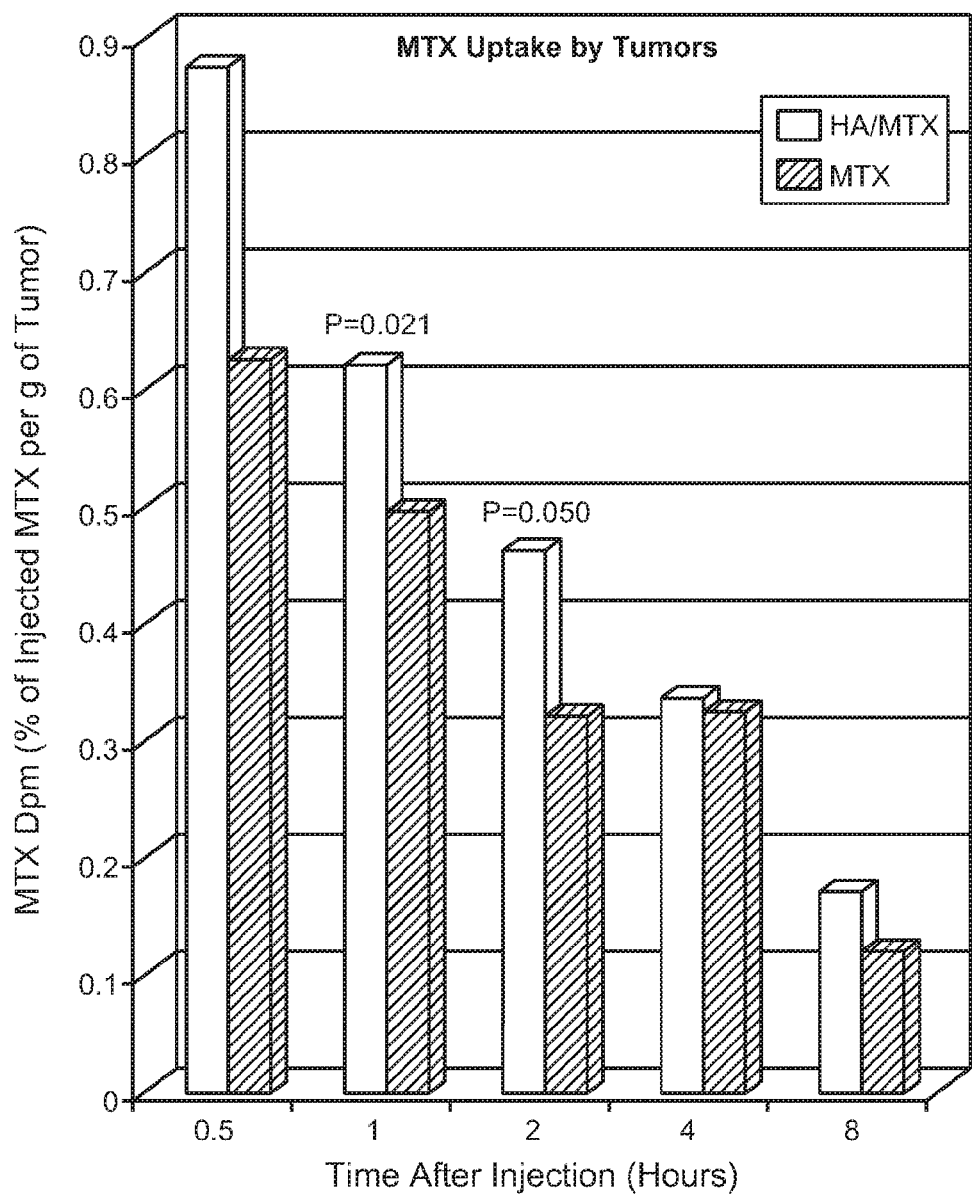
FIG. 7 shows methotrexate targeting of human breast cancer tumours, using HA as a carrier.

In the liver there appeared to be a short-term increase in the uptake of MTX when it was combined with HA, as shown in FIG. 7.

Figure 8:
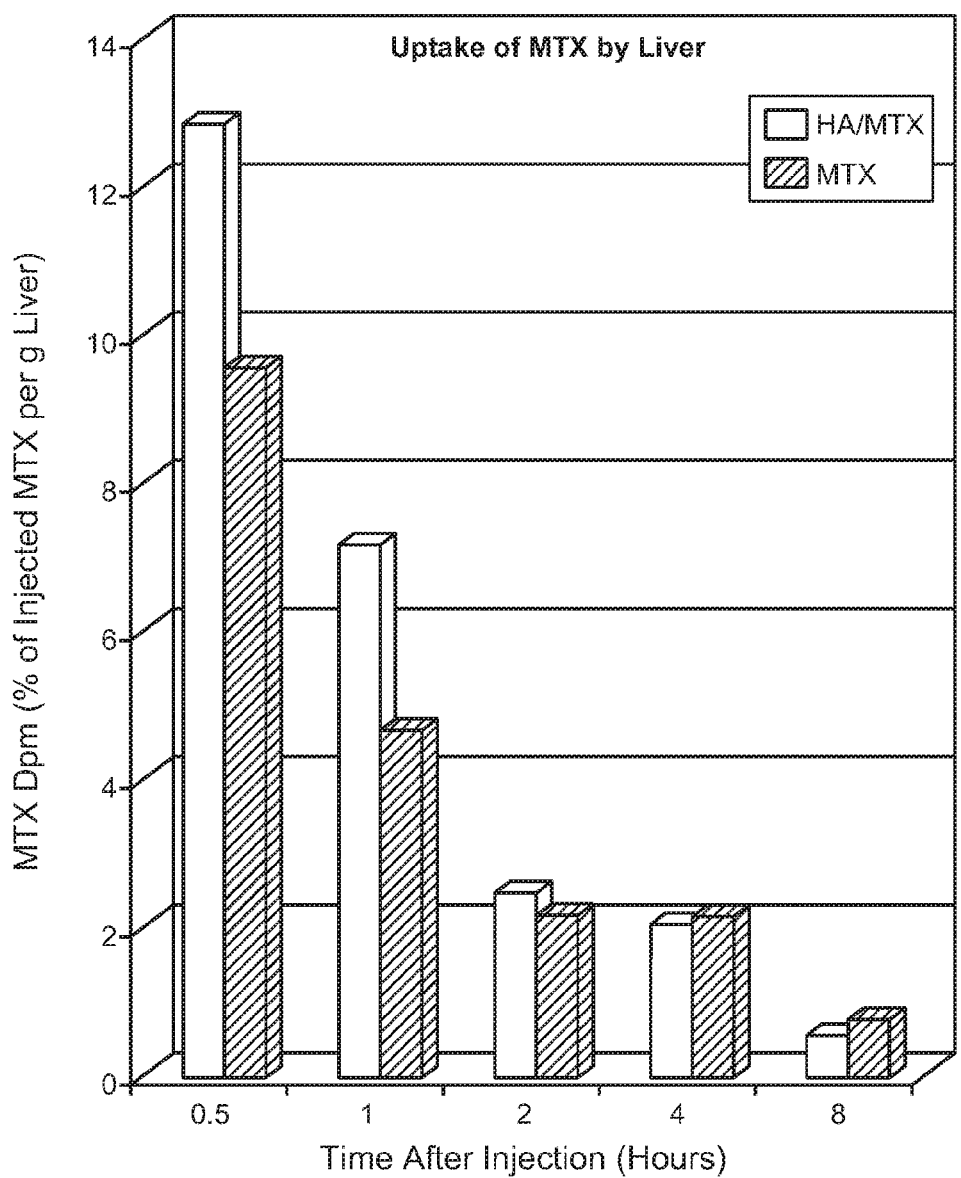
FIG. 8 shows enhanced uptake of methotrexate in the liver in the presence of HA.

At 30 min and 1 h the liver contained a median increase in MTX concentration of 65% and 26% respectively. At 2 h no difference was observed in the amount of MTX in the liver regardless of treatment. An interesting trend became apparent after 4 h, when less MTX was found in the liver when it was co-injected with HA (4 h: 68% less MTX and 8 h: 75% less MTX), as shown in FIG. 8.

Figure 9:
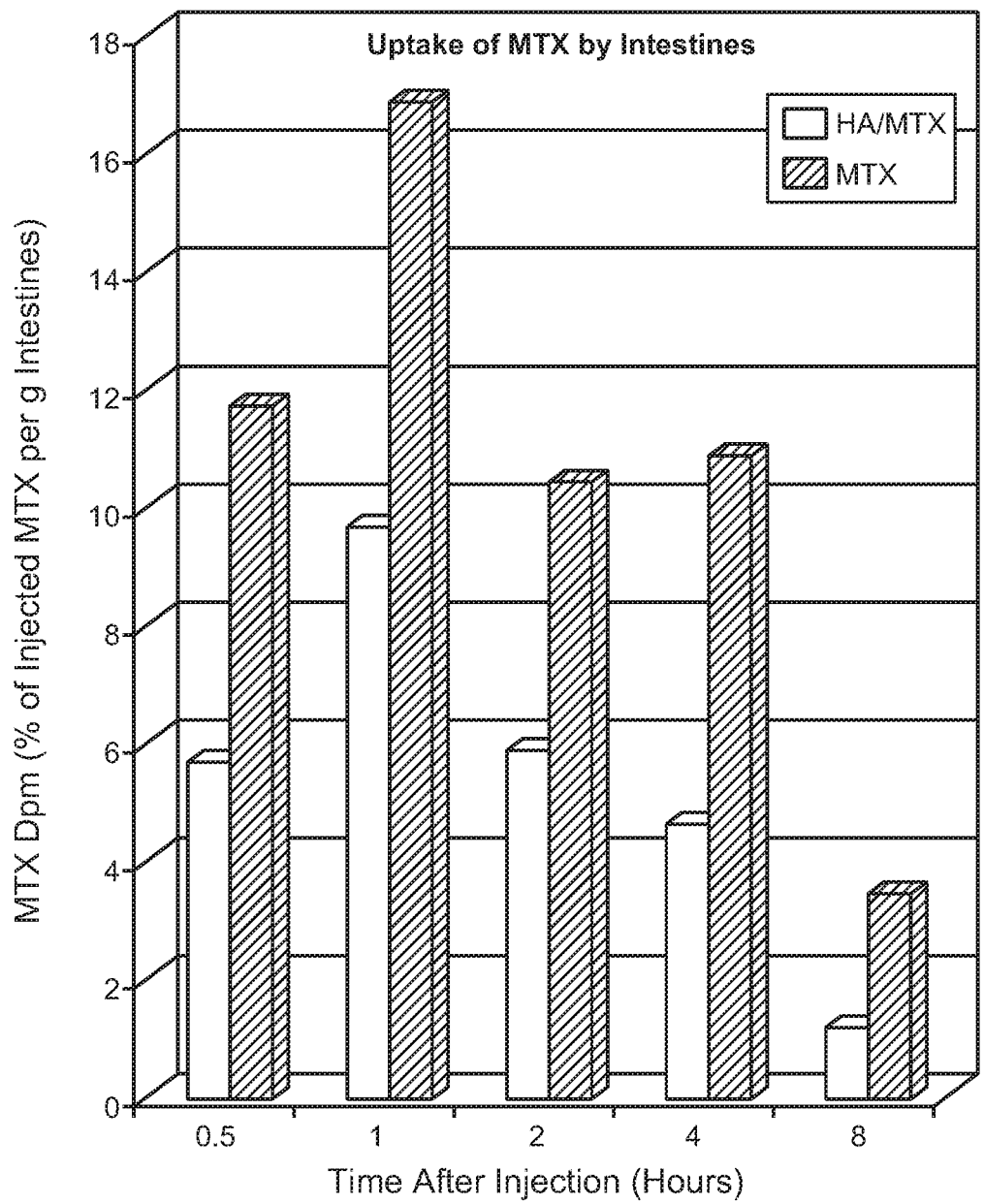
FIG. 9 shows reduced uptake of methotrexate in the gastrointestinal tract when drug is administered with HA.

There was a significant trend in the intestine, where the combination of HA and MTX resulted in a decreased uptake of the drug at every time point, as shown in FIG. 9.

The intestine was fully homogenised, followed by solubilisation of approximately 400 mg of tissue in 3-6 ml of Opti-Solv for 24 h at 22° C., followed by the addition of 10 ml Hisafe-3 scintillant. To overcome chemi- and photoluminescence, samples were counted for 2 min in a Wallac 1410 β-counter over a 3, 7 or 20 d period depending on the sample source. During the periods between counting, samples were stored in the dark at ambient temperature. All calculations were performed on stabilised samples where all chemi- and photoluminescence had been removed.

The figures represent median±SEM (n=8). Analysing the data with the non-parametric randomization test for matched pairs demonstrated that the co-administration of HA significantly reduced the excretion of drug into the GI tract (p=0.031, one-tailed test).

The decrease in MTX concentration ranged from 43-67%. The non-parametric randomization test for matched pairs showed that the co-administration of HA significantly reduced the excretion of drug into the gastrointestinal tract (p=0.031, one-tailed test).

In the lungs there was significantly less MTX present at 4 h when co-administered with HA, with a median decrease of 52% (p=0.014). No differences were demonstrated at other time points, however, so that the significance of this observation remains uncertain.

No observable trends were detected in the spleen, uterus, brain, heart, lymph nodes, stomach and kidneys.

Figure 10:
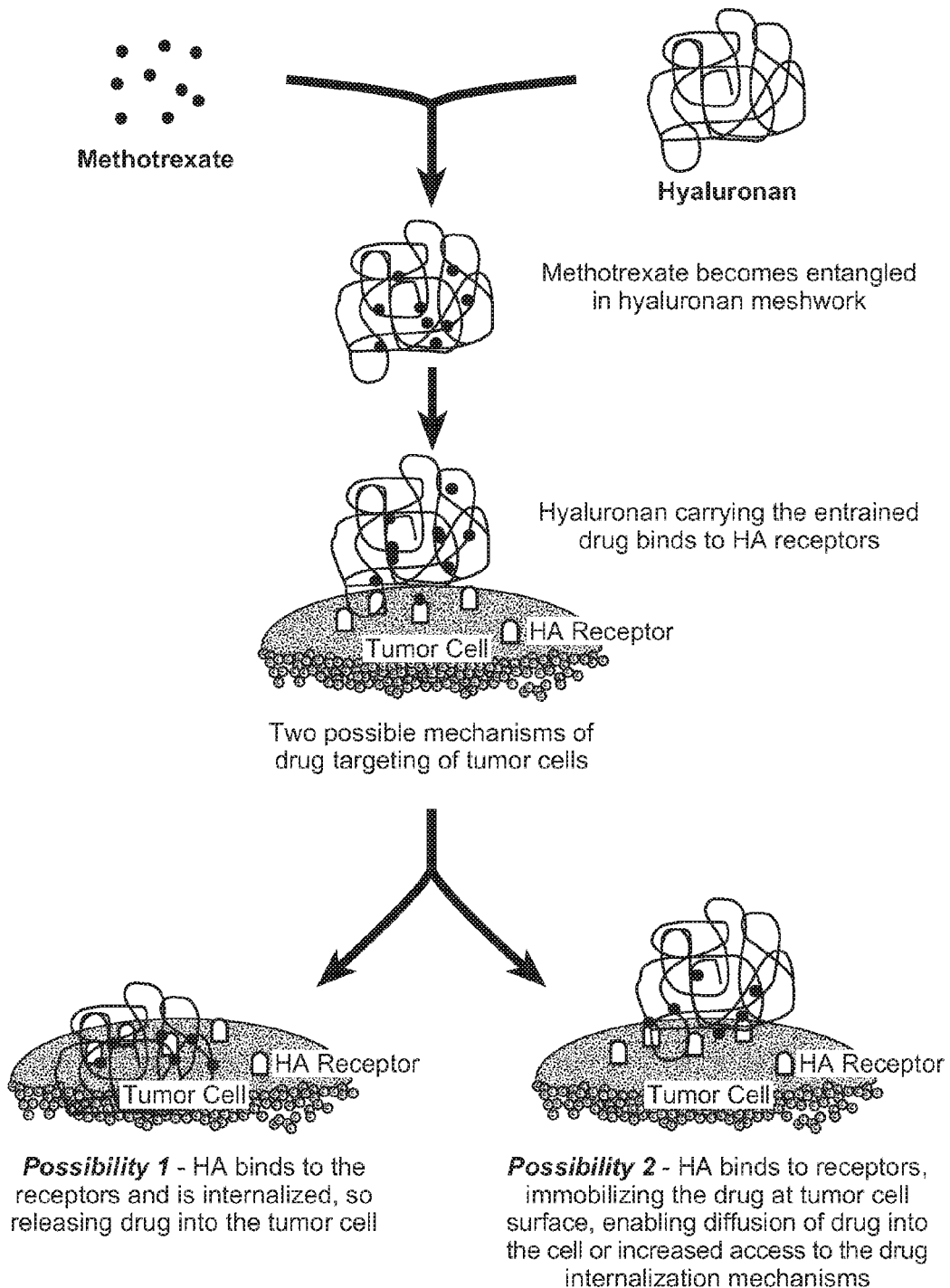
FIG. 10 shows a diagrammatic representation of possible physical interactions between MTX/HA and subsequent tumour targeting abilities of the drug/HA combination therapy.

There are two possible mechanisms of HA targeting of methotrexate to tumour cells (FIG. 10).

There was a significant targeting effect when HA was combined with MTX (FIG. 7). The greatest relative increase in tumour retention of drug was observed at 0.5 h (mean 24% increase), 1 h (mean 30% increase) and 2 h (mean 119% increase), whereas at 4 h and 8 h the increase was negligible. Because of the small population size and non-parametric distribution of the data the Mann-Whitney Rank Sum Test test was used, and revealed a significant increase in tumour uptake of drug when HA was co-injected. At 1 h the statistical significance was p=0.01 and at 2 h, p=0.050. The other time points did not demonstrate a statistically significant difference, but the trend in MTX concentration/g of tumour was consistently greater when co-injected with HA.

The data shown in FIG. 7 unequivocally demonstrate that co-administration with HA has greatly increased the uptake of MTX by the tumour within 30 min after injection. Moreover, co-administration also sustains a distinctly higher level during the subsequent decay in the concentration of drug within the tumour. At 1 h the difference was significant at p=0.021 ($n_1$=8, $n_2$=8), and at 2 h when p=0.05 ($n_1$=8, $n_2$=8) as assessed by non-parametric tests.

HA containing entrapped MTX binds to the receptors (CD44 and/or I-CAM-1) and is internalised via receptor-mediated endocytosis, so releasing the drug into the tumour cell.

The HA molecular mesh will act as an impediment to outward diffusion, so that after HA binds to receptors (CD 44, RHAMM and/or ICAM-1), the entrained MTX is able to diffuse into the tumour cells. While held at the surface of the cells by the HA matrix the MTX has increased availability to the active transport mechanism normally utilised for MTX transport into the underlying cell.

The side-effects and the distribution of a drug to tissues other than the desired sites of activity can also be influenced by its association with HA. For example, HA is normally cleared from the bloodstream by receptor-mediated cellular uptake and catabolism in the liver (80-90%), kidneys (10%), spleen and bone marrow, with some minor species variation in the last two sites. As expected HA does seem to increase hepatic delivery of the drug at least for a short time. At 30 min and 1 h the liver showed a median increase in MTX concentration of 65% and 26% respectively. At 2 h no difference was observed in the amount of MTX in the liver, regardless of treatment. An interesting trend became apparent after 4 h, where less MTX was found in the liver when it was co-injected with HA (4 h: 68% less MTX and 8 h: 75% less MTX). After intravenous administration MTX is widely distributed in body water, and can be retained in the liver for months (McEvoy, 1988); therefore the decreased median concentration of MTX in the liver at 4 and 8 h when co-injected with HA could indicate an altered balance in the routes of pharmacokinetic clearance. Considering that HA is rapidly metabolised within the liver endothelial cells (LEC) it follows that MTX which is co-internalised with HA would be released within the liver sinusoidal lining cells, where it could either diffuse into hepatocytes to be secreted in the bile and subsequently the gastrointestinal tract, or be returned to the circulation for further distribution into body water and for urinary excretion, or both.

There could be a therapeutic advantage of short-term hepatic-targeting. In the case of liver metastasis a rapid, high exposure to MTX could be beneficial, and since the observed targeting is only for 1 h this would counteract any long term toxicity problems. Liver targeting could be utilised with drugs which require bio-activation, eg mitomycin C, doxorubicin, where the drug/HA mixture would be targeted to the LEC. With the inactive drug concentrated in the LEC it would be able to diffuse into the hepatocytes for activation, thus acting as an activation targeting mechanism.

One of the major sites of toxicity of MTX is the gastrointestinal tract. Co-administration of MTX with HA significantly diminished the amount of drug delivered to the GI tract. There may be several mechanisms associated with the decreased concentration of MTX in the gut.

Methotrexate is a very small molecule, which one would expect normally to pass through most capillary walls, whereas association with HA would greatly reduce its passage through this route.

Rapid degradation of HA in the liver endothelial cells resulted in a rapid release of MTX into the liver and return to the bloodstream, where it would undergo increased renal clearance, as indicated at 1 h, and which 50% more MTX was excreted in the urine of mice receiving MTX/HA preparations.

The main pathway for the final elimination of MTX from the body is urinary excretion. There seems to be little increase in renal content of the drug with HA, but we believe from other evidence that HA is taken up and catabolised very quickly by the kidneys, so that its residence time would be short and associated drug would be quickly released into the urine.

Conclusion

The results reported here represent the first stage of a pre-clinical study to examine the proposition that administration of therapeutic agents together with hyaluronan will achieve their selective delivery to the desired target of pathological tissue; thus achieving a higher and more effective concentration at that point. In this case methotrexate, a cytotoxic drug widely used in current treatment regimens for human mammary cancer and other human malignancies, and for rheumatoid arthritis, has been studied by the intravenous route of administration with and without hyaluronan.

We have found that the nude mouse model is a particularly suitable model for the study of human breast cancer in a living host, and to resolve some fundamental matters in the use of HA to direct therapeutic agents to the sites of diseased tissue, and thus to enhance their beneficial effects. Our results have been achieved with a drug of small molecular weight that shows no specific form of association with HA, demonstrating that HA can still deliver such a drug in enhanced amounts to pathological tissue when injected into the bloodstream. This study demonstrates that in the conditions prevailing in the body, the MTX is sufficiently retained with HA to effect a significant enhancement of delivery to human breast cancer, as well as potentially reducing the undesired side-effect of gastrointestinal toxicity.

Example 3

Preparation and Injection of Paclitaxel/Hyaluronan Drug Combinations

Having established the usefulness of the nude mouse model for HA/Paclitaxel, it could now be used to test the effectiveness of other chemotherapeutics. It was decided that, due to its therapeutic importance, paclitaxel (also known as taxol) would be used.

Paclitaxel is isolated from the Western Yew, *Taxus brevifolia*, (Wani et al 1971), and is clinically active against advanced ovarian and breast cancer (Rownisky et al 1990; McGuire et al 1989) and is currently undergoing clinical trials for treatment of a variety of other cancers. However the main problem associated with paclitaxel is its extreme lipophilicity and consequent poor aqueous solubility. Efforts to solve this problem have led to the synthesis of paclitaxel analogues and prodrugs along with extensive efforts to devise safe and biocompatible formulations. To date no prodrugs have shown sufficient stability, solubility or activity that would warrant clinical development (Mathew et al 1992; Vyas et al 1993). However, semisynthetic taxanes are showing greater solubility and potency than paclitaxel (Bissery et al 1991) and one form Taxotere has entered human trials (Bisset et al 1993).

The current clinical formulation of paclitaxel employed for intravenous delivery utilises ethanol and Cremophor EL in a 1:1 (v/v) ratio with the drug at 6 mg/mL. Cremophor EL is actually polyethoxylated castor oil; a clear, oily viscous, yellow surfactant. Stability studies have shown that the original formulation has a shelf-life of 5 years at 4° C. The preparation is diluted before use with 0.9% saline or 5% dextrose to concentrations of 0.3-1.2 mg/mL and the physical and chemical stability of the material in these conditions is ca. 27 h. However, dilution of the vehicle to these levels can produce a supersaturated solution (Adams et al 1993) that may be prone to precipitation if used outside the established guidelines. Therefore an in-line filter is required during administration as a safeguard against the infusion of particulates. It is also recommended that diluted paclitaxel solutions be used within 24 h of preparation. Hazing of the above solutions has also been observed and has been attributed to the extraction of plasticisers by Cremophor from the infusion bags and tubing (Waugh et al 1991).

In addition to the problems of physical instability mentioned previously the most significant problem with Cremophor is the fact that it is reported to have pharmacological activity. A variety of drugs are administered using Cremophor EL including cyclosporin, tacrolymus and teniposide. However, the dose of Cremophor EL given with paclitaxel is higher than with any other marketed drug. Cremophor has been observed to cause serious or fatal hypersensitivity episodes. Vehicle toxicity may also be largely responsible for fatal or life threatening anaphylactic reactions observed upon rapid infusion of paclitaxel into animals or humans (Dye & Watkins 1980; Lorenz et al 1977; Weiss et al 1990).

A stock solution of paclitaxel is prepared by and individual injections are prepared according to individual mouse body masses.

Desiccated HA (modal Mr $8.9 \times 10^5$ Da) is added to a portion of the 24.5 mg/ml paclitaxel stock solution and dissolved overnight with vortexing, to give a final concentration of 21 mg/ml. To ensure sterility gentamicin is added to a concentration of 50 µg/ml and incubated overnight at 4° C. Following the addition of [$^3$H]paclitaxel the HA/paclitaxel stock mixture is diluted to injection concentration with injection grade sodium chloride. Injections are individually made according to mouse body masses, to deliver 15 mg/kg paclitaxel and 12.5 mg/kg HA in 50 µl. With this quantity of HA injected into the body, saturation kinetics would be observed for the period of the experiment (Fraser et al., 1983).

To ensure that the HA had maintained its molecular weight during the preparation of the paclitaxel/HA injection mixture, the injection solution is analysed on a Sephacryl S-1000 size exclusion gel (Pharmacia, Uppsala, Sweden) with column specifications of 1.6 cm×70 cm, sample size 2 ml, flow rate 18 ml/h and 2 ml fraction size. FIG. 6 shows that HA retained its molecular weight during the mixing procedure.

Mice are randomly divided into 2 groups of 40 animals. Group I received paclitaxel only, and Group 2 receive paclitaxel/HA combination therapy. Animals are individually placed in an injection box, and the injections are administered via the tail vein. Tritiated paclitaxel (mean injected disintegration's per minute (dpm)±standard error of the mean (SEM): 19,159,146±1,336,819) is delivered in each injection. Mice are individually housed in soft, non-wettable plastic enclosures so urine can be collected. At 30 min, 1 h, 2 h, 4 h or 8 h after injection mice are anaesthetised by 0.1 ml intraperitoneal injection of Nembutal (Glaxo, Australia Pty. Ltd., Melbourne, Australia), and blood is collected from the heart or great vessels using a needle and syringe. After blood collection the animals are killed by cervical dislocation.

Blood is delivered into EDTA-coated glass tubes and plasma is prepared by centrifugation at 14,000 $g_{av}$ for min. Radioactivity is counted in 50 µl aliquots after decolourisation with 100 µl of 30% v/v hydrogen peroxide and the addition of 3 ml HiSafeII scintillant. To overcome chemi- and photoluminescence, samples are counted for 2 min in a Wallac 1410 β-counter over a 3, 7 or 20 d period, depending on the sample source. During the periods between counting, samples are stored in the dark at ambient temperature. All calculations are performed on stabilised samples from which all chemi- and photoluminescence had been removed.

To determine the percentage of injected paclitaxel in the plasma, it is necessary to calculate the total plasma volume of each mouse (ml), using the standard formula:

Mouse mass (g)×mouse blood volume(0.07)×plasma proportion of blood(0.59)

The percentage of injected paclitaxel in the plasma is then calculated:

$$\frac{\text{Plasma volume (ml)} \times dpm/\text{ml plasma} \times 100}{\text{total } dpm \text{ injected}} =$$

% injected paclitaxel in plasma.

To ensure an accurate quantitation of the amount of paclitaxel delivered to the blood stream, the injection site on the tail vein is dissected and the paclitaxel quantitated. The mean percentage of the paclitaxel injection remaining at the injection site is also determined. The amount of paclitaxel delivered to the bloodstream (paclitaxel available for distribution to the tissues and tumour) is calculated as:

Amount of paclitaxel delivered to bloodstream ($Dpm$) =

Difference in mass of injection syringe (mg) × $Dpm$/mg of injection material − $Dpm$ remaining at injection site The amount of paclitaxel delivered to the bloodstream henceforth is referred to as the "injected dose".

In order to make accurate comparisons between the sample population and normalise slight variations in organ and tumour masses, the concentration of paclitaxel in the body organs and tumour and body fluid is expressed as % of injected dose/gram of tissue.

The mean percentage of the paclitaxel injection remaining at the injection site is calculated. To normalise such variations, the percentage of dpm found in tumour and tissues is calculated as a percentage of the dpm injected minus the dpm found remaining at the injection site. This amount is referred to as the available dpm or available paclitaxel.

When possible urine is collected from the non-wettable plastic enclosures with a syringe and needle. The urine is cleared by centrifugation at 14,000 $g_{av}$ for 10 min. Its radioactive content is measured after the addition of 3 ml HiSafeII scintillant to samples ranging from 8-30 μl.

Immediately after killing the mouse the tumour, liver, heart, spleen, bladder, left and right kidneys, uterus, lungs, stomach, intestines, brain and lymph nodes are excised and analysed for total radioactivity. The total radioactivity in each tissue is determined by solubilising 100-400 mg of tissue in 3-6 ml of OptiSolv (ACC, Melbourne, Australia) for 36 h, 22° C. On completion of solubilisation, radioactivity in the tissue is counted after adding 10 ml of HiSafeIII scintillant. Again to overcome chemi- and photoluminescence, samples are counted for 2 min in a Wallac 1410 β-counter over a 3, 7 or 20 d period depending on the sample source. During the periods between counting, samples are stored in the dark at ambient temperature. All calculations are performed on stabilised samples from which all chemi- and photoluminescence had been removed.

Example 4

Use of 5-Fluorouracil and HA Introduction

5-Fluorouracil is (5-FU) an antimetabolite that is commonly used in the treatment of breast and gastrointestinal tract cancers (Piper & Fox, 1982). 5-FU is converted to its active nucleotide form intracellularly where it interferes with both DNA and RNA synthesis. The drug functions via two mechanisms in vivo:

(i) FdUMP binds tightly to thymidylate synthase preventing the formation of thymidylate, which is an essential precursor of deoxythymidine triphosphate (dTTP) which is one of the four deoxyribonucleotides required for DNA synthesis. The thymine-less state created by this inhibition is toxic to actively dividing cells (Pinedo & Peters, 1988).

(ii) The second way in which 5-FU functions is that the incorporation of FUTP into RNA interferes with RNA function. The inhibition of thymidylate synthase caused by Fdurd and 5-FU incorporation into RNA is capable of causing cytotoxic effects on cells. Both the concentration and duration of exposure of 5-FU are important determinants of cytotoxicity. As RNA-directed effects are probably predominant with prolonged duration of exposure, where as DNA-directed effects might be more important during short-term exposure of cells in S phase.

Several studies have examined the use of HA as a drug delivery system for anti-cancer drugs. Coradini et al (1999) covalently bound sodium butyrate to HA, to determine whether this HA/sodium butyrate combination would enhance drug uptake by breast cancer cells in vitro. This study indicated that the mechanism of action of HA as a drug delivery vehicle may involve the HA-butyrate-ester derivative being carried to the CD44 receptors. The HA/drug complex was internalised, followed by cytoplasmic hydrolysis of the HA/drug complex, subsequently releasing the butyrate which exerted an anti-proliferative effect. One in vivo study has been performed which covalently linked mitomycin C to HA as a means of treating murine Lewis lung xenografts (Akima et al, 1996). It was found that the HA-MMC complex resulted in anti-tumour activity at a low dose of 0.01 mg/kg where the sole agent, mitomycin C did not demonstrate anti-tumour activity.

Example 5

Investigation of the Synergistic Action of 5-FU and HA in Human Breast Cancer Cells Human breast adenocarcinoma cell lines MDA-MB-468, MDA-MB-435 and MDA-MB-231 were selected based on HA binding affinity (Culty et al, 1994) and the expression of the HA receptors of CD44 and RHAMM (Wang et al, 1996). Summaries of the cell line characteristics are shown in Table 3.

TABLE 3

Hyaluronan Binding And Receptor Expression Of Human Mammary Carcinoma Cell Lines

| Cell Line | Type of breast cancer | Degree of HA Binding[a] | HA Receptor Expression[b] | |
|---|---|---|---|---|
| | | | CD44 | RHAMM |
| MDA-MB-231 | adenocarcinoma | ++ | +++ | +++ |
| MDA-MB-468 | adenocarcinoma | ++++ | ++++ | ++ |
| MDA-MB-435 | ductal carcinoma | + | +++ | ND |

[a]Culty et al, 1994
[b]Wang et al, 1996

Cell lines MDA-MB-468, MDA-MB-435 and MDA-MB-231 were routinely cultured as described in example 1.

It can be seen from Table 4 that breast cancer cells grown in media containing 0 nM 5-FU+100 nm of HA did not demonstrate a statistically significant proliferative or cytotoxic effect when compared to untreated cells.

TABLE 4

Effect Of Hyaluronan On Breast Cancer Cell Proliferation

| Cell Line | 0 nM 5-FU (mean cell number ± 1 S.D.) | 0 nM 5-FU + 100 nM HA (mean cell number ± 1 S.D.) |
|---|---|---|
| MDA-MB-231 (n = 4) | 34,206 ± 3,206 | 29,470 ± 4,452 |
| MDA-MB-468 (n = 4) | 36,751 ± 2,814 | 37,607 ± 3,325 |
| MDA-MB-435 (n = 4) | 117,760 ± 2,175 | 121,918 ± 7,851 |

Statistical testing was conducted using both the non-parametric Rank Sum Test and parametric Student's t-test Therefore all results were expressed as a percentage of the 0 nM 5-FU/0 nM HA cell count. Distinct differences in growth patterns were noted between cell lines, for example MDA-MB-231 and MDA-MB-468 cells demonstrated a poor plating efficiency, where numerous floating cells were present before application of the test media. The MDA-MB-435 cell line demonstrated a high plating efficiency and a very rapid growth rate.

Figure 11:
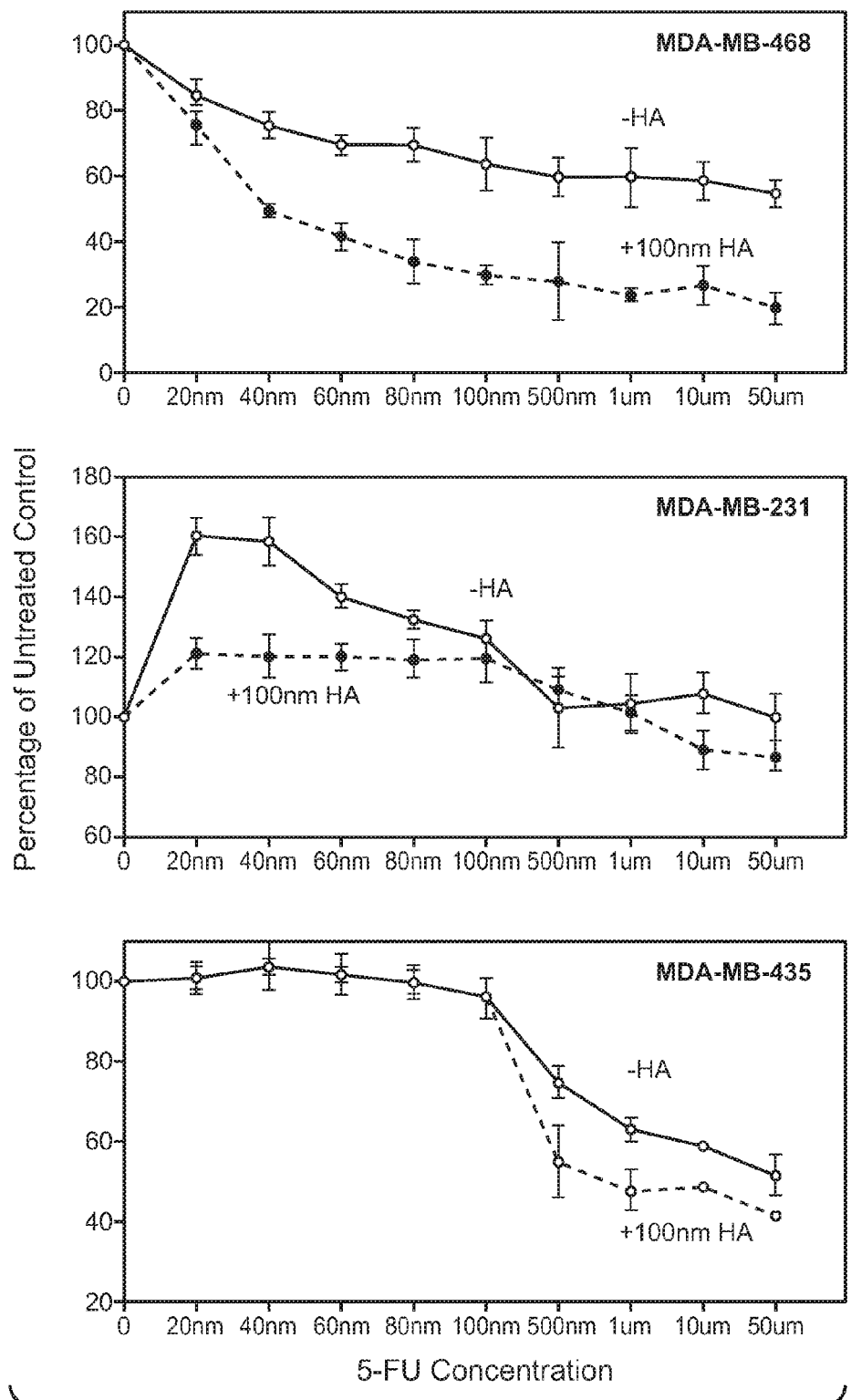
FIG. 11 shows the cytotoxic synergistic in vitro effect of combining HA with 5-FU.

When HA was combined with 5-FU a syngeristic cytotoxic effect was observed with the MDA-MB-468 cell line, but not with the MDA-MB-231 or MDA-MB-435 breast cancer cell lines. This is shown in FIG. 11. The $IC_{50}$ of 5-FU alone was >50 µm, but when combined with HA the $IC_{50}$ was 40 nM, a reduction in drug dosage of up to 1250 times.

The results from the in vitro experiments demonstrated an increase in cell kill when 5-FU was applied to the breast cancer cells in the presence of HA. The MDA-MB-468 cells showed the greatest susceptibility to the 5-FU/HA therapy where the $IC_{50}$ was decreased from >50 µM to 40 nM, whereas both the MDA-MB-231 and MDA-MB-435 were not greatly affected by the 5-FU/HA combination. All of the breast cancer cell lines expressed high levels of the CD44 receptor with the MDA-MB-468 (60-80%), MDA-MB-231 (40-60%) and MDA-MB-435 (40-60%) as determined by Culty et al (1994). It has been demonstrated that the three cell lines used in these experiments are able to degrade HA, implying that the function of CD44 in tumour cells may be to mediate the degradation of HA (Culty et al, 1994).

Another factor to consider is the previous exposure of the cells to chemotherapeutic drugs. Before a cancer cell line is isolated from a patient, the cancer sufferer has often undergone chemotherapy or radiation, which could result in the tumour containing treatment-resistant cells. In the case of MDA-MB-435 and MDA-MB-231 the patients from which the cell lines were derived had both been previously exposed to 5-FU (Cailleau et al, 1974). Since cancer cells contain several adaptation mechanisms to overcome drug cytotoxicity, it is very likely that the tumour mass that remained after treatment was resistant to 5-FU, subsequently altering the susceptibility of the cells to the drug in vitro.

With the view of extrapolating any in vivo data obtained mice to the treatment of human counterparts, the experimental model and design was carefully developed. To definitively demonstrate the in vivo targeting and therapeutic efficacy of 5-FU/HA adjuvant therapy on human breast cancer xenografts, the following factors were examined:

Human breast cancer tumours were established in a well-validated Walter and Eliza Hall Institute strain of nude mouse, a widely accepted model for such studies which avoids an immune response against allogenic cells.

Comparative data on the pharmacokinetics of 5-FU that have already been published for the nude mouse and humans (Inaba et al, 1988), and were utilised in the design of this study, to simulate human therapeutic doses as closely as possible.

A major aim was validation that the histological and cytological behaviour of the tumours established in these mice were comparable to that of such tumours in their natural human hosts. In achieving this aim we have also shown that the tumour cells in the mice are of human origin and that they express highly relevant HA receptors such as RHAMM and CD44.

Example 6

Preparation of HA and 5-FU Solutions

A stock of HA solution (10 µM, 7 mg/ml) was prepared by dissolving desiccated HA (modal Mr $7 \times 10^5$ Da,) in 0.9% w/v pyrogen-free injection grade NaCl. To ensure a homogenous solution the HA was dissolved overnight at 4° C. followed by thorough vortexing. To ensure that 'the HA had maintained its molecular weight during the preparation of the stock solution, the solution was analysed on a Sephacryl S-1000 size exclusion gel with column –40 specifications of 1.6 cm×70 cm, sample size 2 ml, flow rate 18.1/h and 2 ml fraction size. The HA was used at a final concentration of 1000 nm, with all dilutions made in the appropriate growth medium.

The stock solution of 5-FU was prepared by dissolving 5-FU in 0.1M sodium hydroxide and brought to a concentration of 20 mg/ml with 0.9% w/v pyrogen-free injection grade NaCl. The stock solution was filtered through a 0.22 µm filter to ensure sterility before addition of [$^3$H]-FU and dilution to injection concentration with injection grade sodium chloride. Individual injections were prepared according to individual mouse masses, with the aim of delivering 30 mg/kg 5-FU in 50 µl (equivalent to human therapeutic dose of 10.5 mg/kg for a mean body weight of 60 kg; Inaba et al, 1988). A pyrogen-free, HA stock solution (10 mg/ml; modal $M_r$ $7 \times 10^5$ Da) was added to a portion of the 20 mg/ml 5-FU stock solution and incubated overnight with vortexing, to a final HA concentration equivalent to 12.5 mg/kg of mouse mass. Injections were individually made according to mouse masses, to deliver 30 mg/kg 5-FU and 12.5 mg/kg HA in 50 µl. With this quantity of HA injected into the body, saturation kinetics would be observed for the period of the experimentation (Fraser et al, 1983). To ensure that the HA had maintained its molecular weight during the preparation of the injection mixture, the injection solution was analysed on a Sephacryl S-1000 size exclusion gel with column specifications of 1.6 cm×70 cm, sample size 2 ml, flow rate 18 ml/h and 2 ml fraction size. Hyaluronan was detected in column fractions by the uronic acid assay.

The uronic acid assay was used to detect the presence of hyaluronan qualitatively from the fractions collected from the gel filtration chromatography procedure. A 25 µl aliquot of each fraction was then transferred into a 96 well plate. 250 µl of a carbazole reagent (3M carbazole/0.025M borate in $H_2SO_4$) was then added to these fractions. The 96 well plate was incubated for 45-60 min at 80° C. A Dynatech MR7000 plate reader with a 550 nm filter was used to read the 96 well plate. The absorbance was considered to be significant when it was >3 standard deviations above the background absorbance. The background was calculated by taking an equal number of sample points before and after $V_o$ and $V_t$ where the average number taken was 16 (Fraser et al. 1988).

The formulation of HA and 5-FU (10 mg/ml HA and 20 mg/ml 5-FU in 0.5% NaCl, pH 8.9) did not demonstrate a degradative effect on the molecular weight of the HA. Chromatographical analysis in a size exclusion gel indicated the maintenance of the modal molecular weight of 700,000 Da.

Example 7

Drug Cytotoxicity Assay: Experimental Design

In designing drug titration experiments in vitro it is desirable to apply drug concentrations similar to the concentrations reached in plasma after intravenous administration. When 5-FU is therapeutically administered by an intravenous route (iv) at 10.5 mg/kg (400 mg/m$^2$), the peak plasma level within 30 min is 8 µg/ml [61 µM, Kubo, 1990). Based on these plasma concentrations in vivo the following drug concentrations were selected; 0, 1, 5, 10, 20, 50, 100 µM 5-FU±100 nM HA. The cell lines MDA-MB-468, MDA-MB-231, and MDA-MB-435 were grown as specified above in examples 4 to 5. When the cultures reached confluence the cells were removed from the flasks in 0.25% trypsin/0.05% EDTA. The single-cell suspension was counted with a Coulter counter (ZM1 model) and cells were resuspended to 100,000 cells/ml in cell-specific media. Cells were plated into 24-well plates (2 cm$^2$ surface area) by adding 0.5 ml of cell suspension per well, resulting in 50,000 cells/well. Cultures were allowed to attach for 24 h, before the media was removed, monolayers washed with HBSS and the test media (5-FU+HA) applied. After 4 days of growth in test media the cultures were washed with HBSS, the cells removed from the well by trypsinisation with 0.25% trypsin/0.05% EDTA and cells were counted with a Coulter Counter.

Example 8

Evaluation of HA as a Drug Delivery and Tumour-Targeting Vehicle

Based on the results from the drug sensitivity in vitro experiments as described in examples 5 to 7, and the expression of the HA receptors of CD44 and RHAMM, the human breast carcinoma cell line MDA-MB-468 was selected as the cancer cell inoculant for the generation of any nude mouse human tumour xenografts. Cells were routinely grown and subcultured as a previously described in Example 5. For injection into mice, cells were grown to 100% confluency, trypsinised in 0.025% trypsin/0.01% EDTA solution, washed twice by centrifugation in a Beckman TJ-6 bench centrifuge at 400 $g_{av}$, for 10 min, counted using a Model-ZM Coulter counter and resuspended in serum-free Leibovitz L-15 medium at 1×10$^8$ cells/ml.

The athymic CBA/WEHI nude female mice, 6 to 8 weeks old, were maintained under specific pathogen-free conditions, with sterilised food and water available ad libitum. Each mouse received one injection containing 5×10$^6$ cells in 50 µl. The cells were injected with a 26 gauge needle into the mammary fat pad directly under the first nipple (Lamszus et al, 1997). Tumour measurements were made weekly by measuring three perpendicular diameters ($d_1 d_2 d_3$). Tumour volume was estimated using the formula:

$$(\tfrac{1}{6})\pi(d_1 d_2 d_3)$$

Treatment with 5-FU±HA was commenced approximately 4-8 weeks after the cancer cell inoculation. The mean tumour size for mice used in each study is summarised in Table 5.

TABLE 5

Summary of Human Breast Cancer Tumours at Commencement of Each Study

| Study | Tumour volume (mean ± SEM) | Tumour as % of net body mass (mean ± SEM) |
| --- | --- | --- |
| 5-FU targeting | 0.41 ± 0.01 mm$^3$ | 0.22 ± 0.10 mm$^3$ |
| Efficacy: 6-week | 0.37 ± 0.20 mm$^3$ | 0.19 ± 0.10 mm$^3$ |
| Efficacy: 6-month | 0.61 ± 0.36 mm$^3$ | 0.28 ± 0.17 mm$^3$ |

To establish the tumorigenicity of breast cancer cell line MDA-MB-468 and its ability to generate tumours upon injection into an appropriate animal host, it was necessary to perform pathological testing. For a tumour to be physiologically viable neovascularisation is essential where the capillary network supplies nutrients to the tumour. The presence of vascularisation, ductal invasion, necrosis, apoptosis, a high mitotic index and nuclear abnormalities are all characteristic of breast carcinoma. Examination of the haematoxylin and eosin stained breast tumour sections demonstrated all of these features, so confirming that the animal host successfully maintained a grade II human breast carcinoma.

Approximately 8 weeks after tumour induction two tumour-bearing mice were given a lethal dose of Nembutal. Within 3 min of killing the mice, tumours were surgically removed and immediately fixed in 10% buffered formalin for 12 h. The fixed tumour was dehydrated overnight in a series of 70-100% ethanol, followed by paraffin embedding from which 2-4 µm sections were cut. The sections were placed on slides, de-waxed, and brought to water. Slides were washed 3×5 min in PBS. Heterophile proteins were blocked by incubation with 10% foetal calf serum for 10 min, followed by a PBS rinse. The detection antibodies were applied for 60 min at RT. The detection antisera or antibodies were against RHAMM, CD44H and CAE. The slides were washed 3×5 min in PBS and endogenous peroxidase activity blocked by immersion in 0.3% $H_2O_2$ in methanol for 20 min. Following a further PBS wash, the peroxidase-conjugated pig anti-rabbit secondary antiserum was applied for 60 min at RT, followed by 3×5 min washes in PBS. Sigma Fast 3,3'-Diaminobenzidine tablets (DAB) were prepared according to the manufacturer's instructions and the DAB solution was applied for 5-10 min at RT. The slides were washed in tap water for 10 min, counterstained with haematoxylin, dehydrated and mounted.

The human origin of the tumour was confirmed by staining the tumour and surrounding tissue with a human-specific cancer marker. The presence of CEA clearly demonstrated that the tumour was human, while being maintained by the cardiovascular system of the murine host. Since it was hypothesised that tumour targeting could occur via receptor-mediated internalisation or binding it was necessary to establish the expression of HA receptors, CD44 and RHAMM. Table 6 lists the degree of receptor expression on the human breast cancer xenografts.

TABLE 6

Distribution of HA receptors on human breast cancer tumours grown in nude mice

| HA receptor | Function | Distribution on tumour | % epitope expression on tumour |
|---|---|---|---|
| CD44H | Isoforms which bind and internalise HA (Culty et al, 1992) | Expressed on all cells except for a few stromal cells | ++++ |
| CD44 v 6 | Functional role in cancer unknown however the higher the expression results in a diminished survival probability (Friedrichs et al, 1995) | Some infiltrating tumour cells | + |
| CD44 v 3 | Over-expression often found in breast carcinoma (Friedrichs et al, 1995) | | − |
| RHAMM | Necessary for transformation and tumour cell invasion (Hall et al, 1995) | Groups of infiltrating tumour cells, with high expression on cells surrounding necrotic areas. | +++ |
| CEA | A foetal antigen expressed on malignant cells (Haskell, 1990) | Expressed on all tumour cells | ++++ |

Rating index for percentage of epitope expression on tumour:
0%: −
1-25%: +
26-50%: ++
51-75%: +++
76-100%: ++++

Example 9

Use of 5-FU and HA in Nude Mouse Model

Mice were randomly divided into 2 groups of 25 animals. Group 1 received [$^3$H]5-FU only, and Group 2 received the [$^3$H]5-FU/HA combination. The treatments were quantitatively administered via the tail vein with weighing of the injection syringe before and after injection. Tritiated 5-FU (mean injected dpm±SEM: 31,313,002±131,348) contained within 30 mg/kg 5-FU±12.5 mg/kg HA was delivered in each injection.

To ensure an accurate quantitation of the amount of [$^3$H] 5-FU delivered to the blood stream, the injection site on the tail vein was dissected and its [$^3$H]5-FU content measured. The amount of 5-FU delivered to the bloodstream (5-FU available for distribution to the tissues and tumour) was calculated as:

Amount of 5-$FU$ delivered to bloodstream ($dpm$) =

Difference in mass of injection syringe (mg) × $Dpm$/mg of injection material − $Dpm$ remaining at injection site The amount of 5-FU delivered to the bloodstream was referred to as the "injected dose".

In order to make accurate comparisons between the sample population and normalise slight variations in organ and tumour masses, the concentration of 5-FU in the body organs and tumour and body fluid was expressed as % of injected dose/gram of tissue.

Mice were individually housed in soft, non-wettable plastic enclosures so urine could be collected. At 10 min, 20 min, 30 min, 1 h or 2 h after injection mice were anaesthetised by 0.1 ml intra-peritoneal injection of Nembutal.

Upon anaesthetising the animals, blood was collected from the heart or great vessels using a needle and syringe. Blood was collected into EDTA glass tubes and plasma was prepared by centrifugation at 14,000 gav for 10 min. Radioactivity was counted in 50 µl after decolourisation with 100 µl of hydrogen peroxide, 30% v/v and the addition of 3 ml HiSafeII scintillant. To overcome chemi- and photoluminescence, samples were counted for 2 min in a Wallac 1410 f-counter over a 3, 7 or 20 d period depending on the sample source. During the periods between counting, samples were stored in the dark at ambient temperature. All calculations were performed on stabilised samples where all chemi- and photoluminescence had disappeared. To determine the percentage of injected 5-FU in the plasma, it was necessary to calculate the total plasma volume of each mouse (ml). The standard formula was:

Mouse Mass (g) × mouse blood volume $(0.07) \times$ plasma proportion of blood $(0.59)^1$ The percentage of injected 5-FU in the plasma was calculated by:

$$\frac{\text{Plasma volume (ml)} \times dpm/\text{ml plasma} \times 100}{\text{total } dpm \text{ injected}}$$

When possible urine was collected from the non-wettable plastic enclosures with a syringe and needle. The urine was cleared by centrifugation at 14,000 gav for 10 min. Its radioactive content was measured after the addition of 3 ml HiSafeII scintillant to samples ranging from 8-30 ul. Through the technical difficulties in accurately quantitating the volume of urine produced by each mouse the % of the injected 5-FU dose in the urine was calculated by the following formula:

$$\frac{\text{time of collection } (h) \times 42 \, \mu l^1 \times dpm/\mu l \text{ urine} \times 100}{\text{total } dpm \text{ injected}}$$

Once blood was taken, the mice were killed by cervical dislocation. Immediately after killing the mouse the tumour, liver, heart, spleen, bladder, left and right kidneys, uterus, lungs, stomach, intestines, brain and lymph nodes were excised and analysed for total radioactivity. The total radioactivity per tissue was determined by solubilising 100-400 mg of tissue in 3-6 ml of for 36 h, 22° C. On completion of solubilisation the tissue was counted after adding 10 ml of HiSafeII scintillant. The samples were counted as previously described to avoid chemiluminescence.

As shown in FIG. 12, there was a significant targeting effect when combining HA with 5-FU. The greatest relative increase in tumour retention of drug was observed at 10 min where the HA enhanced drug uptake by a factor of 2.42 (p=0.001, Students t-test). At 20 min and 30 min after administration of the HA/5-FU statistically significant increases in the tumour uptake of 5-FU was also noted, with increased drug uptake of 1.5 and 2-fold respectively (p<0.001, Students t-test). The other time points did not demonstrate a statistically significant difference between 5-FU administered as a sole agent versus co-injection with HA.

It was important to establish that metabolic organs such as the liver, spleen and kidneys did not experience a high level of drug targeting which could counter-act any positive aspects of increased tumour targeting. Table 7 lists the [$^3$H]5-FU uptake of each tissue at the various time points tested.

Figure 14A:
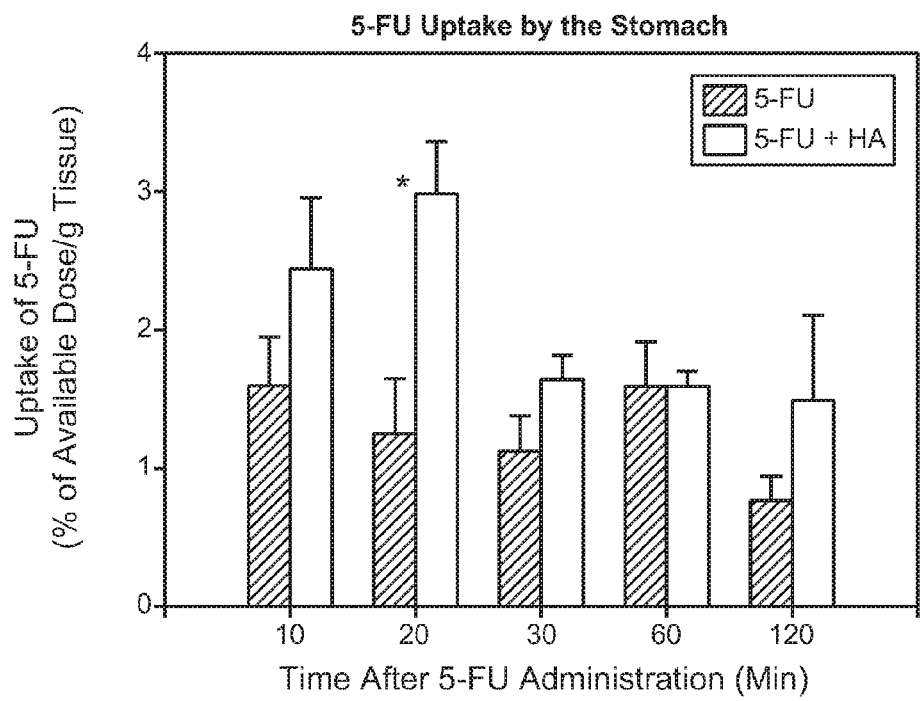
FIG. 14 shows increased uptake of 5-FU in the stomach, brain and lungs.
Figure 14B:
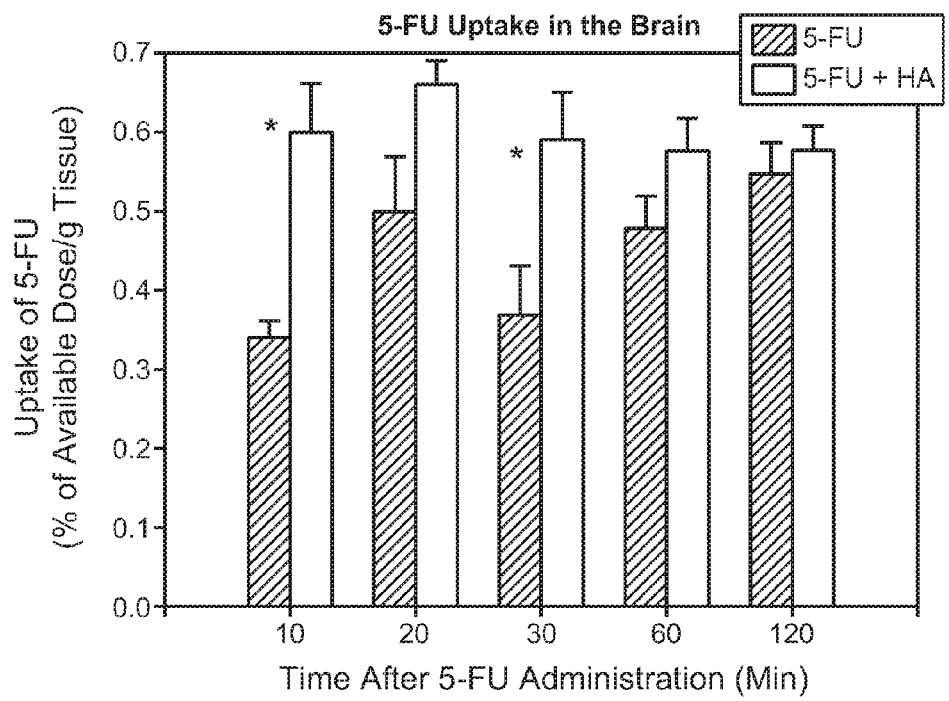
Figure 14C:
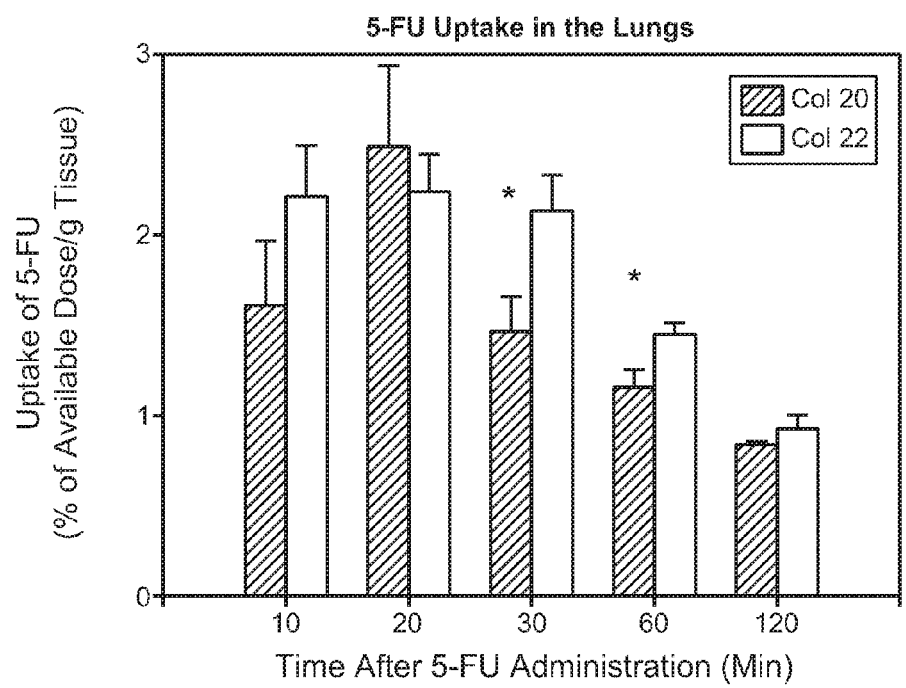

The stomach, brain and lungs did demonstrate increased 5-FU uptake at one or two sampling points. However, due to the small number of animals at each time point (n=5) it was not possible to substantiate statistical significance, even though a definite trend could be observed as shown in FIG. 14A-C.

At the later sampling points of 1 h and 2 h a significant decrease in cardiac 5-FU was noted, where co-administration with HA resulted in a decrease of 59% (p=0.003) and 53% (p=0.021) respectively.

It was not possible to collect urine from each mouse, through variations in the micturition rate; therefore insufficient urine was collected to enable statistical analysis.

Figure 15:
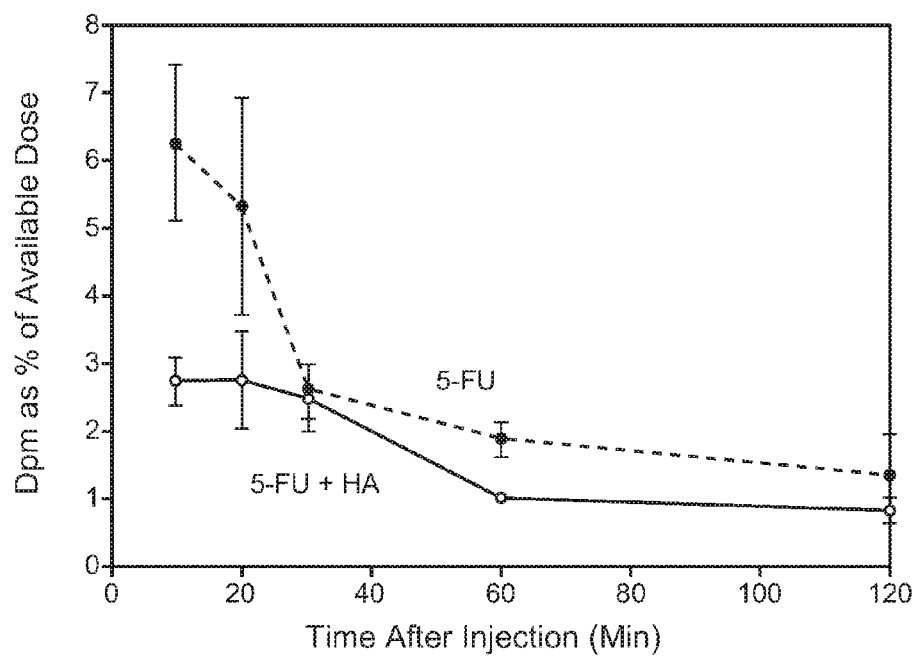
FIG. 15 shows the effect of HA on the pharmacokinetics elimination of plasma 5-FU.

When 5-FU was co-injected with HA there was an early decrease in the circulatory levels of 5-FU (Table 7). Hyaluronan reduced plasma 5-FU by 55% (p=0.001). The pharmacokinetic plasma half-life was altered from 28 min to 56 min in mice receiving 5-FU/HA as shown in FIG. 15.

TABLE 7

Effect of hyaluronan on the biodistribution of [$^3$H]5-Fluorouracil in nude mice bearing human breast carcinoma xenografts

| | 5-FU (mean % dose/g ± 1 SE, n = 5) | | | | | HA/5-FU (mean % dose/g ± 1 SE, n = 5) | | | | |
| --- | --- | --- | --- | --- | --- | --- | --- | --- | --- | --- |
| | 10 min | 20 min | 30 min | 1 h | 2 h | 10 min | 20 min | 30 min | 1 h | 2 h |
| Tumour | 1.49 ± 0.25 | 2.13 ± 0.28 | 1.20 ± 0.17 | 1.34 ± 0.1 | 1.35 ± 0.24 | 3.60 ± 0.35 | 3.20 ± 0.22 | 2.45 ± 0.14 | 1.85 ± 0.23 | 1.03 ± 0.12 |
| Liver | 19.64 ± 3.75 | 23.27 ± 1.6 | 15.86 ± 3.12 | 9.20 ± 1.83 | 3.64 ± 1.09 | 21.2 ± 1.81 | 21.37 ± 1.71 | 15.98 ± 1.68 | 8.73 ± 1.92 | 3.99 ± 1.24 |
| Spleen | 1.45 ± 0.28 | 1.71 ± 0.18 | 1.02 ± 0.13 | 1.02 ± 0.07 | 0.99 ± 0.09 | 1.94 ± 0.17 | 1.39 ± 0.12 | 1.17 ± 0.20 | 1.3 ± 0.19 | 1.21 ± 0.18 |
| Lymph Nodes | 2.04 ± 0.31 | 2.98 ± 0.78 | 1.49 ± 0.27 | 1.72 ± 0.46 | 0.88 ± 0.17 | 3.47 ± 0.61 | 2.99 ± 0.47 | 1.97 ± 0.22 | 1.85 ± 0.29 | 0.75 ± 0.12 |
| Kidneys | 5.15 ± 1.42 | 12.53 ± 2.37 | 10.12 ± 2.01 | 7.39 ± 1.12 | 3.97 ± 0.71 | 9.24 ± 0.91 | 14.56 ± 0.94 | 14.52 ± 1.56 | 10.72 ± 1.97 | 5.51 ± 0.98 |
| Bladder | 18.30 ± 3.98 | 40.34 ± 26.39 | 19.11 ± 10.76 | 33.69 ± 18.72 | 61.88 ± 39.1 | 13.31 ± 5.18 | 39.17 ± 20.74 | 37.95 ± 25.1 | 10.04 ± 5.53 | 6.05 ± 3.58 |
| Intestines | 1.33 ± 0.24 | 1.73 ± 0.42 | 2.39 ± 0.76 | 1.57 ± 0.23 | 2.44 ± 1.42 | 1.64 ± 0.28 | 2.06 ± 0.25 | 1.90 ± 0.08 | 1.30 ± .23 | 1.79 ± 0.62 |
| Stomach | 1.59 ± 0.35 | 1.25 ± 0.40 | 1.11 ± 0.26 | 1.58 ± 0.33 | 0.76 ± 0.18 | 2.44 ± 0.52 | 2.98 ± 0.38 | 1.63 ± 0.19 | 1.58 ± 0.11 | 1.48 ± 0.62 |
| Brain | 0.34 ± 0.02 | 0.50 ± 0.07 | 0.37 ± 0.06 | 0.48 ± 0.04 | 0.55 ± 0.04 | 0.60 ± 0.06 | 0.66 ± 0.03 | 0.59 ± 0.06 | 0.58 ± 0.04 | 0.58 ± 0.03 |
| Heart | 1.26 ± 0.21 | 1.51 ± 0.19 | 1.01 ± 0.11 | *0.81 ± 0.05* | *0.68 ± 0.08* | 1.67 ± 0.28 | 1.56 ± 0.11 | 1.03 ± 0.19 | *0.48 ± 0.10* | *0.36 ± 0.05* |
| Lungs | 1.61 ± 0.35 | 2.48 ± 0.45 | 1.46 ± 0.20 | 1.15 ± 0.10 | 0.84 ± 0.01 | 2.21 ± 0.27 | 2.23 ± 0.21 | 2.13 ± 0.19 | 1.45 ± 0.06 | 0.92 ± 0.07 |
| Bone | 1.37 ± 0.30 | 1.36 ± 0.13 | 0.86 ± 0.14 | 0.89 ± 0.06 | 0.86 ± 0.18 | 2.01 ± 0.07 | 1.78 ± 0.13 | 1.18 ± 0.09 | 1.08 ± 0.19 | 0.66 ± 0.05 |
| Uterus | 1.88 ± 0.42 | 2.52 ± 0.22 | 1.63 ± 0.24 | 1.51 ± 0.24 | 1.57 ± 0.60 | 3.38 ± 0.35 | 3.41 ± 0.47 | 2.17 ± 0.21 | 1.78 ± 0.28 | 1.36 ± 0.45 |
| Plasma | *6.26 ± 0.57* | *5.32 ± 0.08* | 2.59 ± 0.20 | *1.88 ± 0.13* | 1.36 ± 0.3 | *2.76 ± 0.18* | *2.76 ± 0.36* | 2.50 ± 0.28 | *1.01 ± 0.05* | 0.85 ± 0.09 |

*12 point bold* represents measurements where the co-administration of HA significantly reduced the 5-FU concentration (Students t-test)

▒ represents measurements where the co-administration of HA significantly increased the 5-FU concentration (Students t-test)

FIG. 13 shows that the primary metabolic organs of HA are the liver, lymph nodes and spleen, while 5-FU is extensively metabolised in the liver.

These organs did not exhibit a significant increase in 5-FU uptake when it was co-injected with HA. However, the kidneys did demonstrate a significant increase in 5-FU targeting at 10 min after administration (1.8-fold increase, p=0.04) with HA. After this point, even though, not statistically significant, this trend of enhanced drug uptake continued until the end of the sampling period.

The bladder, intestines and bone marrow did not demonstrate an increased uptake of 5-FU. In tissues such as the uterus there was a short-term increase in drug uptake at 10 min (1.8-fold increase, p=0.032), but no differences were demonstrated at other time points, so the significance of this observation must remain uncertain.

Example 10

Administration of Treatment Regimens to Mice

One of the most commonly used treatment regimens for human breast cancer is cyclophosphamide, methotrexate and 5-fluorouacil which is administered on day 1 and 8 of a 28 day cycle. In human breast cancer the initial treatment regimen is for 6 cycles at which time the patient condition is re-assessed, therefore we tried to simulate the human treatment regimen as closely as possible by exposing the mice to 6 cycles (6 months) of treatment in a long term efficacy study and a 6 cycles (6 week) short term efficacy study. Considering the life cycle of a mouse is approximately 2 years we commenced both short-term and long-term treatment protocols as shown in Table 8.

TABLE 8

Treatment Administration Protocols.

| Treatment Group | Dosage | 6-Week Study: Treatment Regimen Bolus injection on Days | 6-Month Study: Treatment Regimen |
|---|---|---|---|
| 1. Saline | 0.1 ml of 0.9% saline (injection grade) | 1 & 2 of 7 day cycle | 1 & 8 of 28 day cycle |
| 2. 5-FU/HA | 0.1 ml containing: 30 mg/kg 5-FU + 12.5 mg/kg HA | 1 & 2 of 7 day cycle | 1 & 8 of 28 day cycle |
| 3. HA | 0.1 ml containing: 12.5 mg/kg HA | 1 & 2 of 7 day cycle | 1 & 8 of 28 day cycle |
| 4. 5-FU | 0.1 ml containing: 30 mg/kg 5-FU | 1 & 2 of 7 day cycle | 1 & 8 of 28 day cycle |
| 5. HA followed by 5-FU | 0.1 ml containing: 12.5 mg/kg HA or 30 mg/kg 5-FU | 1: HA 2: 5-FU 3: HA 4: 5-FU of 7 day cycle | 1: HA 2: 5-FU 8: HA 9: 5-FU of 28 day cycle |
| 6. HA | 0.1 ml containing: 12.5 mg/kg HA | 1: HA 3: HA of 7 day cycle | |
| 7. 5-FU | 0.1 ml containing: 30 mg/kg 5-FU | 2: HA 4: HA of 7 day cycle | |

Mice were randomly divided into 7 groups of 8 animals per group for the short term study and 5 groups of 8 animals for the long term study (refer to Table 8 for dosage and treatment administration schedule).

The treatment was not extended over the 6 month regimen since it has been demonstrated that chemotherapy lasting more than six months has not generally been associated with greater benefit (Harris et al, 1992).

Animals were weighed and tumour volumes measured on the day of treatment application for long term study as described in Example 8. In the 6-week study animals were weighed and tumour volumes measured on a daily basis. Animals were individually placed in an injection box, and the injections were administered via the tail vein. It has been experimentally proven that stress can be a major factor in a patients response to chemotherapy (Shackney et al, 1978), therefore we ensured that equal numbers of mice were allocated to each cage, the animal number per cage varied from 5-8 depending on the stage of experimentation.

Figure 16A:
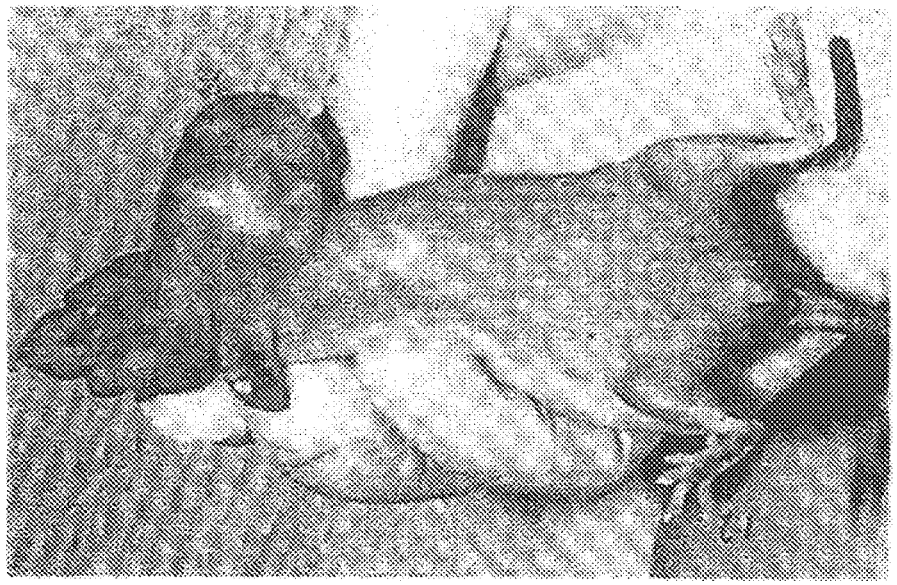
FIG. 16 shows the criteria for definition of experimental end-point. Criteria 2 (Panel A) and Criteria 3 (Panel B) are shown.
Figure 16B:
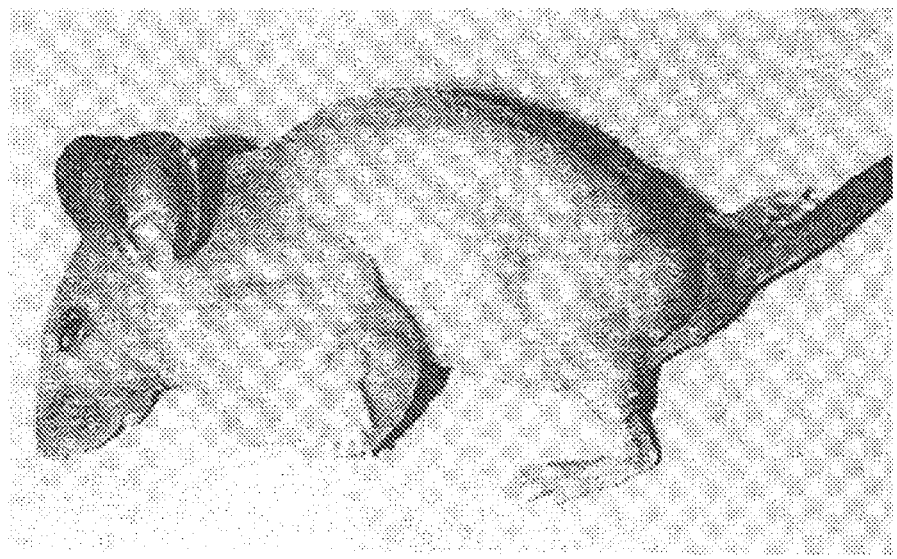

The experimental end-point occurred when the animal had to be euthanised due to degree of disease progression or when the 6 month (long term) or 6 week (short term) treatment regimen was completed. Due to the animal ethics guidelines the animals were monitored fortnightly by an independent animal ethics officer who assessed the degree of disease progression. As shown in FIG. 16, the following criteria were used to determine if an animal had reached the stage of experimental end-point of necessary death:

1). animal was not eating or drinking and had experienced dramatic weight loss;
2). tumour size was greater than 10% of body mass (Panel A);
3). tumour mass was so large the animal was immobilised (Panel B).

At the experimental end-point the animals were anaesthetised by a 0.1 ml intra-peritoneal injection of Nembutal (60 mg/ml), blood was collected followed by killing of the animals using cervical dislocation.

Figure 17:
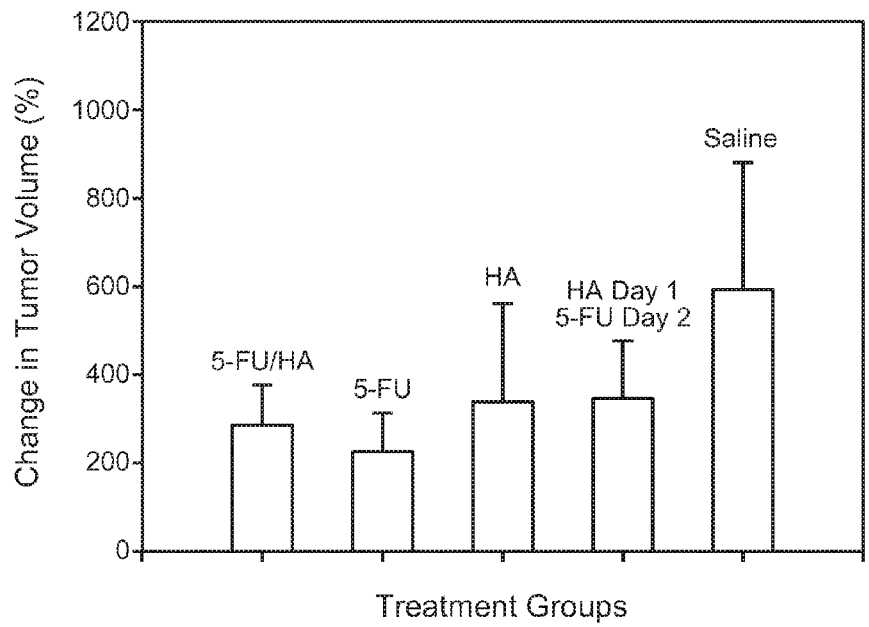
FIG. 17 shows the efficacy of 5-FU/HA adjuvant therapy (6 week treatment regimen): Effect on primary tumour volume.

At the end of the 6 week study tumour mass was determined and both the 5-FU and 5-FU/HA therapies had significantly smaller tumours than the saline group (p=0.005) as seen in FIG. 17. There was not a significant difference in tumour volume between the 5-FU and HA/5-FU treatment groups, indicating that both therapies displayed equal efficacy against the primary tumour. No statistical difference was noted between the primary tumour volume of saline and HA.

Immediately after killing the mouse the tumour, liver, heart, spleen, bladder, left and right kidneys, uterus, lungs, stomach, intestines, brain and lymph nodes were excised and placed in 4% formalin buffered with 0.06M phosphate pH 7.5, and cetylpyridinium chloride, 1.0% w/v. The tissue was fixed for 16-24 h before histological processing. Fixed tissue was dehydrated stepwise to 100% ethanol and embedded in paraffin blocks from which 2-4 µm sections were placed on glass microscope slides. Staining the tissue sections with a haematoxylin nuclear stain and eosin cytoplasmic stain highlighted any pathological features that could indicate treatment toxicity.

Nine to 11 lymph nodes were collected per animal, ensuring that all nodes which drained the tumour area were collected. There are currently two methods used for the detection of lymph node metastasis:

i) routine haematoxylin and eosin staining of gross organ structure
ii) immunohistochemistry using a cancer marker such as carcinoembryonic antigen Both methods of metastasis detection were employed in this study. Not all commercially available CEA antibodies react with human breast cancer cells, so we tested the reactivity of 5 different antibodies (DAKO, Amersham and KPL).

The haematoxylin and eosin stained lymph nodes were examined by Dr P. Allen (certified pathologist) where each node was microscopically examined for the presence of tumour cells. The CEA immunostained lymph nodes were microscopically examined, where any positively stained nodes were counted and considered positive for lymph node metastasis.

Tumour volume was monitored on a daily or weekly basis by calliper measurements and tumour volume calculated as previously described in example 8.

One of the most common toxic effects of 5-FU is on the gastro-intestinal tract where haemorrhagic enteritis and intestinal perforation can occur (Martindale, 1993). Animals were monitored daily for GI tract upset such as diarrhoea and weekly for more severe toxicity manifestations such as weight loss. Weight loss was monitored by calculating net body weight as estimated by subtracting tumour weight, which was calculated as 1 g×tumour volume ($cm^3$) as cited in Shibamoto et al, 1996. For demonstration of any weight changes the animal body weight was normalised to the body weight at the time of treatment commencement as:

$$\text{Body mass } (ex \text{ tumour}) - \frac{\text{body mass at commencement of treatment } (ex \text{ tumour})}{\text{Body mass at commencement of treatment } (ex \text{ tumour})} \times 100$$

Figure 18:
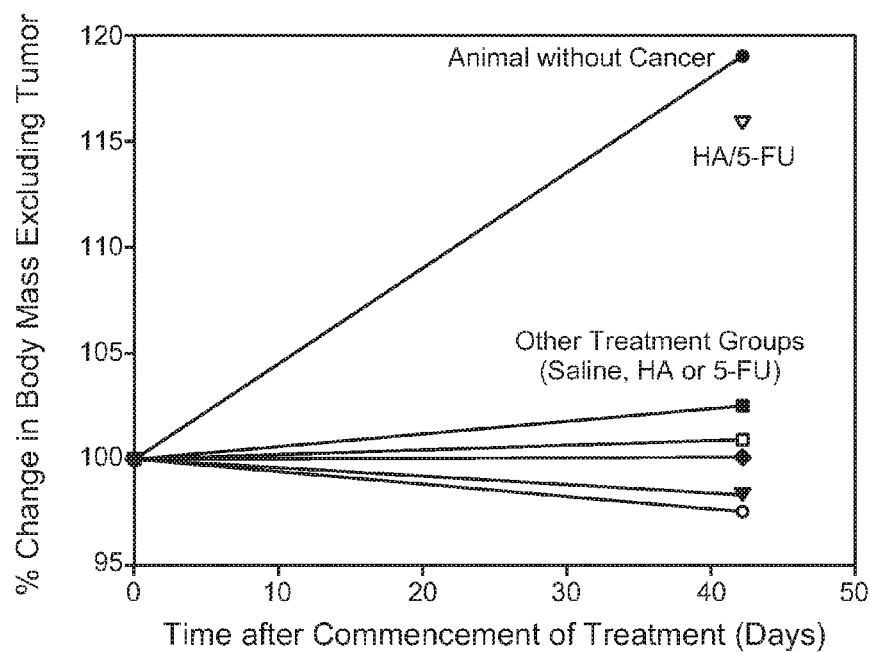
FIG. 18 shows the efficacy of 5-FU/HA adjuvant therapy (6 week treatment regimen): Effect on body mass.

No daily GI tract upset such as diarrhoea was noted in any of the animals regardless of treatment regimen. Severe gastro-intestinal toxicity for each treatment regimen was estimated using loss of body weight (excluding the tumour weight) as an indicator. At the time of death of each animal the percentage change in body mass was calculated as previously described. There was a statistically significant difference in the normalised body weight between the saline, HA, 5-FU treatment groups as compared to the 5-FU/HA group treatment group (FIG. 18). The mice receiving the 5-FU/HA adjuvant therapy demonstrated a 16% increase in body weight (students t-test, p=0.025) throughout the treatment in comparison to the untreated group which experienced a net increase of 2% in weight.

The combination of immunohistochemical detection of carcinoembryonic antigen (CEA) with classical diagnostic pathology provided an excellent quantitation of lymph node metastasis. The average mouse contains 15-19 lymph nodes (Lamszus et al, 1997), therefore this study examined approximately 60-70% of the animals lymph nodes. Careful procedure was followed to ensure that all nodes that drained the mammary fat pad and chest region were removed and examined. As demonstrated in Table 9A, all animals displayed lymph node metastasis.

Example 11

Long-Term Treatment: 6-Month Regimen

While this study is still on-going there are significant data being generated.

The TDT is the time taken (days) for a tumour to double in mass or cell number, a parameter of tumour growth which is simple to measure and can be easily related to clinical tumour behaviour in conceptional terms (Shackney et al, 1978). By monitoring the tumour doubling time it is often possible to evaluate tumour chemotherapeutic response, as slowly growing tumours tend to respond poorly to chemotherapy (Schabel, 1975).

The tumour doubling time for each treatment is shown in Table 9B.

TABLE 9A

The Effect of 5-FU/HA Adjuvant Therapy on the Growth and Metastasis of Human Breast Cancer Xenografts in Nude Mice: 6-Week Study

| Treatment Group | TDT Mean ± SEM | % of animals with lymph node metastasis | Number of new tumours | % of lymph node involved per animal mean ± SEM | Number of animal completing treatment | % change in body weight mean ± SEM |
| --- | --- | --- | --- | --- | --- | --- |
| 1. Saline | 9.4 ± 1.1 | 100 | 3 | 94.2 ± 2.8 | 8/8 | 100.1 ± 0.61 |
| 2. 5-FU/HA | 20.9 ± 2.7 | 100 | 0 | 12.1 ± 0.9 | 8/8 | 116.0 ± 0.56 |
| 3. HA D1,2 | 27.7 ± 5.2 | 100 | 0 | 18 ± 4.1 | 8/8 | 102.5 ± 0.38 |
| 4. 5-FU D1,2 | 32.1 ± 3.5 | 100 | 1 | 14.3 ± 2.9 | 8/8 | 97.5 ± 0.73 |
| 5. HA followed by 5-FU | 14.8 ± 3.7 | To be assessed | To be assessed | To be assessed | 8/8 | 101.8 ± 0.93 |
| 6. HA D1,3 | 30.7 ± 4.9 | To be assessed | To be assessed | To be assessed | 8/8 | 100.9 ± 0.56 |
| 7. 5-FU D 2, 4 | 15.3 ± 2.5 | To be assessed | To be assessed | To be assessed | 8/8 | 98.3 ± 0.73 |

Figure 19A:
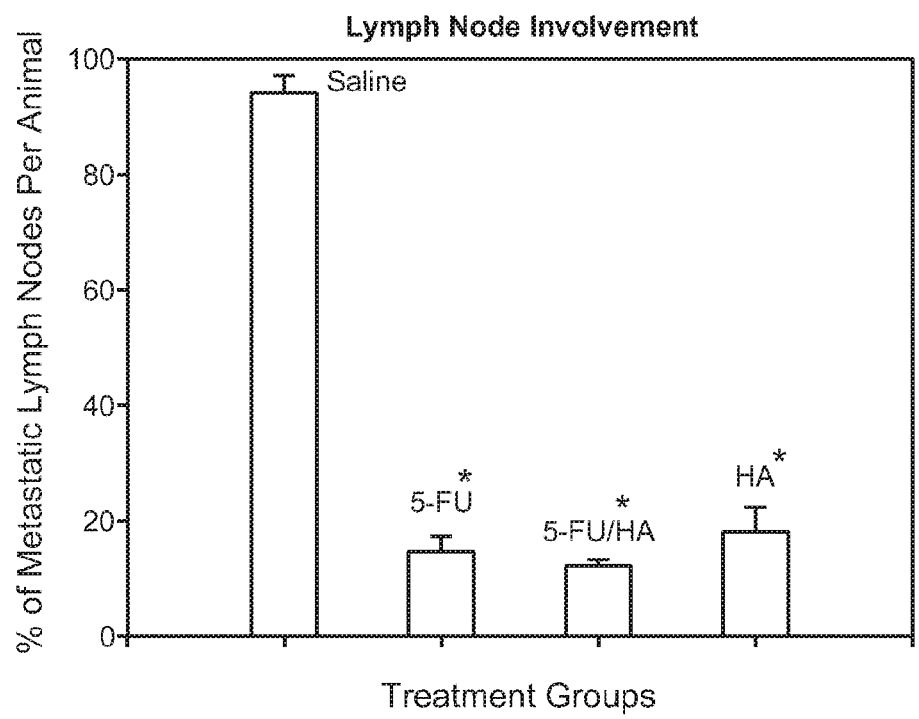
FIG. 19 shows the efficacy of 5-FU/HA adjuvant therapy (6 week treatment regimen): Effect on spread of cancer lymph nodes and formation of new tumours.

FIG. 19A shows that the percentage of lymph node involvement (number of metastatic nodes per animal) was greatly affected by 5-FU, 5-FU/HA and HA treatment, where the saline group demonstrated a 6-fold increase in the amount of lymph node involvement. Once again, HA demonstrated that it could have therapeutic value.

Figure 19B:
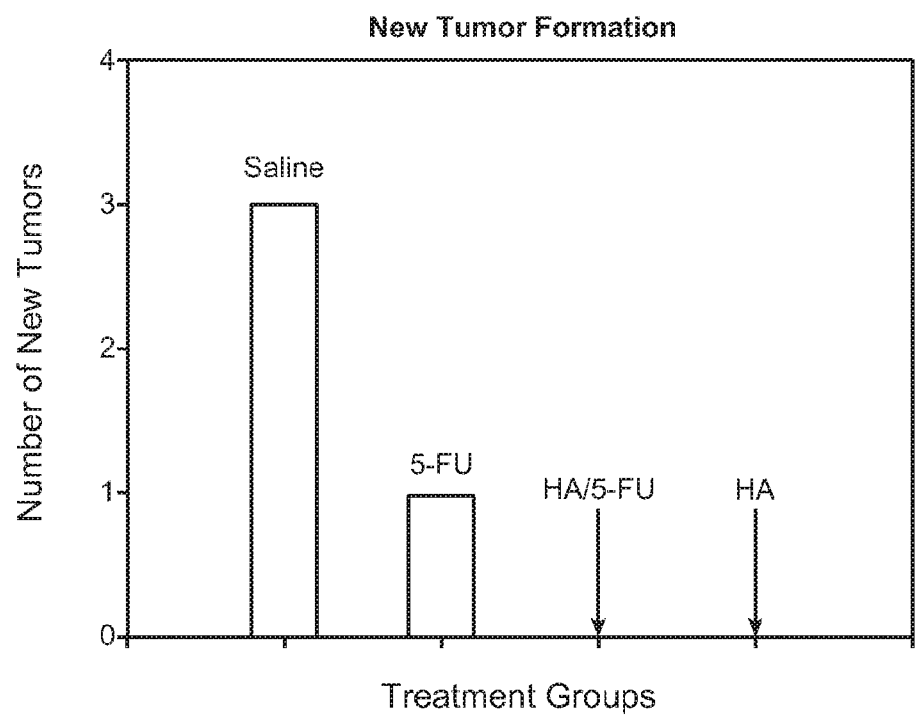

While dissecting the animal at the end of the study every tissue was microscopically and macroscopically examined for tumour nodules. With the exception of the mice receiving the HA/5-FU or HA therapy, new tumours were observed around the neck or underarm region of the area adjacent to the primary tumour. The incorporation of HA into the treatment regimen inhibited new tumour formation, as shown in FIG. 19B.

There was not a significant difference in overall patient survival regardless of treatment (Table 9A), where animals from all groups completed the treatment regimens.

As one of the major toxicities associated with 5-FU treatment is depression of the bone marrow and subsequent drop in white blood cells it was necessary to assess any treatment associated blood toxicity. Upon anaesthetising the animals, blood was collected from the heart or great vessels using a needle and syringe. Estimation of white blood cell number by making a 1/10 dilution of blood in mouse tenacity saline (M) and counting it on a haemocytometer. A differential blood count was performed by counting neutrophils, lymphocytes, and erythrocytes. The total estimation of blood cell subpopulations was compared to published data for mouse blood.

To ensure that treatments did not induce organ atrophy or enlargement, the organs were removed and weighed during the post mortem. The mass of each organ was calculated as a % of the overall net body weight, and compared to the organ masses of the saline only group (Group 1).

TABLE 9B

The Effect of 5-FU/HA Adjuvant Therapy on the Growth and Metastasis of Human Breast Cancer Xenografts in Nude Mice: 6-Month Study

| Treatment | TDT Mean ± SEM | Experimental endpoint | Tumour pathology: Observations |
| --- | --- | --- | --- |
| Saline | 13.0 ± 4.0 | 87.5% immobilsed 12.5% metabolic stress | No specific characteristics |
| 5-FU | 22.7 ± 2.9 | 62.5% immobilsed 37.5% metabolic stress | No specific characteristics |
| 5-FU/HA | 28 ± 2.6 | 25% immobilsed 75% metabolic stress | Small areas of necrosis appeared, followed by large areas of scab formation. ⅔ tumours fully necrosed and "dropped off" |
| HA | 26 ± 1.75 | 100% immobilsed | Small areas of necrosis and scab formation |
| HA followed by 5-FU | 13.5 ± 0.63 | 37.5% immobilsed 62.5% metabolic stress | No specific characteristics |

There was not a significant difference in TDT between the 5-FU/HA and 5-FU treatment. As with the 6-week study, the administration of HA also demonstrated a therapeutic effect on the primary tumour, demonstrating a TDT of 26±1.75 versus the saline of 13±4 days. The administration of HA 24 h before 5-FU appeared to counteract any therapeutic value of 5-FU in relation to retardation of tumour growth.

Tumour mass and volume are useful parameters in monitoring tumour treatment response and progression, but do not ultimately demonstrate the cytotoxic effects rendered by a therapy. We wanted to establish if the HA/5-FU therapy killed more tumour cells and the location of the cells. Dying cells can be pathologically manifested by:
i). disintegration of the nucleus (apoptosis)
ii). lysis of the cell (necrosis)

Scanning the entire tumour image into an MCID computer that calculated the entire tumour area quantitated the number of dying cells. The cells with fragmented nuclei or lysed cells were outlined and scanned, these areas which are then digitised and the exact area of dying cells calculated. The percentage of the tumour attributed to dead cells was calculated by:

$$\frac{\text{area of apoptotic and necrotic cells} \times 100}{\text{area of entire breast tumour}}$$

A viable cell contains more water than a dying or dead cell, therefore by determining the ratio of dry tumour mass to wet tumour mass it is possible to estimate the overall area of viable versus non-viable cells. The tumours were dissected bilaterally where half was processed for tumour pathology and the remaining half was weighed before and after drying at 50° C. for 48 h. The dry mass as a percentage of wet tumour mass was calculated by:

$$\frac{\text{Dry tumour mass} \times 100}{\text{Mass of wet breast tumour}}$$

The overall patient survival time was calculated as the time (days or weeks) that the animal lived after the commencement of treatment.

The tumour doubling time for each treatment is shown in Table 9A. There was not a significant difference in TDT between the 5-FU/HA and 5-FU treatments. However, the administration of HA demonstrated a therapeutic effect on the primary tumour, where the TDT was significantly greater than the saline group (p, 0.05, Multiple comparison Tukey test). The administration of HA 24 before 5-FU appeared to counteract any therapeutic value of 5-FU in relation to retardation of tumour growth.

Figure 20A:
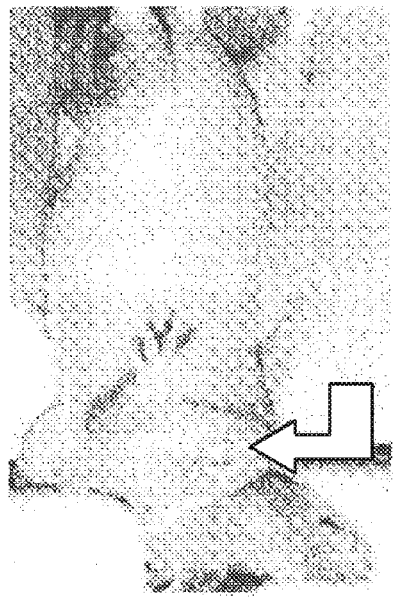
FIG. 20 shows the general appearance of tumours of the 6 month efficacy study.
Figure 20B:
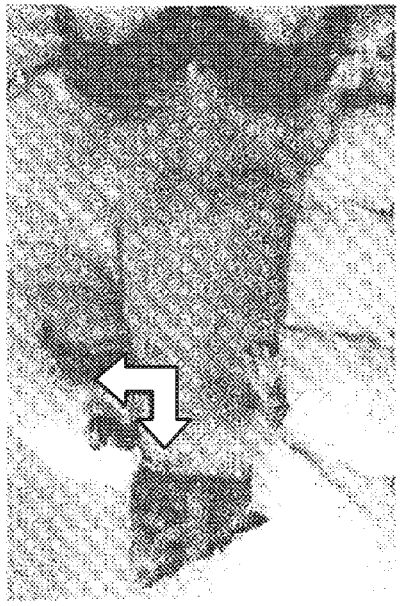
Figure 20C:
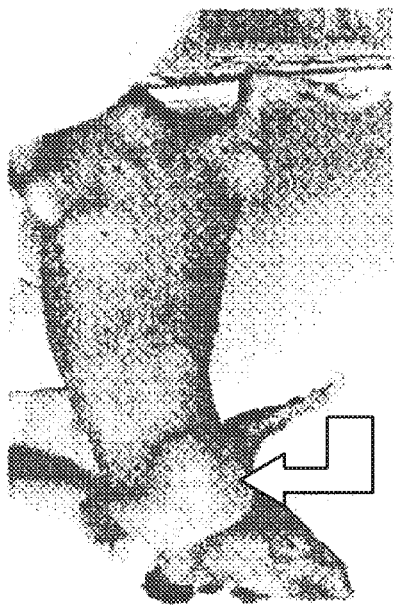
Figure 20D:
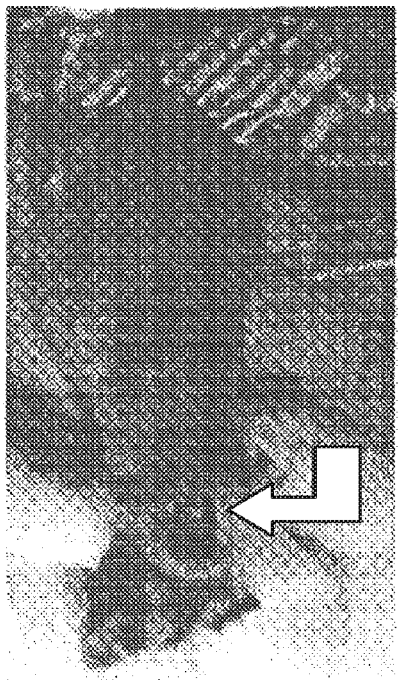

The cited cure rate for 5-FU is 26% (Inaba et al, 1989), but the animals receiving 5-FU did not experience a "cure". Two mice receiving the HA/5-FU adjuvant therapy experienced a "cure" where the tumours fully necrosed and dropped off after approximately 12 weeks of treatment. FIG. 20B shows the characteristic appearance of small scab formation on mice receiving treatment with HA and HA/5-FU, while FIG. 20C shows the appearance of small areas of necrosis followed by the formation of a large area of scab. One of the mice experienced the re-growth of a small nodule, but the second mouse was still tumour free at 22 weeks. As seen in FIG. 20A, mice receiving 5-FU or saline had large tumours that ultimately ended with the animal dying due to mass of tumour burden (Table 9B), but mice receiving HA±5-FU displayed a characteristic tumour appearance, where a small area necrosed followed by the formation of a scab.

At week 22, 37.5% of the 5-FU/HA mice were still surviving, and the major cause of death for the 5-FU/HA adjuvant therapy mice was loss of weight and metabolic stress (Table 9B).

Figure 21:
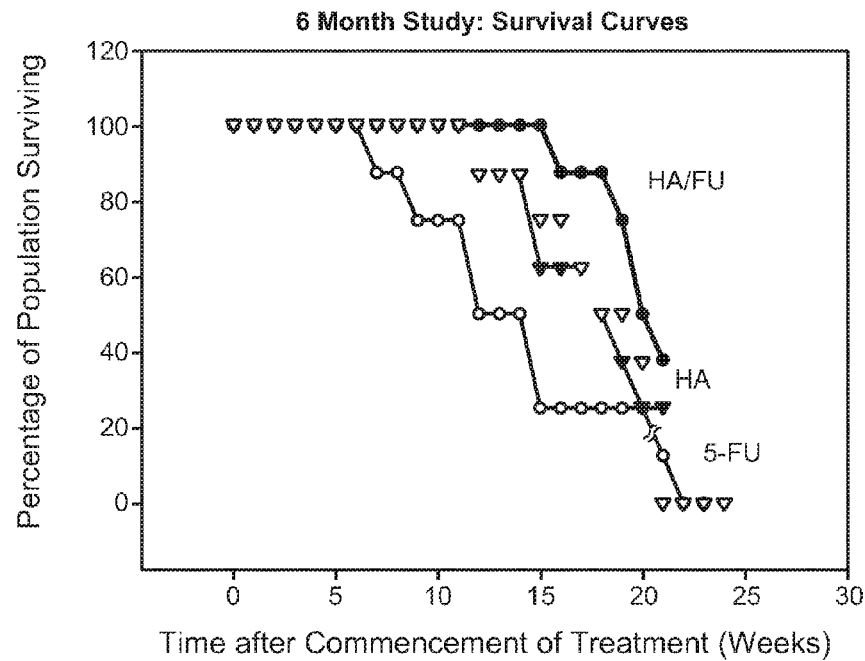
FIG. 21 shows the effect of HA/5-FU adjuvant therapy on patient survival.

There appears to be a significant difference in overall patient survival when HA±5-FU is administered to mice bearing human breast cancer xenografts. At week 22 of a 24 week study the only surviving groups are the 5-FU/HA and HA groups, as shown in FIG. 21.

Conclusions

The data from the 5-FU targeting show that there was a statistically significant increase in 5-FU uptake by tumours when 5-FU was injection with HA at the time points 10, 20 and 30 minutes with a 2.4, 1.5 and 2 fold increase respectively in 5-FU uptake (Table 7). This indicated that 5-FU was being targeted to the tumour by the HA. There are two possible mechanisms of HA targeting of 5-FU to tumour cells:

HA containing associated 5-FU binds to the receptors (CD44) and is internalised via receptor-mediated endocytosis, so releasing the drug into the tumour cell.

The HA molecular mesh will act as an impedance to outward diffusion, so that after HA binds to receptors (CD 44 and RHAMM), the entrained 5-FU is able to diffuse into the tumour cells. While held at the surface of the cells by the HA matrix the 5-FU has increased availability to the active transport mechanism normally utilised for 5-FU transport into the underlying cell.

The catabolism of HA mainly occurs in the lymph nodes (Fraser et al, 1988) and the liver (Laurent et al, 1986). HA is normally cleared from the blood stream by receptor-mediated cellular uptake and catabolism in the liver (80-90%), kidneys (10%), spleen (0.1%) and bone marrow (0.1%)." (Fraser et al, 1983). Circulating HA is taken up by the metabolic receptor, also known as the liver endothelial cell (LEC) receptor (Eriksson et al, 1983), whereas the CD44 receptor appears to be involved with HA internalisation associated with cellular processes instead of metabolism, while the RHAMM receptor is only involved in cell motility. Combining HA with 5-FU could result in high levels of 5-FU being targeted to the sites of HA or 5-FU metabolism. The data from the targeting experiments (Table 6) shows that there was no significant increase in 5-FU targeting to the liver when administered with HA. As no observed increased targeting to the liver was observed it could suggest that the LEC receptor on the liver might have a lower binding affinity for HA in comparison to the CD44 receptor. Another possibility is that the CD44 isoform expressed on liver cells (Stamenkovic et al, 1991) does not bind HA with a high affinity. As with the liver no increased targeting of 5-FU was noted in the other metabolic organs of the spleen, bone marrow and lymph nodes.

There was a significant 1.8 fold increase in 5-FU targeted to the kidneys within a 10 min time frame. Although the other four time points did not show a significant increase in 5-FU uptake by the kidney when HA/5-FU was co-administered, there appeared to be a general trend occurring, where more 5-FU delivered to the kidneys on administration with HA. The main pathway for the final elimination of 5-FU from the body is urinary excretion. Even though there seems to be little increase in renal content of the drug with HA, but we believe from other evidence that HA is taken up and catabolised-very quickly by the kidneys so that its residence time would be short and associated drug would be quickly released into the urine.

In tissues such as the stomach, brain, lungs and uterus short-term targeting was noted at one or more time points. No consistent pharmacokinetic patterns were generated, which could indicate that we need to increase the population sample number, which could definitively indicate if these observations are genuine. In the case of the increased targeting to the brain at 10-30 min this could be explained by the previous observation that. HA has been associated with enhancing the ability of drugs to cross the blood-brain barrier (Nelson & Falk, 1994).

There was a significant increase levels of 5-FU in the lungs on administration with HA at the time points min and 1 h. It has been reported that lung macrophages contain high levels of the HA-binding, CD44 isoform (Underhill et al 1993), which could account for the increased targeting. This could be associated with a therapeutic advantage in the treatment of carcinoma of the lung, where small and large cell lung carcinomas have been reported to contain an over expression of CD44 and RHAMM (Horst et al, 1990).

The was a significant decrease in 5-FU targeted to the heart at the 1 and 2 h time points when HA was co-injected with 5-FU. As 5-FU administration can result in cardiotoxicity (MIMS, 1997) administration of 5-FU with HA may reduce the degree of toxicity to the heart compared to when 5-FU is administered alone.

When evaluating the therapeutic efficacy of the HA/5-FU adjuvant therapy several observations were consistent throughout both the long and short-term treatment protocols.

Mice receiving HA/5-FU or HA alone appeared to have more energy and maintain or increase body mass, observations supported by the increased survival times of HA/5-FU mice in the 6-month study Tumours of mice receiving 5-FU/HA or HA developed areas of external necrosis, to the extent where 2 tumours dropped off The addition of HA to 5-FU did not appear to have a significant effect on the volume of the primary treatment when the therapy was administered for 6 weeks, but this could be due to the vasculature of the tumour. Tumours consist of three areas. When HA was administered with and without 5-FU it would reach the tumour, enter the well vascularised and semi-necrotic areas via the large gap junctions of the damaged blood vessels. Due to the ability of HA to absorb water this could result in an influx in extracellular fluid to the necrotic area of the tumour, subsequently increasing the volume of the tumour and causing further damage to tumour vasculature. This hypothesis is consistent with the observation that tumours treated with HA±5-FU did routinely demonstrate necrosis and leakage of tumour intracellular fluid. When the calculation of the necrotic versus viable cell areas and the dry:wet mass ratio is completed we will be able to verify this hypothesis.

The long-term efficacy study showed an increased survival rate for mice receiving HA/5-FU treatment as shown in FIG. 21. The mean tumour volume of these mice also appeared to be reduced compared to the other treatment group. It was also noted in the long term study that the cause of death for the HA/5-FU group was mostly due to metabolic stress whereas cause of death for the 5-FU group was due more to immobilisation due to tumour size being to large. All the HA only mice died from immobilisation due to the tumour being too large not due to toxicity. Thus HA does not appear to have any toxicity effects was administered. From the targeting results it was found that increased targeting of 5-FU was occurring when combining HA with 5-FU to the tumour (FIG. 12). The ability of HA to target 5-FU to the tumour via HA binding to the HA specific receptors CD44 and RHAMM, which have been showed to be present in increased amounts at tumours sites (Culty et al, 1994; Wang et al 1996), may reflect that the use of HA with 5-FU and other cytotoxic drugs may help overcome the problem of not enough drug reaching the tumour to have any therapeutic impact. It was also found that in the short term study that the 5-FU/HA mice showed a significantly increase in body mass compared to all other groups (FIG. 21). Consequently the targeting ability of HA to tumour sites may decrease the amount of 5-FU going to other organs such as the intestines and in so doing reduce treatment side effects associated with 5-FU therapy in particularly gastrointestinal toxicity.

In comparison to the earlier evaluation of MTX/HA adjuvant therapy disclosed in examples 1 to 3, we noted some distinct common results and differences as summarised Table 10.

TABLE 10

Common Results And Differences Between Adjuvant Therapy With MTX/HA And 5-FU/HA

| Study | Similar Results | Different Results |
|---|---|---|
| MTX/HA: 6-month VS 5-FU/HA: 6-week | Mice receiving HA/drug experienced significant weight gain; No marked increase in patient survival; Inhibited formation of new tumours; Demonstrated a longer TDT; Reduced lymph node metastasis | |
| MTX/HA 6-month VS 5-FU/HA 6-month | Demonstrated, a longer TDT | 5-FU/HA mice demonstrate increased survival |
| HA control for MTX/HA: 6 month VS HA control for 5-FU/HA: 6 week & 6 month | | HA mice in the 5-FU/HA study demonstrated that HA exerted a therapeutic effect by reducing TDT; HA reduced lymph node metastasis and tumour formation. |

The main difference in the two studies was the starting mass of the tumours, where in the MTX/HA study the mean tumour volume 175.13 mm$^3$ compared to 61.63 mm$^3$ in the 5-FU/HA study. Through the dynamics of particle movement in to tumours and the response of a patient to the tumour bulk, this could account for the different results obtained in relation to the TDT estimations.

Example 12

Therapeutic Efficacy of Combination Therapy With Hyaluronan

One of the most commonly used treatment regimens for human primary and metastatic breast cancer is combination chemotherapy with cyclophospamide (Cyc), MTX and 55-FU which is administered on day 1 and 8 of a 28 day cycle. The combination therapy, often called CMF, is usually given in 6 cycles at which time the patient condition is re-assessed. The antitumour response rate with CMF therapy has been reported to be approximately 50% (Bonadonna, 1981; Bonadonna, 1988), but the therapy has many associated side-effects such as fatigue, nausea, leukopenia and vomiting (Bonadonna, 1976; Meyerowitz, 1979). Due to the success of utilising HA as a drug delivery vehicle for both MTX and 5-FU we evaluated the therapeutic efficacy and toxicity of the HA/CMF adjuvant therapy over a 6-week and 6-month treatment regimen.

The MTX and 5-FU were prepared as previously described in Examples 2 and 6, respectively. The stock concentration of Cyc was prepared by dissolving 1 g of lyophilized drug in 1 ml of injection grade pyrogen free distilled water and made up to 50 ml with injection grade 0.9% sodium chloride. The stock solution was aliquoted into small volumes and frozen at −20° C. until used.

A CMF injection was prepared by taking the appropriate volume of the drug stock solution to achieve the final drug concentrations of:

| | |
|---|---|
| 30 mg/kg 5-FU | (Stock solution: 20 mg/ml) |
| 15 mg/kg MTX | (Stock solution: 24.5 mg/ml) |
| 26 mg/kg Cyc | (Stock solution: 20 mg/ml) |
| 12.5 mg/kg HA | (Stock solution: 10 mg/ml) |

To establish the therapeutic efficacy and any possible toxicities of the CMF/HA adjuvant therapy, human breast tumour xenografts in nude mice were utilized. To simulate the human treatment regimen as closely as possible, mice were treated in 6 cycles (6 months) of treatment in a long term efficacy study and a 6 cycles (6 week) short term efficacy study. Mice were randomly divided into 7 groups of 8 animals per group for the short term study and 5 groups of 8 animals for the long term study.

Mice were treated with 30 mg/kg 5-FU; 15 mg/kg MTX; 26 mg/kg Cyc±12.5 mg/kg on either days 1 and 2 of a 7 day regimen for 6 weeks, or on days 1 and 8 of a 28 day regimen for 6 months. Control groups consisted of the administration of saline, 12.5 mg/kg HA or mice who had 12.5 mg/kg HA day 1 followed by CMF on day 2. Mice were monitored daily for any treatment toxicity and tumour mass was measured on a daily or weekly basis (see Table 11).

TABLE 11

| Treatment Administration Protocols | | | |
|---|---|---|---|
| Treatment Group | Dosage | 6-Week Study: Treatment Regimen Bolus injection on Days | 6-Month Study: Treatment Regimen |
| 1. Saline | 0.1 ml of 0.9% saline (injection grade) | 1 & 2 of 7 day cycle | 1 & 8 of 28 day cycle |
| 2. CMF/HA | 0.1 ml containing: 30 mg/kg 5-FU 15 mg/kg MTX 26 mg/kg Cyc + 12.5 mg/kg HA | 1 & 2 of 7 day cycle | 1 & 8 of 28 day cycle |
| 3. HA | 0.1 ml containing: 12.5 mg/kg HA | 1 & 2 of 7 day cycle | 1 & 8 of 28 day cycle |
| 4. CMF | 0.1 ml containing: 30 mg/kg 5-FU 15 mg/kg MTX 26 mg/kg Cyc | 1 & 2 of 7 day cycle | 1 & 8 of 28 day cycle |
| 5. HA followed by CMF | 0.1 ml containing: 12.5 mg/kg HA or .30 mg/kg 5-FU 15 mg/kg MTX 26 mg/kg Cyc | 1: HA 2: CMF 3: HA 4: CMF of 7 day cycle | 1: HA 2: CMF 8: HA 9: CMF of 28 day cycle |
| 6. HA | 0.1 ml containing: 12.5 mg/kg HA | 1: HA 3: HA of 7 day cycle | |

As shown in Tables 12a and 12b, in the 6-week study the following was observed:

1). Mice receiving a treatment regimen containing HA (CMF/HA, HA followed by CMF or HA only) displayed an increased survival of 50% over the CMF only group. The mean survival time for the CMF treatment group was 40.4 days versus 42 for all of the other groups.

Figure 22:
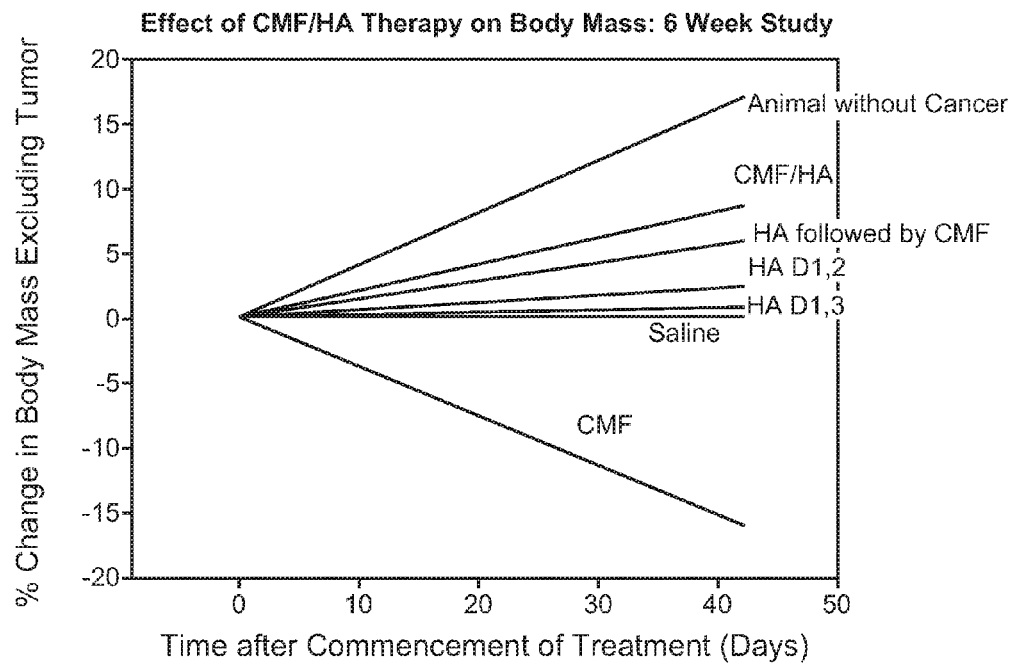
FIG. 22 shows the % change in body mass in mice treated with CMF/HA therapy over a 6-week period.

2). Animals treated with a combination of HA and CMF all demonstrated a significant weight gain (t-test, $p<0.001$) over animals treated with CMF only or HA only and demonstrated an enhanced well being. (see FIG. 22).

Figure 23:
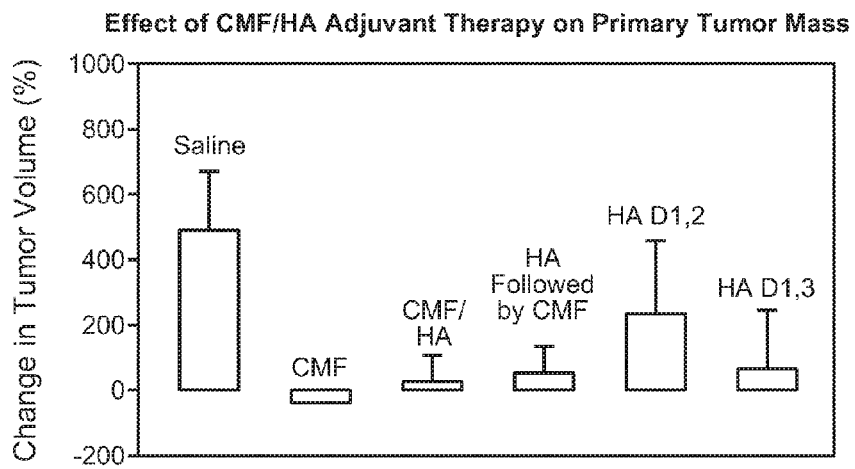
FIG. 23 shows the % change in tumour volume in mice treated with CMF/HA therapy over a 6-week period.

3). Tumour doubling time of the saline treated mice (no treatment control group) was significantly less than the other treatment groups (t-test, $p<0.001$), but there was no statistically significant difference between the other treatment groups (see FIG. 23).

4). There was a significant difference (t-test, $p=<0.001$) between CMF and CMF/HA treatment groups with regard to the end-point volumes of the primary tumours, where CMF resulted in a reduction in tumour mass in 7/8 animals, while CMF/HA reduced primary tumour bulk in only 3/8 animals.

5). No treatment toxicities were noted when mice were treated with HA±CMF, while mice treated with CMF only demonstrated signs of fatigue, conjunctivitis, general poor health.

When the CMF/HA or HA therapy was administered on day 1 and 8 of a 28 day cycle, the following was observed; There was not a significant difference in survival times between treatment groups 1). There was not a significant difference in weight gain between treatment groups.

2). The primary tumour of mice receiving HA±CMF exhibited small areas of necrosis and scab formation 3). In the treatment of the primary tumour, CMF as a sole agent did not demonstrate therapeutic efficacy over the saline and HA treatments. The addition of HA to CMF

TABLE 12A

The Effect Of CMF/HA Adjuvant Therapy On The Growth And Metastasis Of Human Breast Cancer Xenografts In Nude Mice: 6-Week Study

| Treatment Group | TDT Mean ± SEM | % of animals with lymph node metastasis | Number of new tumours | % of lymph node involved per animal mean ± SEM | Change in primary tumour volume (% of original tumour volume) mean ± SEM | Survival time (Days) mean ± SEM | Number of animals completing treatment | % change in body weight mean ± SEM |
|---|---|---|---|---|---|---|---|---|
| 1. Saline | 9.4 ± 1.1 | 100 | 3 | 94.2 ± 2.8 | 494.7 ± 101.6 | 42 ± 0 | 8/8 | 100.1 ± 0.61 |
| 2. CMF/HA | 29.3 ± 6.2 | N/A | N/A | N/A | 30.2 ± 26.5 | 42 ± 0 | 8/8 | 108.7 ± 0.62 |
| 3. HA D1,2 | 27.7 ± 5.2 | 100 | 0 | 18 ± 4.1 | 238.0 ± 77.6 | 42 ± 0 | 8/8 | 102.5 ± 0.38 |
| 4. CMF D1,2 | 37.6 ± 4.4 | N/A | N/A | N/A | −46.2 ± 12.0 | 40.4 ± 0.68 | 4/8 | 84.5 ± 1.37 |

TABLE 12A-continued

The Effect Of CMF/HA Adjuvant Therapy On The Growth And
Metastasis Of Human Breast Cancer Xenografts In Nude Mice: 6-Week Study

| Treatment Group | TDT Mean ± SEM | % of animals with lymph node metastasis | Number of new tumours | % of lymph node involved per animal mean ± SEM | Change in primary tumour volume (% of original tumour volume) mean ± SEM | Survival time (Days) mean ± SEM | Number of animals completing treatment | % change in body weight mean ± SEM |
|---|---|---|---|---|---|---|---|---|
| 5. HA followed by CMF | 21.8 ± 5.8 | N/A | N/A | N/A | 55.6 ± 26.6 | 42 ± 0 | 8/8 | 106 ± 0.51 |
| 6. HA D1,3 | 30.7 ± 4.9 | N/A | N/A | N/A | 66.1 ± 30.0 | 42 ± 0 | 8/8 | 100.9 ± 0.56 |

TABLE 12B

The Effect Of CMF/HA Adjuvant Therapy On The Growth And
Metastasis Of Human Breast Cancer Xenografts In Nude Mice; 6-Month Study

| Treatment | TDT Mean ± SEM | Survival Time Mean Weeks ± SEM | % of original body mass at experimental end-point Mean ± SEM | Primary tumour volume change (% of original tumour volume) mean ± SEM | Experimental endpoint | Tumour pathology: Observations |
|---|---|---|---|---|---|---|
| Saline | 14.8 ± 1.1 | 18.1 ± 0.39 | 98.569 ± 3.31 | 494.7 ± 101.6 | 87.5% immobilised 12.5% metabolic stress | No specific characteristics |
| CMF | 40.1 ± 4.0 | 10.5 ± 0.33 | 90.9 ± 5.44 | 392.8 ± 129.6 | 100% metabolic stress | No specific characteristics |
| CMF/HA | 23.5 ± 1.4 | 12.6 ± 0.21 | 93.6 ± 4.92 | 2100.5 ± 564.6 | 100% metabolic stress | Small areas of necrosis by week 11 on 2/8 mice; then large areas of scab formation. |
| HA | 24.7 ± 0.7 | 18.1 ± 0.45 | 104.6 ± 4.45 | 1929.1 ± 661.0 | 100% immobilised | Small areas of necrosis & scab formation |
| | | | | 55.6 ± 26.6 | | |
| | | | | 66.1 ± 30.0 | | | resulted in significantly larger (t-test, p=0.001) primary tumours.

The following conclusions can be drawn from this study:
1). The long-term administration (6-month) of HA/CMF adjuvant therapy does not demonstrate an increase in therapeutic efficacy or a reduction in treatment side-effects.
2). A short-term administration (6-week) administration of HA/CMF adjuvant therapy demonstrates numerous advantages over the administration of CMF as a sole treatment.
3). Significant weight gain.
4). 50% increase in number of animals completing treatment
5). Abolition of side-effects such as fatigue, conjunctivitis, loss of appetite
6). Mice receiving HA did not exhibit any signs of toxicity.

Example 13

NMR Investigations of the Nature of the Interaction of Chemotherapeutic Drugs and HA To further investigate the nature of the interaction between HA and chemotherapeutic drugs 1H Nuclear Magnetic Resonance (NMR) spectroscopy was used. Deuterium oxide ($^2H_2O$ (99.96%)) was obtained from Cambridge Isotope Laboratories. MTX was obtained from Faulding Pharmaceuticals and 5-FU and HA stock solutions were prepared as described previously.

Spectra were recorded at 298 K on a Brüker DRX spectrometer operating at 600 MHz with a shielded gradient unit. The 2D experiments were recorded in phase-sensitive mode using time-proportional phase incrementation for quadrature detection in the $t_1$ dimension (Marion & Wüthrich, 1983). The 2D experiments included TOCSY sequence using a MLEV-17 spin lock sequence (Bax & Davis, 1985) with a mixing time of 120 ms; NOESY (Kumar et al., 1980) with mixing times of 250 and 400 ms and ROESY spectrum with a mixing time of 250 ms. Temperature calibration of the probe was achieved by comparison to ethylene glycol chemical shifts. All chemical shifts (ppm) were referenced to the methyl resonance of 4,4-dimethyl-4-silapentane-1-sulfonate (DSS, 0 ppm).

Solvent suppression of the water signal for NOESY, ROESY and TOCSY experiments was achieved using a modified WATERGATE sequence (Piotto et al., 1992) in which two gradient pulses of 1 ms was applied on either side of a binomial 3-9-19 pulse. Spectra was routinely acquired over 6024 Hz with 4096 complex data points in $F_2$ and 512 increments in the $F_1$ dimension, with 32 scans per increment for the TOCSY experiments and 80 scans for the NOESY. Slowly exchanging NH protons were detected by acquiring a series of one-dimensional (1D) spectra acquired over 16K data points and with 32 scans.

NMR diffusion experiments were acquired on a Brüker AMX spectrometer equipped with a gradient control unit operating at 500 MHz. All experiments were acquired with 16 or 64 scans at 298 K over 16K of data points and 7575 Hz. A gradient strength of 15.44 G/cm was employed for the diffusion experiments. Each diffusion experiment was obtained from a series of 12 PFGLED spectra in which the delays ($\tau$=20 ms, $\Delta$=50 ms, T=30 ms and $T_e$=14 ms) and where the magnitude of G was held constant but the length of the field gradient pulse ($\delta$) was incremented in 1 ms steps from 0.2 ms to 12.2 ms in the final spectrum.

All spectra were processed on a Silicon Graphics Indigo workstation using Xwinnmr (Bruker) software. For the 2D experiments the $t_1$ dimension was zero-filled to 2048 real data points, and 90° phase-shifted sine-bell window functions were applied prior to Fourier transformation.

Figure 24:
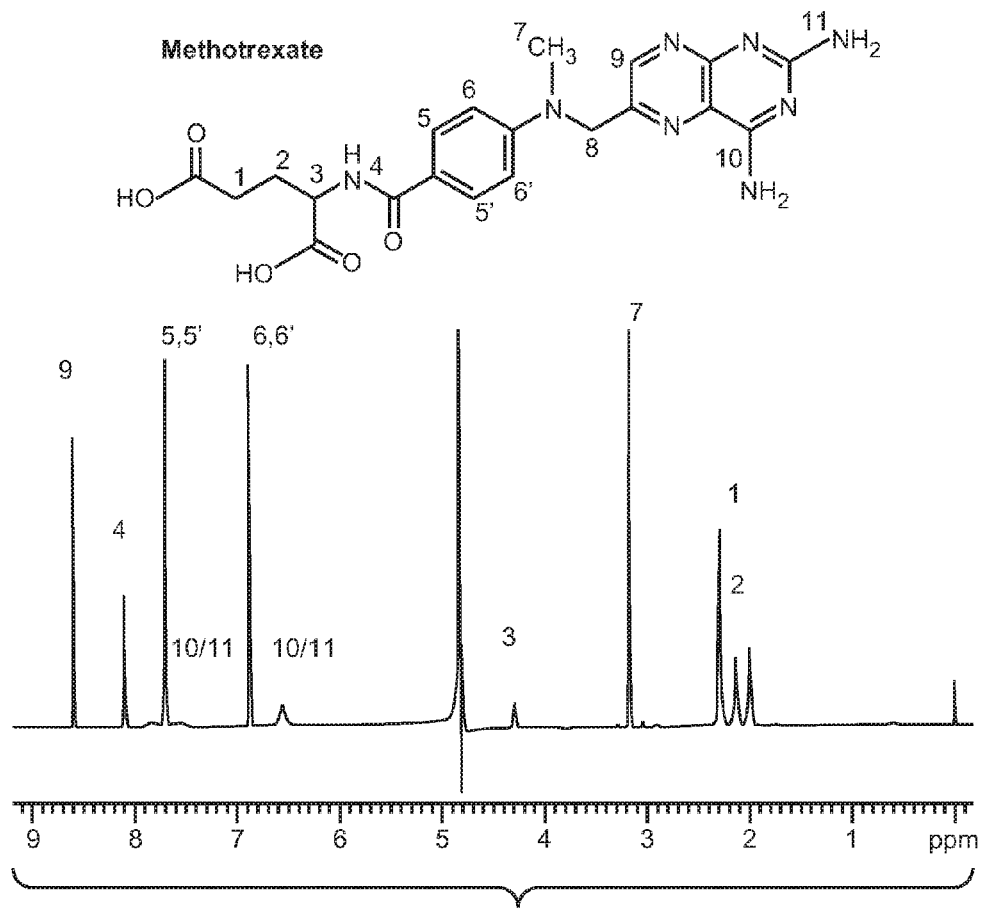
FIG. 24 shows the $^1$H NMR spectrum of the MTX dissolved in $H_2O$. This spectrum readily identifies each group of hydrogens in the MTX.

The NMR experiments were designed to monitor the changes in the $^1$H NMR spectrum of MTX on addition of HA. By monitoring specific changes in the spectrum of the drug MTX, such as the broadening or movement of peaks it is possible to see which regions of the drug molecule, if any, interact with HA. FIG. 24 shows the $^1$H NMR spectrum of the MTX dissolved in $H_2O$. This spectrum readily identifies each group of hydrogens in the methotrexate.

Methotrexate

Figure 25:
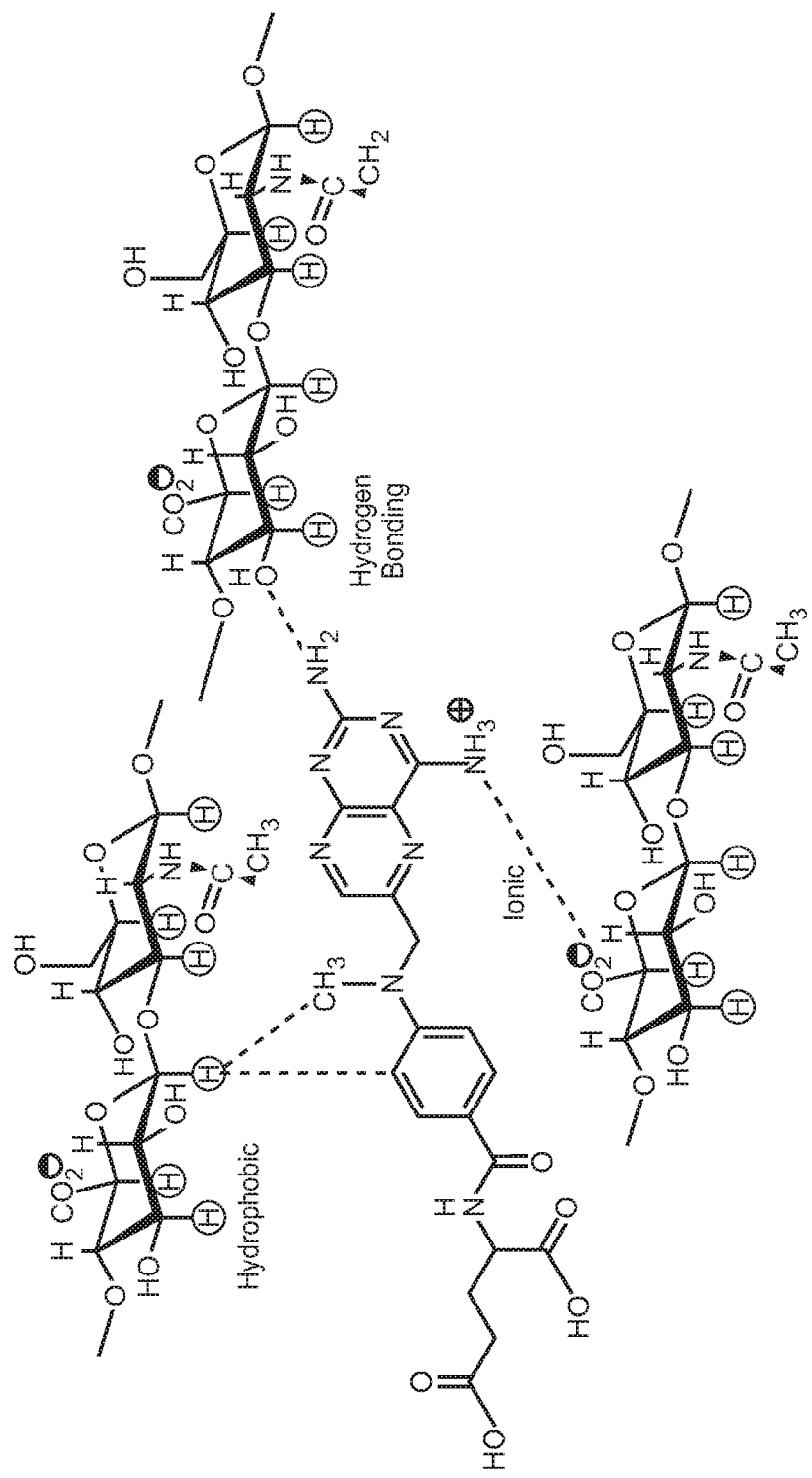
FIG. 25 shows the possible interactions of MTX with HA.

Methotrexate has a number of functional groups that could potentially interact with the hyaluronan molecule. The primary amine moieties on the 2,4-amino-pteridine aromatic ring of MTX could form an ionic association with the carboxyl groups on the hyaluronan molecule. Hydrogen bonding interactions between amine groups on methotrexate and the hydroxyl group on the carbohydrate rings of hyaluronan are another possibility. Hydrophobic interactions are also possible between the hydrophobic aromatic rings of MTX and hydrophobic patches on the folded hyaluronan polymer. These interactions are illustrated in FIG. 25.

Figure 26:
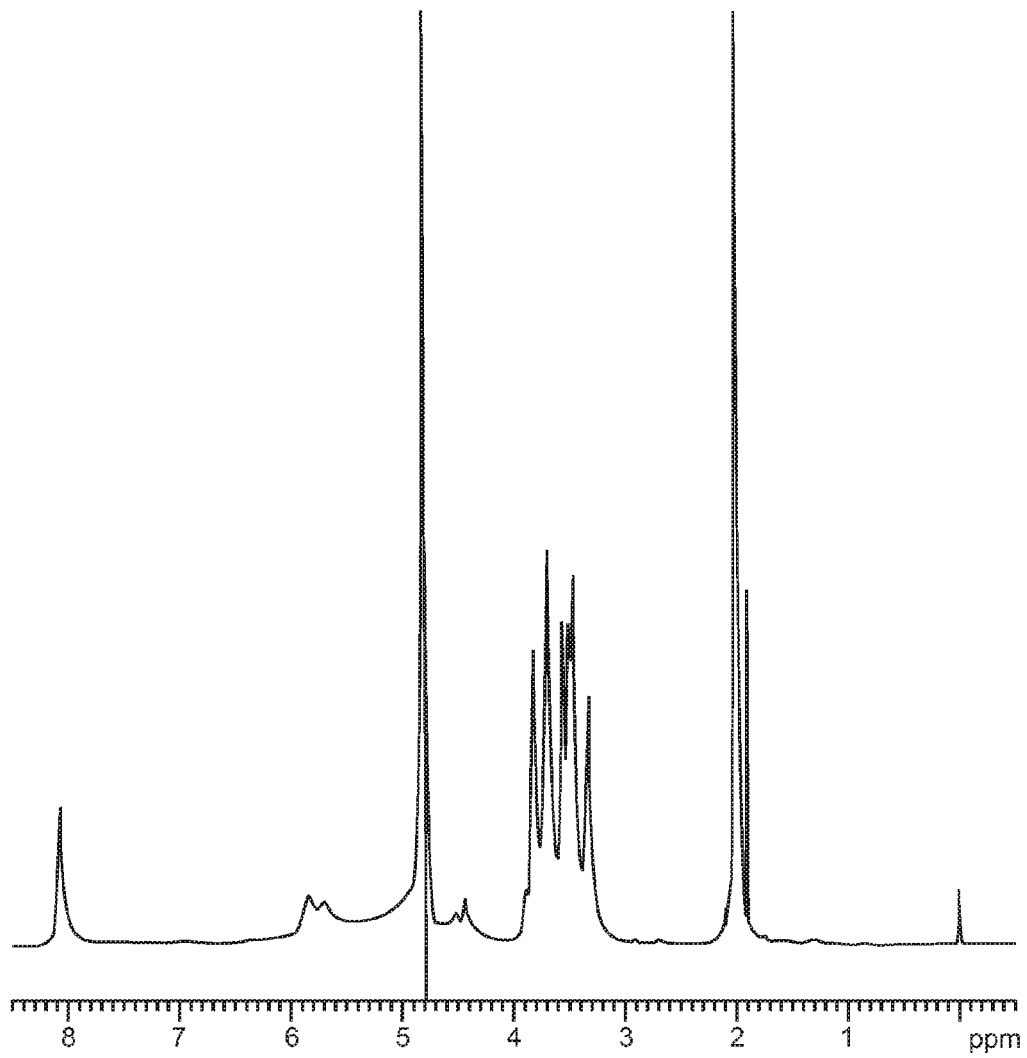
FIG. 26 shows the 600 MHz spectrum of hyaluronic acid at 600 MHz and 298 K.

To address the question of whether there was a specific interaction between the methotrexate and HA NMR experiments were designed to monitor the changes in the $^1$H NMR spectrum of MTX on addition of HA. FIG. 26 shows the 600 MHz spectrum of hyaluronic acid at 600 MHz and 298 K.

Figure 27:
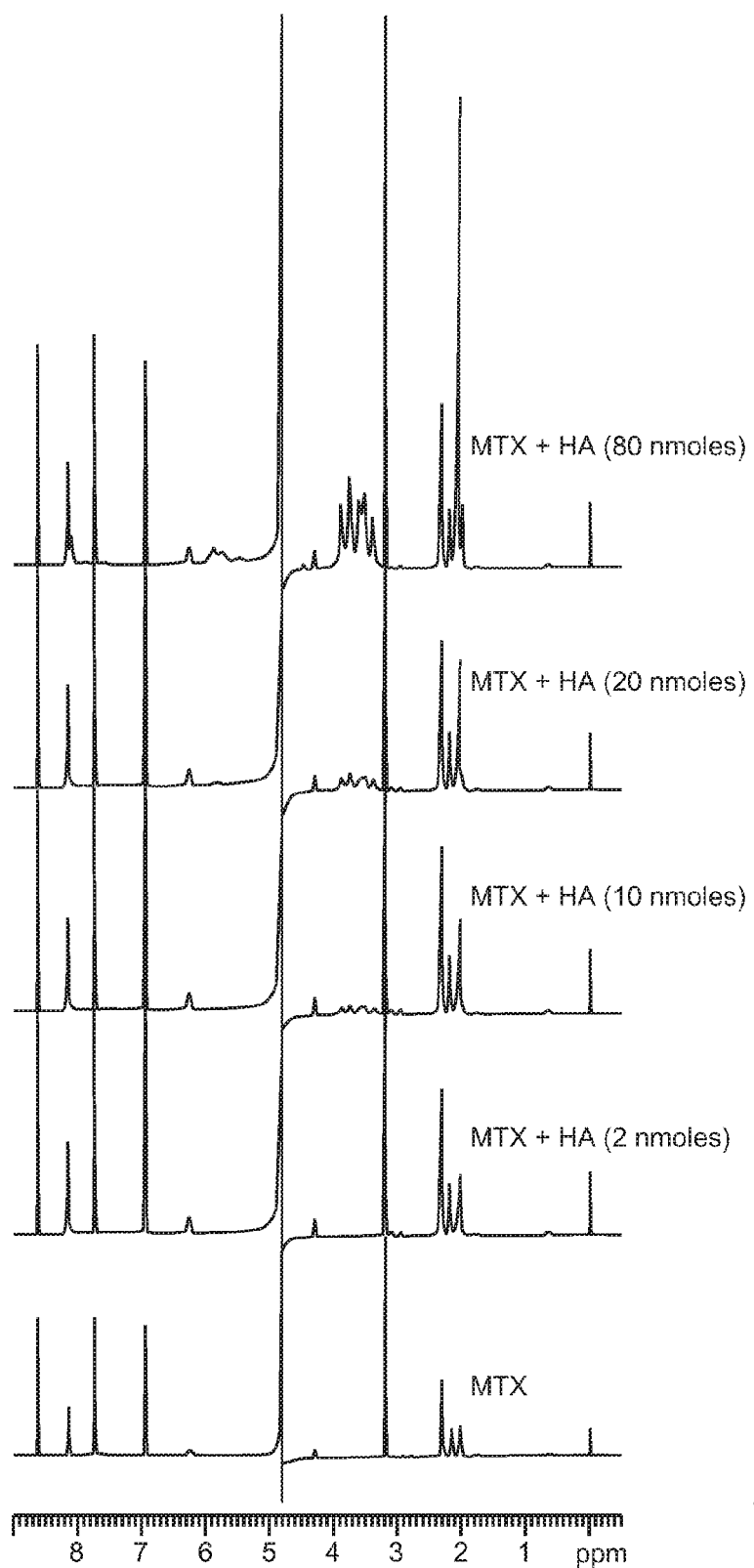
FIG. 27 shows the 600 MHz $^1$H NMR spectrum of MTX alone and MTX with increasing additions of HA (50 kDa) of 2 nmoles, 10 nmoles, 20 nmoles and 80 nmoles at 298 K.

FIG. 27 shows the 600 MHz $^1$H NMR spectrum of MTX alone and MTX with increasing additions of HA (50 kDa) of 2 nmoles, 10 nmoles, 20 nmoles and 80 nmoles at 298 K. These spectra show that there is no change in the chemical shift position of any of the peaks in methotrexate. Additional peaks appearing the spectrum as successive amounts of HA is added are entirely consistent with resonances due to hyaluronic acid. Since there is no change in the chemical shift position of any of the resonances of MTX in these spectra it appears that there is no specific region of the MTX molecule that is interacting with the HA molecule.

One way of determining if there is a strong interaction between the NH groups on the MTX and the acid groups on the HA is to measure the exchange rate of the NH protons. These hydrogens are labile and able to exchange rapidly with the bulk solvent. If however, they are involved in a strong interaction with the HA molecule then they would be protected from the bulk solvent and their exchange rate would be decreased. In this experiment the amine hydrogens of MTX exchange with the deuterium from the $D_2O$ and the rate of exchange should provide an qualitative estimate of the strength of the interaction between the MTX and HA. $^1$H NMR analysis of a solution prepared by addition of deuterium oxide to a solution of MTX and HA dissolved in 0.5% w/v $Na_2CO_3$ (pH 9) showed that within 4 minutes all amine hydrogens of MTX had exchanged with the deuterium in the sample. This result suggests that the amine hydrogens in MTX are not protected from exchange with the bulk solvent.

The reason that the amine hydrogen peaks disappear from the $^1$H NMR spectrum is because deuterium has a very different resonance frequency than hydrogen and therefore doesn't appear in $^1$H NMR spectra. Analogous experiments are routinely used to test whether the backbone amide hydrogens in polypeptide and proteins are protected from solvent. When amide hydrogens of proteins are involved in the hydrogen bonding arrangements that stabilize $\alpha$-helix and $\beta$-sheet secondary structure the exchange rate of these hydrogens is often decreased dramatically. In some cases the hydrogen signals involved in these interaction can persist for hours days or even months depending on the strength of the interaction and it's protection from bulk solvent (for instance in a hydrophobic core of a protein).

Diffusion experiments were performed MTX alone and in the presence of the HA. These experiments could indicate whether the diffusion of the entrapped MTX is retarded by the presence of the HA framework. The results of duplicate $^1$H NMR diffusion experiments indicated that for the vast majority of MTX molecules there was no retardation of the rate of MTX diffusion since there was negligible difference between the diffusion coefficients of MTX and MTX in the presence of HA. This finding could suggest that in the HA framework there are large solvent cavities between the HA molecules that allows the drug to diffuse freely in this medium.

The diffusion experiments suggested that the bulk of the MTX molecules are free diffuse throughout the HA framework. This scenario does not take into consideration if a small proportion (say 5% of MTX molecules) are interacting weakly in a non-specific manner to the HA molecules.

From the previous experiments it is clear that MTX does not interact strongly with HA and the interaction, if any, is not specific. One way to test weakly binding ligands ($10^{-3}$-$10^{-7}$ M) for non-specific binding is to run transferred NOESY experiments. In these 2D experiments crosspeaks will appear if the ligand binds weakly to the macromolecule HA. A transferred NOESY spectrum of MTX/HA showed no crosspeaks due to binding of the MTX to HA which suggests negligible interaction between MTX and HA.

As a further check of whether a small proportion (say 5% of MTX molecules) are interacting weakly in a non-specific manner to the HA molecules. The peaks in a ROESY spectrum should show whether there is even a small proportion of MTX molecules in chemical exchange between free and bound states to the HA. A 250 ms ROESY spectrum did not show any chemical exchange peaks which suggests that not even a small percentage of the MTX interacts with the HA.

5-Fluorouracil

Figure 28:
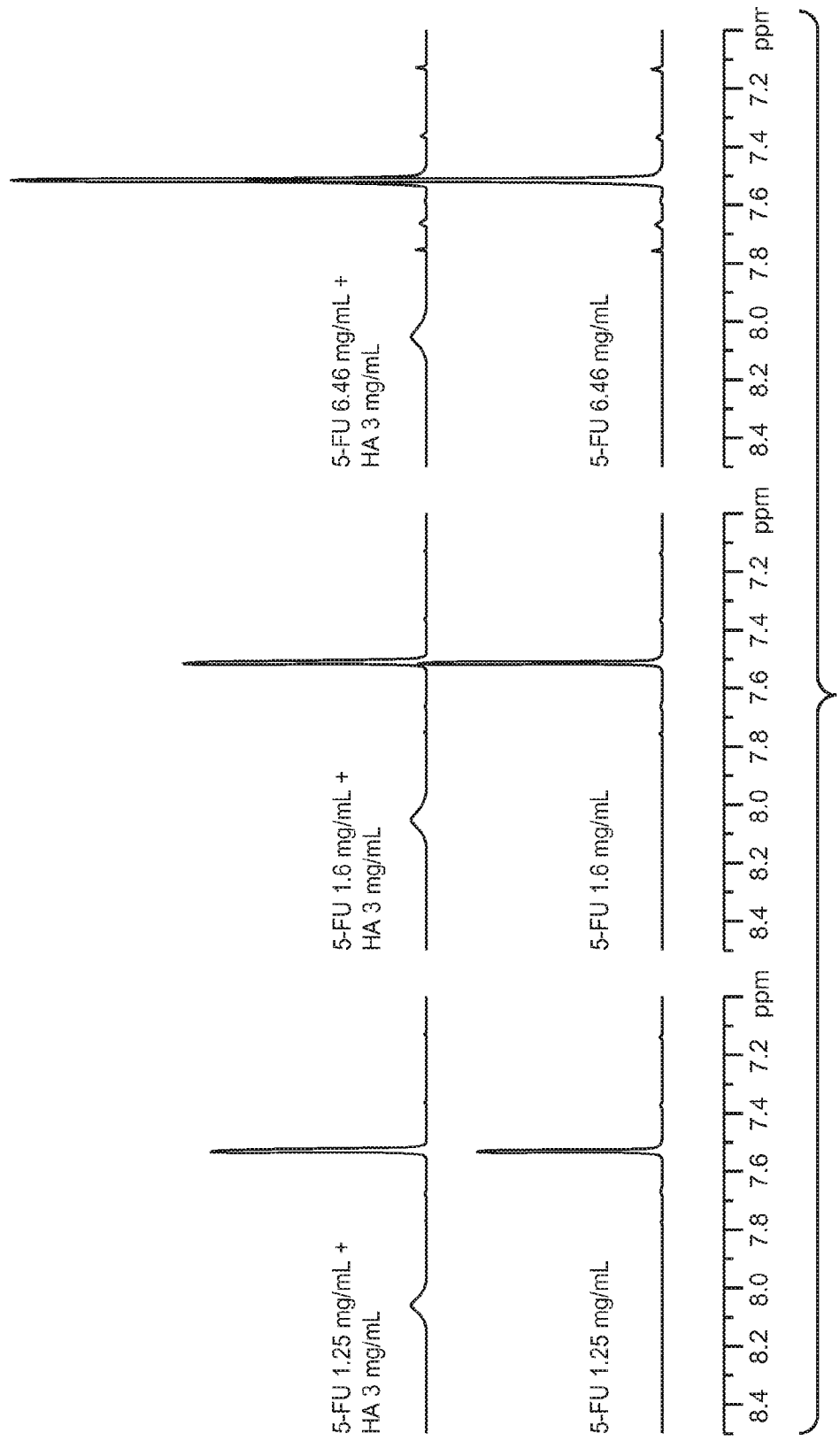
FIG. 28 shows the 600 MHz $^1$H NMR spectra of 5-FU and 5-FU (1.25 mg/mL, 1.6 mg/mL and 6.4 mg/mL) with HA (750 kDa, 3 mg/mL) between 70.0 and 8.5 ppm, at 298 K.

FIG. 28 shows the 600 MHz $^1$H NMR spectra of 5-FU and 5-FU (1.25 mg/mL, 1.6 mg/mL and 6.4 mg/mL) with HA (750 kDa, 3 mg/mL) between 70.0 and 8.5 ppm, at 298 K. Initial experiments to investigate whether there was an interaction were performed with 50 kDa hyaluronic acid. No interaction was observed between the 5-FU and HA (data not shown). To investigate whether an interaction was dependent on the molecular weight of HA used further titration experiments were performed with 750 kDa hyaluronan. The concentrations of 5-FU utilized are equivalent to the HA/5-FU adjuvant therapy Kings College London formulation studies which were conducted in preparation for the Swedish clinical trials. These concentrations were designed to simulate the concentrations used in mixing of HA/5-FU, in the infusion bag and also the HA/5-FU concentration estimated in plasma. Unfortunately, the amine resonances of 5-fluorouracil exchange rapidly with the bulk solvent water at the pH (8.8 to 9.1) of these formulations and therefore these resonances are not visible in the spectrum of the 5-FU. Only one resonance of CH is visible in the spectrum of 5-FU. Lowering of the pH of these solutions is not feasible since the 5-FU will precipitate out of solution at lower pH values. These spectra show that there is no change in the chemical shift position of the CH peak of 5-FU. These spectra indicate that the 5-FU does not appear to be interacting with the HA molecule.

Diffusion experiments were performed 5-FU alone and in the presence of the HA. The results of duplicate $^1$H NMR diffusion experiments shown in Table 13 indicate that 5-FU diffusion is not retarded by the presence of hyaluronan because there is negligible difference between the diffusion coefficients of 5-FU alone and 5-FU in the presence of HA.

TABLE 4

NMR Diffusion Coefficients

| sample | HA stock (750 kDa, 10 mg/mL) | 5-FU (20 mg/mL) | Diffusion coefficient $m^2/s$ |
|---|---|---|---|
| 4 | — | 62.5 μL | $9.245 \times 10^{-10}/8.900 \times 10^{-10}$ |
| 1 | 300 μL | 62.5 μL | $8.701 \times 10^{-10}/9.030 \times 10^{-10}$ |
| 5 | — | 80 μL | $9.141 \times 10^{-10}/9.204 \times 10^{-10}$ |
| 2 | 300 μL | 80 μL | $8.948 \times 10^{-10}/9.021 \times 10^{-10}$ |
| 6 | — | 320 μL | $9.004 \times 10^{-10}/8.997 \times 10^{-10}$ |
| 3 | 300 μL | 320 μL | $8.851 \times 10^{-10}/8.833 \times 10^{-10}$ |

2D experiments, NOESY and ROESY: 2D experiments on 5-FU are not possible since only one resonance is visible in its $^1$H NMR spectrum.

NMR analysis of MTX and 5-FU in the presence of hyaluronan has using titration experiments, deuterium exchange experiments, diffusion experiments and transferred NOESY experiments for MTX, and titration experiments and diffusion experiments for 5-FU have shown that no interaction could be detected between the chemotherapeutic drugs and hyaluronan. These results suggest that entrapment of the chemotherapeutic drugs by the hyaluronan network is sufficient to increase the amount of drug delivered to the pathological site. These results are in total agreement with previous studies using gel filtration chromatography, equilibrium dialysis and CD spectroscopy of the molecular interaction between hyaluronan and MTX and 5-FU which also did not detect an interaction.

REFERENCES

Adams J D, Flora K P, Goldspiel B R, Wilson J W, Finley R, Arbuck S G and Finley R, 1993. *J. Natl. Cancer. Inst. Monographs* 15:23-27.
Akima, K., Ho, H., Iwata, Y., Matsuo, K., Watari, N., Yanagi, M., Hagi, H., Oshima, K., Yagita, A., Atomi, Y & Tatekawa, I. (1996) Evaluation of antitumour activities of hyaluronate binding antitumour drugs: Synthesis, characterization and anti-tumour activity. Jap. J. Drug Targeting 4, 1-8.
Arch R, Wirth K, Hofmann M, Ponta H, Matzku S, Herrlich P and Zoller M, 1992. *Science* 257(5070):682-685.
Bartolazzi A, Peach R, Aruffo A and Stamenkovic I, 1994. *J Exp Med* 180:53-66.
Bax, A. & Davis, D. G. (1985) MLEV-17 based two-dimensional homo-nuclear magnetization transfer spectroscopy. J. Magn. Reson. 65, 355-360.
Bissery M, Guenard D and Lavelle F, 1991. *Cancer Res* 51:4845-4852.
Bisset D, Setanioans A, Cassidy J, Graham M A and Kerr D J, 1993. *Cancer Res* 53:523-527.
Bonadonna G (1976) N Engl J Med Med 294: p. 405.
Bonadonna G (1981) N Engl J Med Med 304: p. 10.
Bonadonna G (1988) Handbook of Medical Oncology, $3^{rd}$ edition. Chicago, Year Book Med Publ, p. 1075.
Cailleau, R. (1974) Breast cancer cell lines *J Natl Cancer Inst* 55: pp 661-674
Carter D, 1990. *Interpretation of Breast Biopsies*, Second Edition Raven Press, New York.
Coradini, D., Pellizzaro, C., Miglierini, G., Daidone, M. G. and Perbellini, A. (1999) Hyaluronic Acid As Drug Delivery For Sodium Butyrate: Improvement Of The Anti-Proliferative Activity On A Breast-Cancer Cell Line. *Int. J. Cancer.* 81: pp. 411-416
Culty M, Nguyen H A and Underhill C B, 1992. *J Cell Biol* 116(4):1055-1062.
Culty, M., Shizari, M., Erik, W., Thompson. and Underhill, C. B. (1994) Binding and degradation of hyaluronan by human breast cancer cell lines expressing different forms of CD44: Correlation with invasive potential. *Journal of Cellular Physiology* 160: pp 275-286
Dye D and Watkins J, 1980. Br. Med. J 280:1353. Endicott J A et al, 1989. *Annual Reviews in Biochemistry* 58: 127-171.
Eriksson, S., Fraser, J R E., Laurent, T C., Perioft, H. and Smedsrod, B. (1983) Endothelia cells are a site of uptake and degradation of hyaluronic acid in the liver. *Exp Cell Res.* 144: pp. 223-228
Fraser, J R E., Appelgren, L E. and Laurent, T C. (1983) Tissue uptake of circulating hyaluronic acid. A whole body autoradiographic study. *Cell Tissue Res* 233(2): pp 285-293
Fraser, J R E., Kimpton, W G., Laurent, T C., Cahill, RNP. and Vakais, N. (1988) Uptake and degradation of hyaluronan in lymphatic tissue. *Biochem. J.* 256: pp. 153-158
Friedrichs G, Folker H J, Arlt P A and Gunthert U, 1995. *The Lancet* 345:1237-1238.
Günthert U, 1993. *Curr Topics Microbiol Immunol* 184:47-63.
Gustafson S, Björkman T, Forsberg N, Lind T, Wikström T and Lidholt K, (1995a). Accessible hyaluronan receptors identical to ICAM-1 in mouse mast tumour cells. Glycoconjugate J. 12, 350-355.
Gustafon, S., Björkman, T., Forsberg, N., McCourt, P., Wikström, T., Lilja, K., Tinner, B., Fuxe, K., Westlin, J.-E., Lidholt, K. Lind, T., Westerberg, G., Bergstrom, M, Langstrom, B., de la Torre, M., Bergh, J., Hagberg, H., Glimelius, B., Lindahl, U., & Laurent, T. C. (1995b) studies on receptors for hyaluronan and the turnover of radioactively-labelled hyaluronan in mice and rats. Royal Soc. Med. Round Table Series no 36, 5-7.
Hall, C L., Yang, B., Yang, X., Zhang, S., Turley, M., Samuel, S., Lange, L A., Wang, C., Curpen, G D., Savani, R C., Greenberg, A H., Turley, E A. (1995). Overexpression of the hyaluronan receptor RHAMM is transforming and is also required for H-ras transformation. *Cell* 82: pp 19-28
Hardwick C, Hoare K, Owens R, Hohn H P, Hook M, Moore D, Cripps V, Austen L, Nance D M, Turley E A, 1992. *J Cell Biol* 117(6): pp 1343-1350.
Harris, J R., Lippman, M E., Veronesi, U. and Willett, W. (1992) Medical Progress in Breast cancer. *The New England Journal of Medicine.* 327: pp. 473-480
Hudecz, F., Clegg, J A., Kajtar, J., Embleton, M J., Pimm, M V., Szekerke, M. and Baldwin, R W. (1993) Influence of carrier on biodistribution and in vitro cytotoxicity of methotrexate-branched polypeptide conjugates. *Bioconjugate Chem* 4: pp 25-33

Inaba, M., Kobayashi, T., Tashiro, T. and Sakurai, Y. (1988). Pharmacokinetic approach to rational therapeutic doses for human tumour-bearing nude mice. *Jpn J Cancer Res* 79(4): pp 509-516

Klein E. S., He, W., Shmizu, S., Ascula, S., & Falk, R. E. (1994). Hyaluronic acid enhances tritiated fluorouracil uptake in experimental cancer. Royal Soc Med Round Table series no 33: 11-15.

Kumar, A., Ernst, R. R. & Wuthrich, K. (1980) Studies of J-Connectivities and selective $^1$H-$^1$H Overhauser effect in H$_2$O solutions of macromolecules by two-dimensional NMR experiments. Biochem. Biophys. Res. Commun. 96 (3), 1156-1163.

Lamszus, K., Jin, L., Fuchs, A., Shi, E., Chowdhury, S., Yao, Y., Polyerni, P J., Laterra, J., Goldberg, I D. and Rosen, E M. (1997) Scatter factor stimulates tumour growth and tumour angiogenesis in human breast cancers in the mammary fat pads of nude mice. *Lab Inv* 76(3): pp 339-353

Laurent, T. C, 1970. In: *Chemistry and Molecular Biology of the Intercellular Matrix*. (Editor: Balazs, E. A.) Academic Press, New York. 2: pp. 703-732.

Laurent, T C., Fraser, J. R. E., Pertoft, H. and Smedsrod, B. (1986) Binding of hyaluronate and chondroitin sulphate to liver endothelial cells. *Biochem J.* 234: pp. 653-658

Lorenz W, Riemann H J, Schmal A, Schult H, Lang S, Ohman C, Weber D, Kapp B, Luben L and Doenicke A, 1977. *Agents Actions*, 7:63-67.

Marion, D. & Wuthrich, K. (1983). Application of phase sensitive two-dimensional correlated spectroscopy (COSY) for measurements of $^1$H-$^1$H spin-spin coupling constants in proteins. Biochem. Biophys. Res. Commun. 113, 967-974.

Martindale, W. (1993) The extra pharmacopoeia 30th Ed (editor: Reynolds, J E F and Parfilt, K.) Pharmaceutical Press, London Mathew A E, Mejillano M R, Nath J P, Himes R H and Stella V J, 1992. *J. Med. Chem.* 35:145-151.

McCourt, P A G., E K, B., Forsberg, N. and Gustafson, S. (1994) Intercellular adhesion molecule-1 is a cell surface receptor for hyaluronan. *J Biol. Chem.* 269: pp. 30081-30084

McEvoy, 1988. *American Hospital Formulary Service-Drug Information* 88. Bethesda, Md., American Society of Hospital Pharmacists, Inc. 2222.

Mikelsaar, R H. and Scott, J E. (1994) Molecular modelling of secondary and tertiary structures of hyaluronan, compared with electron microscopy and NMR data. Possible sheets and tubular structures in aqueous solution. *Glycoconjugate J* 11: pp 65-71

MIMS Medical Network (1996) http://www.medical.netau/mims-get5-FU/711

Nelson, J A. and Falk, R E. (1994) Anticancer research. *Int J Cancer Res Treat*

Nikaido N, 1993. *Science* 264:382-388.

Ogawa Y, Hirakawa K, Nakata B, Fujihara T, Sawada T, Kato Y, Yoshikawa K and Sowa M, 1998. *Clin Cancer Res* 4(1):31-36.

Piotto, M., Saudek, V. & Sklenar, V. (1992) Gradient-tailored excitation for single-quantum NMR spectroscopy of aqueous solutions. J. Biomol. NMR 2, 661-665.

Piper, A A. and Fox, M. (1982) Biochemical basis for the differential sensitivity of human T- and B-Lymphocyte lines to 5-fluorouracil. Cancer Research 42: pp 3753-3760

Rownisky E K, Cazenave L A and Donehower R C, 1990. *J. Natl. Cancer. Inst* 82:1247-1259.

Schabel, F M. (1975) Concepts for systemic treatment of micrometastases. *Cancer* 35: pp. 15-24

Scott, J E., Heatley, F. and Hull, W E. (1989) Secondary structure of hyaluronate in solution. A H-nmr investigation at 300 and 500 MHz in (2H6)dimethyl sulphoxide solution. *Biochem J.* 220: pp 197-205

Shackney, S E., McCormack, G W. and Cuchural, G J. (1978) Growth rate patterns of solid tumours and their relation to responsiveness to therapy: An analytical review. *Annals of Internal Medicine.* 89: pp 107-121

Shibamoto, Y., Murata, R., Miyauchi, S., Hirohashi, M., Takagi, T., Sasai, K., Shibata, T., Oya, N. and Takahashi M. (1996) Combined effect of clininically relevant doses of emitefur, a new 5-fluorouracil derivative, and radiation in murine tumours. *Brit. J. Cancer.* 74: pp 1709-1713

Singh, M., Ghose, T., Kralovec, J., Blair, A H. and Belitsky, P. (1991) Inhibition of human renal cancer by monoclonal-anti-body-linked methotrexate in an ascites tumor model. *Cancer Immunol Immunotherapy* 32 (50): pp 331-334

Stamenkovic I, Aruffo A, Amiot M and Seed B, 1991. *EMBO J.* 10:343-348.

Underhill, C B., Nguyen, H A., Shizari, M. and Culty, M. (1993) CD44 positive macrophages take up hyaluronan during lung development. *Developmental Biology* 155 (2): pp 324-336

Vyas D M, Wong H, Crosswell A R, Casazza A M, Knipe J O and Mamber S W, 1993. *Bioorganic. Med. Chem. Lett.* 3:1357-1360.

Wang C, Thor A D, Moore D H, Zhao Y, Kerschmann R, Stern R, Watson P H and Turley E A, 1998. *Clin Cancer Res* 4(3):567-76.

Wang, C., Zhang, S, and Turley, E A. (1996) The role of hyaluronan and hyaluronan receptors in breast cancer cell invasion, motility and proliferation. In: Fourth International Workshop on Hyaluronan in Drug Delivery. (Editor: Willoughby, D. A) Roy. Soc. Med. Press. pp 37-53

Wani M C, taylor H L and Wall M E, 1971. *J. Am. Chem. Soc* 93:2325-2327.

Waugh W, Trissel L and Stella V J, 1991. *Am. J. Hosp. Pharm* 48: 1520-1524.

Weiss R B, Donehomer R C, Weirnik P H, Ohnuma T, Gralla R J, Leyland-Jones B, 1990. *Br. J. Clin. Oncol* 8:1263-1268.

The claims defining the invention are as follows:

1. A pharmaceutical composition comprising hyaluronan and an anticancer chemotherapeutic agent, wherein said composition is administered intravenously, the concentration of said hyaluronan is ≥1 gram per liter, and wherein the hyaluronan has a molecular weight of about 890 KDa.

2. The pharmaceutical composition of claim 1, wherein the hyaluronan elutes within ±10 ml of the fraction with a molecular weight of 890 KDa as analyzed on a Sephacryl S-1000 1.6 cm×70 cm size exclusion gel column with a fraction size of 2 ml and flow rate of 18 ml/h.

3. The pharmaceutical composition of claim 1, wherein the hyaluronan has a polydispersity of 1.78.

4. The pharmaceutical composition of claim 1, wherein the chemotherapeutic agent is selected from the group consisting of methotrexate, paclitaxel, 5-fluorouracil and cyclophosphamide or combinations thereof.

5. The pharmaceutical composition of claim 1, wherein the chemotherapeutic agent is cyclophosphamide.

6. The pharmaceutical composition of claim 1, wherein the chemotherapeutic agent is paclitaxel.

\* \* \* \* \*